(12) United States Patent
Foshee et al.

(10) Patent No.: US 8,475,404 B2
(45) Date of Patent: Jul. 2, 2013

(54) VIAL ACCESS AND INJECTION SYSTEM

(75) Inventors: David L. Foshee, Apex, NC (US);
Theodore J. Mosler, Raleigh, NC (US);
Bryan J. Peters, Raleigh, NC (US);
Nicholas J. Jardine, Cary, NC (US);
Todd M. Korogi, Raleigh, NC (US)

(73) Assignee: Yukon Medical, LLC, Morrisville, NC (US)

( * ) Notice: Subject to any disclaimer, the term of this patent is extended or adjusted under 35 U.S.C. 154(b) by 250 days.

(21) Appl. No.: 12/674,406

(22) PCT Filed: Aug. 21, 2008

(86) PCT No.: PCT/US2008/073870
§ 371 (c)(1),
(2), (4) Date: Feb. 9, 2011

(87) PCT Pub. No.: WO2009/026443
PCT Pub. Date: Feb. 26, 2009

(65) Prior Publication Data
US 2011/0264037 A1    Oct. 27, 2011

Related U.S. Application Data

(60) Provisional application No. 60/965,555, filed on Aug. 21, 2007, provisional application No. 61/003,676, filed on Nov. 19, 2007, provisional application No. 61/066,974, filed on Feb. 25, 2008.

(51) Int. Cl.
*A61M 37/00* (2006.01)

(52) U.S. Cl.
USPC .................. 604/82; 604/86; 604/88

(58) Field of Classification Search
USPC ............... 604/82, 86, 88, 411–416, 905, 192, 604/200
See application file for complete search history.

(56) References Cited

U.S. PATENT DOCUMENTS

| 4,316,462 A | 2/1982 | Baker |
| 4,676,788 A | 6/1987 | Vincent |
| 4,994,029 A | 2/1991 | Rohrbough |

(Continued)

FOREIGN PATENT DOCUMENTS

| EP | 0 521 460 B1 | 9/1995 |
| EP | 0 814 866 B1 | 1/1998 |

(Continued)

OTHER PUBLICATIONS

Korean Intellectual Property Office, International Search Report, Feb. 10, 2009, pp. 1-2, Republic of Korea.

(Continued)

*Primary Examiner* — Laura Bouchelle
(74) *Attorney, Agent, or Firm* — Christopher J. Knors; Moore & Van Allen PLLC

(57) ABSTRACT

A device for mixing and transferring is described. The device comprises a housing having open ends, a container accessing member having at least one fluid conduit therethrough, the container accessing member extending generally outwardly from one end of the housing. The device comprises a fluid delivery device accessing member having at least one fluid conduit therethrough, the fluid delivery device accessing member extending generally outwardly from the other end of the housing having the container accessing member, the fluid delivery device accessing member and the container accessing member in fluid communication therewith.

20 Claims, 47 Drawing Sheets

U.S. PATENT DOCUMENTS

| | | |
|---|---|---|
| 5,088,996 A | 2/1992 | Kopfer et al. |
| 5,102,406 A | 4/1992 | Arnold |
| 5,152,965 A | 10/1992 | Fisk et al. |
| 5,232,029 A | 8/1993 | Knox et al. |
| 5,257,650 A | 11/1993 | Fisk et al. |
| 5,279,576 A | 1/1994 | Loo et al. |
| 5,297,433 A | 3/1994 | Elgas |
| 5,304,163 A | 4/1994 | Bonnici et al. |
| 5,352,191 A | 10/1994 | Sunago et al. |
| 5,423,753 A | 6/1995 | Fowles et al. |
| 5,445,631 A | 8/1995 | Uchida |
| 5,464,123 A | 11/1995 | Scarrow |
| 5,466,220 A | 11/1995 | Brenneman |
| 5,520,659 A | 5/1996 | Hedges |
| 5,522,804 A | 6/1996 | Lynn |
| 5,526,853 A | 6/1996 | McPhee et al. |
| 5,527,306 A | 6/1996 | Haining |
| 5,554,128 A | 9/1996 | Hedges |
| 5,599,302 A | 2/1997 | Lilley et al. |
| 5,636,660 A * | 6/1997 | Pfleiderer et al. ............. 137/550 |
| 5,641,010 A | 6/1997 | Maier |
| 5,685,845 A | 11/1997 | Grimard |
| 5,716,346 A | 2/1998 | Farris |
| 5,776,124 A | 7/1998 | Wald |
| 5,785,701 A | 7/1998 | Sams et al. |
| 5,833,213 A | 11/1998 | Ryan |
| 5,833,674 A | 11/1998 | Turnbull et al. |
| 5,846,233 A | 12/1998 | Lilley et al. |
| 5,873,872 A | 2/1999 | Thibault et al. |
| 5,890,610 A | 4/1999 | Jansen et al. |
| 5,989,237 A | 11/1999 | Fowles et al. |
| 6,019,750 A | 2/2000 | Fowles et al. |
| 6,022,339 A | 2/2000 | Fowles et al. |
| 6,063,068 A | 5/2000 | Fowles et al. |
| D427,308 S | 6/2000 | Zinger |
| 6,071,270 A | 6/2000 | Fowles et al. |
| 6,090,092 A | 7/2000 | Fowles et al. |
| 6,113,583 A | 9/2000 | Fowles et al. |
| 6,139,534 A | 10/2000 | Niedospial, Jr. et al. |
| 6,146,362 A | 11/2000 | Turnbull et al. |
| 6,149,623 A | 11/2000 | Reynolds |
| 6,159,192 A * | 12/2000 | Fowles et al. ................. 604/403 |
| 6,168,037 B1 | 1/2001 | Grimard |
| 6,209,738 B1 | 4/2001 | Jansen et al. |
| 6,238,372 B1 | 5/2001 | Zinger et al. |
| D445,501 S | 7/2001 | Niedospial, Jr. |
| 6,269,976 B1 | 8/2001 | DeJonge |
| 6,343,629 B1 | 2/2002 | Wessman et al. |
| 6,355,023 B1 | 3/2002 | Roth et al. |
| 6,364,865 B1 | 4/2002 | Lavi et al. |
| 6,379,340 B1 | 4/2002 | Zinger et al. |
| 6,409,708 B1 | 6/2002 | Wessman |
| 6,453,956 B2 | 9/2002 | Safabash |
| 6,474,375 B2 | 11/2002 | Spero et al. |
| 6,478,771 B1 | 11/2002 | Lavi et al. |
| 6,503,240 B1 | 1/2003 | Niedospial, Jr. et al. |
| 6,544,246 B1 | 4/2003 | Niedospial, Jr. |
| 6,558,365 B2 | 5/2003 | Zinger et al. |
| 6,571,837 B2 | 6/2003 | Jansen et al. |
| 6,582,415 B1 | 6/2003 | Fowles et al. |
| 6,610,040 B1 | 8/2003 | Fowles et al. |
| 6,638,244 B1 | 10/2003 | Reynolds |
| 6,656,433 B1 | 12/2003 | Sasso |
| 6,663,593 B2 | 12/2003 | Ito |
| 6,666,852 B2 | 12/2003 | Niedospial, Jr. |
| 6,699,229 B2 | 3/2004 | Zinger et al. |
| 6,719,719 B2 | 4/2004 | Carmel et al. |
| 6,752,180 B2 | 6/2004 | Delay |
| 6,832,994 B2 | 12/2004 | Niedospial, Jr. et al. |
| 6,852,103 B2 | 2/2005 | Fowles et al. |
| 6,875,203 B1 | 4/2005 | Fowles et. al. |
| 6,875,205 B2 | 4/2005 | Leinsing |
| 6,890,328 B2 | 5/2005 | Fowles et al. |
| 6,901,975 B2 | 6/2005 | Aramata et al. |
| 6,948,522 B2 | 9/2005 | Newbrough et al. |
| 6,994,315 B2 | 2/2006 | Ryan et al. |
| 6,997,917 B2 | 2/2006 | Niedospial, Jr. et al. |
| 7,074,216 B2 | 7/2006 | Fowles et al. |
| 7,077,835 B2 | 7/2006 | Robinson et al. |
| 7,140,401 B2 | 11/2006 | Wilcox et al. |
| 7,261,698 B2 | 8/2007 | Sampson et al. |
| 7,294,122 B2 | 11/2007 | Kubo et al. |
| D561,348 S | 2/2008 | Zinger et al. |
| 7,326,194 B2 | 2/2008 | Zinger et al. |
| 7,358,505 B2 | 4/2008 | Woodworth et al. |
| 7,425,209 B2 | 9/2008 | Fowles et al. |
| 7,442,189 B2 | 10/2008 | Curutcharry |
| 7,491,197 B2 | 2/2009 | Jansen et al. |
| 7,507,227 B2 | 3/2009 | Fangrow |
| 7,510,548 B2 | 3/2009 | Fangrow |
| 7,632,261 B2 | 12/2009 | Zinger et al. |
| 2001/0021820 A1 | 9/2001 | Lynn |
| 2002/0066715 A1 | 6/2002 | Niedospial |
| 2002/0087118 A1 | 7/2002 | Reynolds |
| 2002/0087144 A1 | 7/2002 | Zinger |
| 2002/0115980 A1 | 8/2002 | Niedospial |
| 2002/0124905 A1 | 9/2002 | Draughn |
| 2003/0032935 A1 | 2/2003 | Damiano |
| 2003/0199846 A1 | 10/2003 | Fowles |
| 2004/0073189 A1 | 4/2004 | Wyatt |
| 2004/0115099 A1 | 6/2004 | Smith |
| 2004/0199139 A1 | 10/2004 | Fowles |
| 2004/0210207 A1 | 10/2004 | Amisar |
| 2005/0124964 A1 | 6/2005 | Niedospial, Jr. |
| 2005/0137523 A1 | 6/2005 | Wyatt et al. |
| 2005/0137566 A1 | 6/2005 | Fowles et al. |
| 2005/0148994 A1 | 7/2005 | Leinsing |
| 2005/0151105 A1 | 7/2005 | Ryan et al. |
| 2006/0025747 A1 | 2/2006 | Sullivan et al. |
| 2006/0030832 A1 | 2/2006 | Niedospial, Jr. et al. |
| 2006/0040340 A1 | 2/2006 | Greene |
| 2006/0089594 A1 | 4/2006 | Landau |
| 2006/0155257 A1 | 7/2006 | Reynolds et al. |
| 2007/0032775 A1 | 2/2007 | Niedospial, Jr. et al. |
| 2007/0060904 A1 | 3/2007 | Vedrine et al. |
| 2007/0079894 A1 | 4/2007 | Kra et al. |
| 2007/0088252 A1 | 4/2007 | Pestotnik et al. |
| 2007/0088313 A1 | 4/2007 | Zinger et al. |
| 2007/0156112 A1 | 7/2007 | Walsh |
| 2007/0270778 A9 | 11/2007 | Zinger et al. |
| 2008/0009789 A1 | 1/2008 | Zinger et al. |
| 2008/0021381 A1 | 1/2008 | Lurvey et al. |
| 2008/0132851 A1 | 6/2008 | Shaw et al. |
| 2008/0140021 A1 | 6/2008 | Richmond |
| 2008/0172024 A1 | 7/2008 | Yow |
| 2008/0249479 A1 | 10/2008 | Zinger et al. |
| 2008/0283741 A1 | 11/2008 | Mukaibatake |
| 2008/0300570 A1 | 12/2008 | Fowles et al. |
| 2009/0024096 A1 | 1/2009 | Hai et al. |
| 2009/0054834 A1 | 2/2009 | Zinger et al. |
| 2009/0082734 A1 | 3/2009 | Walters et al. |
| 2009/0082750 A1 | 3/2009 | Denenburg et al. |
| 2009/0177177 A1 | 7/2009 | Zinger et al. |
| 2009/0198217 A1 | 8/2009 | Thorne, Jr. et al. |

FOREIGN PATENT DOCUMENTS

| | | |
|---|---|---|
| EP | 1 454 650 B1 | 9/2004 |
| JP | 2004097253 A | 4/2004 |
| WO | WO 97/20536 | 6/1997 |

OTHER PUBLICATIONS

Japanese Office Action (JP 2010-522028); dispatch date: Feb. 8, 2013.

* cited by examiner

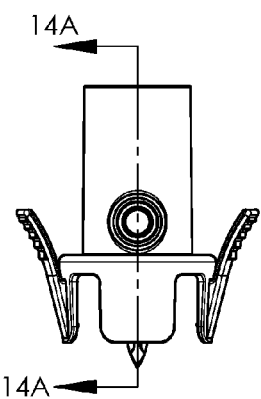 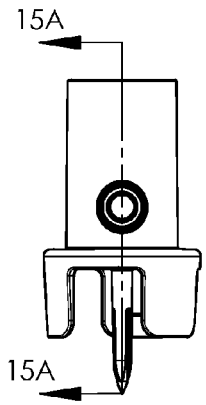
FIG. 14        FIG. 15
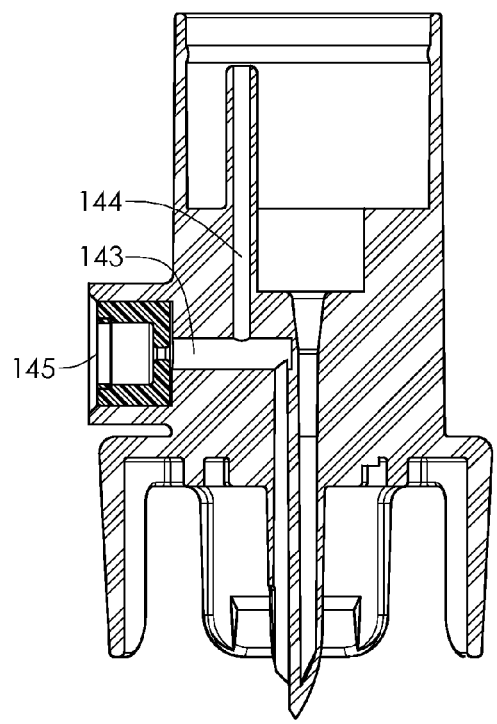 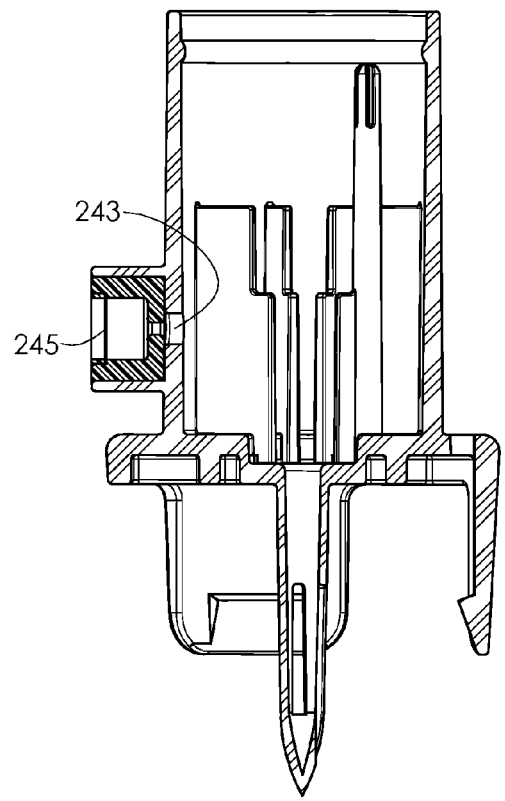
FIG. 14A        FIG. 15A

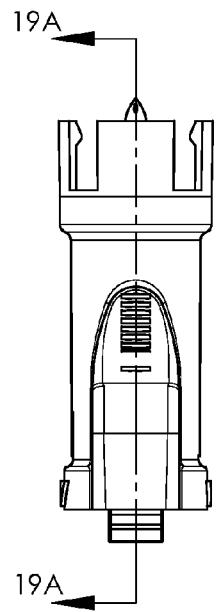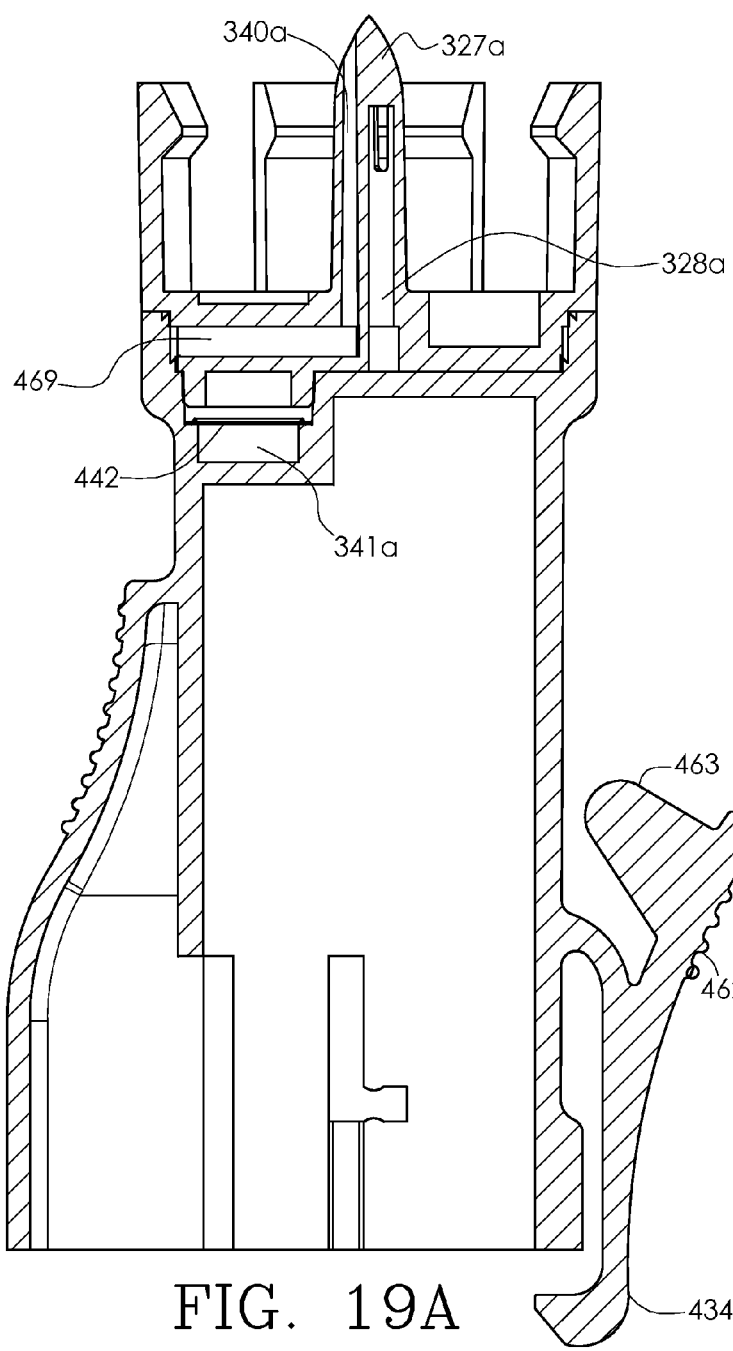
FIG. 19
FIG. 19A

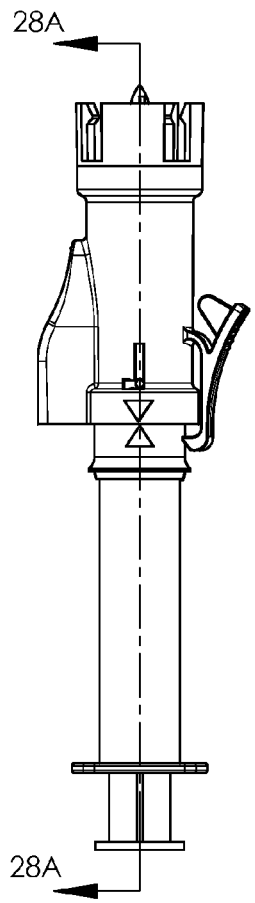
FIG. 28
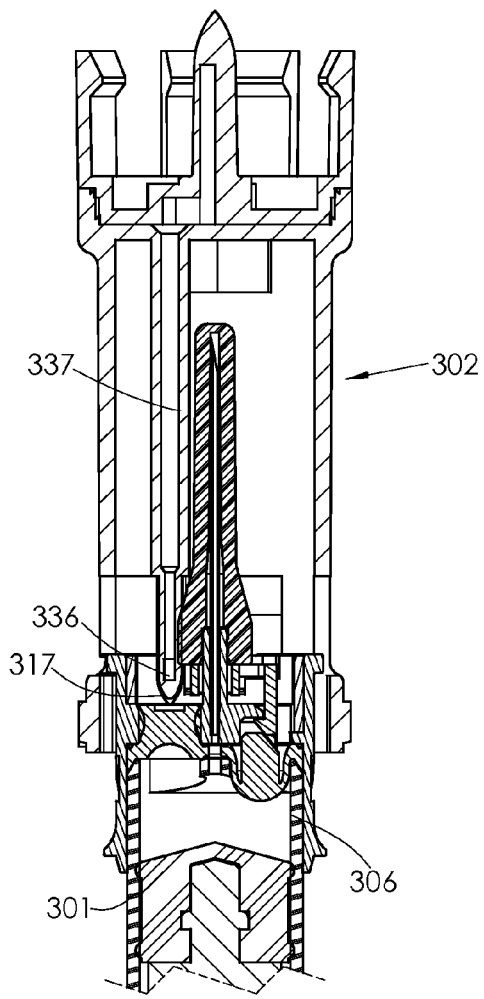
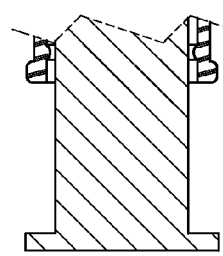
FIG. 28A

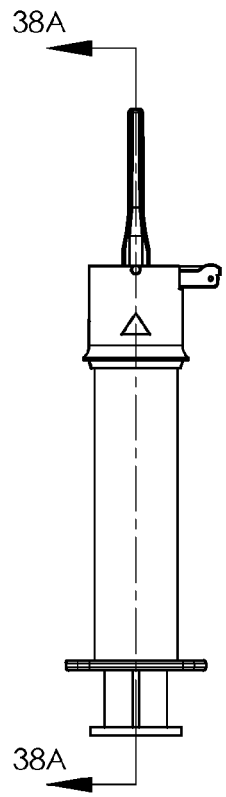
FIG. 38
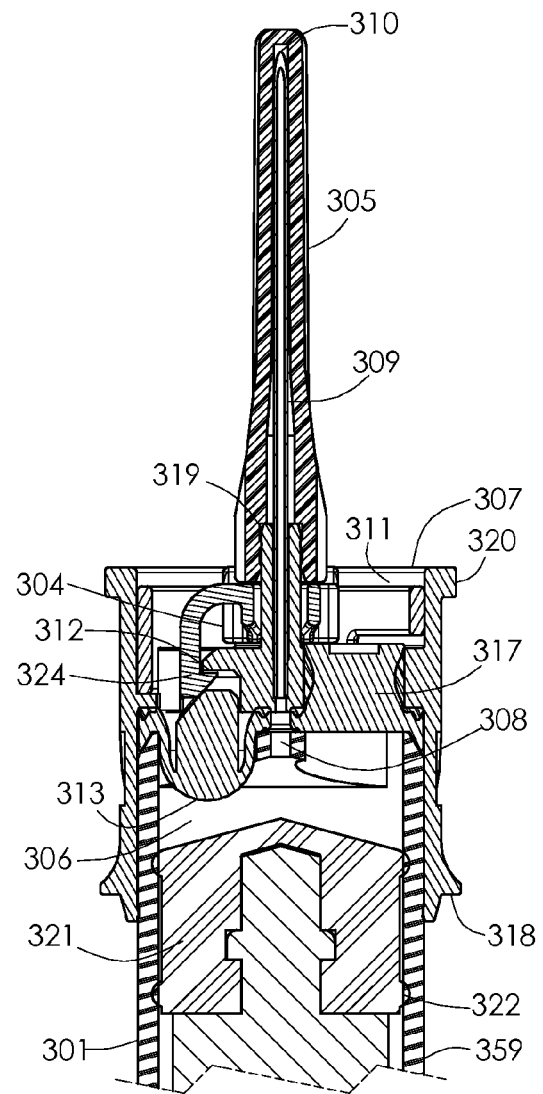
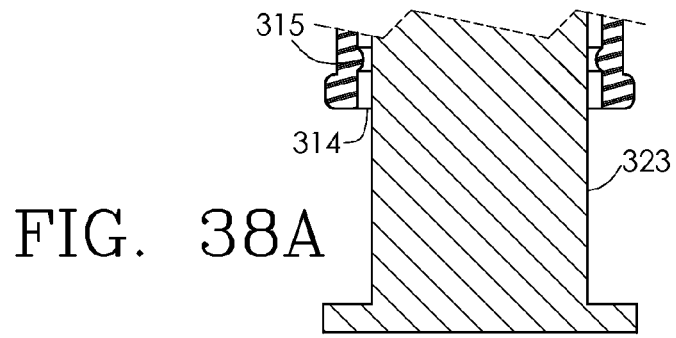
FIG. 38A

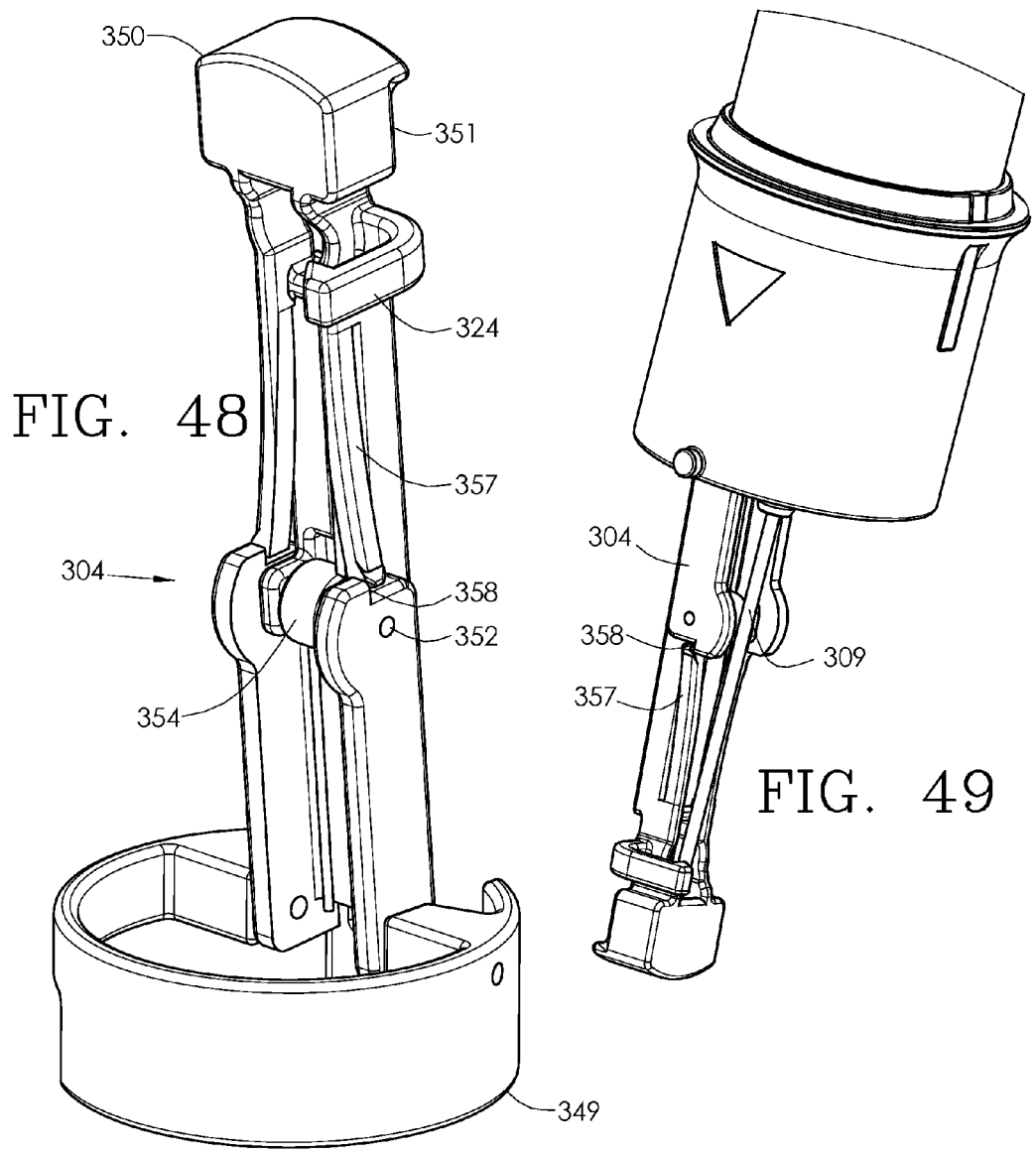

VIAL ACCESS AND INJECTION SYSTEM

CROSS-REFERENCE TO RELATED APPLICATIONS

This application claims the benefit of U.S. Provisional Application No. 60/965,555, filed Aug. 21, 2007; 61/003,676, filed Nov. 19, 2007; and 61/066,974, filed Feb. 25, 2008, all of which are incorporated herein by reference in their entirety.

TECHNICAL FIELD

This disclosure relates to a mixing and transfer device for injectable medication.

BACKGROUND

Lypholized and similar liquid drugs are typically provided in medicament vials with standard elastomeric closure sizes, such as 20 mm and 13 mm diameter closures. Administration of these drugs, if administered to patients via routes such as intramuscular, intravenous, intracutaneous, and the like, require that delivery devices be attached to a syringe, and then administered to the patient, for example using needles. The needles used to administer the drug to the patient are often different from the needle or access device used to access the medicament vial(s). Certain needle types are special for drug vials—such as anti-coring needles—and would be inappropriate for use when injecting a patient. For instance, a pharmacy technician may use a high flow rate needle to withdraw diluent from one source, and inject it into a lyophilized drug vial. The vial would be mixed up, and drawn back into the syringe—or perhaps a new clean syringe. Then often times the drug preparation needle is removed and disposed of and an alternate sterile needle, appropriate for the specific type of patient injection (e.g. deltoid intramuscular), would be placed on to take the prepared drug-filled syringe with new capped needle to the patient. The prescribed mixing and preparation of drugs vary, which may require certain drugs to be mixed carefully, or flow through specific sized needles. The lyophilized drug may be expensive, requiring that a little as possible or substantially nothing is left in the drug vial.

Vial elastomeric closure design and materials vary and may require the user to match up the appropriate needle or access device with the medicament vial. The medicament injection process varies by both the location and type of injection. Since the drug preparation is often completed by a technician or nurse, not the prescriber, and/or different from the administrator of the medication, there may be multiple steps in the process that may result in error. Additionally, due to the number of steps, the time of preparation can be significant, adding cost and complexity to the process. Finally, switching needles often for drug preparation and administration may lead to an increased likelihood of needle-stick injuries.

SUMMARY

Described herein is a vial access device that addresses several of the issues described above. The vial access device described herein reduces the number of steps and potential errors for the preparation and the administration of drugs that are delivered to patients via needles, spray nozzles, or luer connectors. The vial access device described herein provides larger flow paths to ease and speed up drug preparation, and may protect the drug and/or blood products from mechanical breakdown or hemolysis. The vial access device described herein protects the needle or component for injection during preparation, maintaining its cleanliness, sharpness, and assures its readiness for patient administration. The vial access device described herein may prevent or substantially eliminate unintentional and/or accidental needle-sticks of users and healthcare personnel by accommodating needle safety mechanisms.

In one aspect, a device for mixing and transferring is described. The device comprises a housing having first and second open ends, a vial accessing member having at least one fluid conduit therethrough, the vial accessing member extending generally outwardly from one end of the housing. The device comprises a syringe accessing member having at least one fluid conduit therethrough, the syringe accessing member extending generally outwardly from the other end of the housing having the vial accessing member, the syringe accessing member and the vial accessing member in fluid communication therewith. In one aspect, the device further comprises receiving means within the housing, the receiving means configured to receive a dispensing member of the syringe.

In another aspect a combination is described. The combination comprising a device for mixing and transferring, a fluid delivery device, and optionally a container having a transferable substance. The device comprises a housing having first and second open ends, a container accessing member having at least one fluid conduit therethrough, the container accessing member extending generally outwardly from one end of the housing. The device comprises a fluid delivery device accessing member having at least one fluid conduit therethrough, the fluid delivery device accessing member extending generally outwardly from the other end of the housing having the container accessing member, the fluid delivery device accessing member and the container accessing member in fluid communication therewith. The fluid delivery device is reversibly securable to the fluid delivery device attaching means. The fluid delivery device comprises a dispensing member at a proximal end, an access port at the proximal end configured to receive the fluid delivery device accessing member, and a plunger at a distal end, the plunger having a distal end slidably received towards the dispensing member of the syringe. The combination optionally comprises at least one container reversibly securable to the container attaching means, the container optionally comprising a transferable substance.

BRIEF DESCRIPTION OF THE FIGURES

FIGS. 14-14A and 15-15A are sectional plane and cross-sectional views, respectively, of a vial access device embodiment.

FIGS. 18-18A and 19-19A are sectional plane and cross-sectional views, respectively, of a vial access device embodiment.

FIGS. 28-28A are sectional plane and partial cross-sectional views of a syringe and vial access device combination embodiment.

FIGS. 37-37A and 38-38A are sectional plane and partial cross-sectional views, respectively, of a needle-stick safety mechanism embodiment with needle cover.

FIGS. 47-48 are perspective views of a needle-stick safety mechanism embodiment shown in an un-deployed and deployed configuration, respectively.

FIG. 49 is a perspective view of a needle-stick safety mechanism embodiment in a fully deployed configuration.

DETAILED DESCRIPTION

Figure 1:
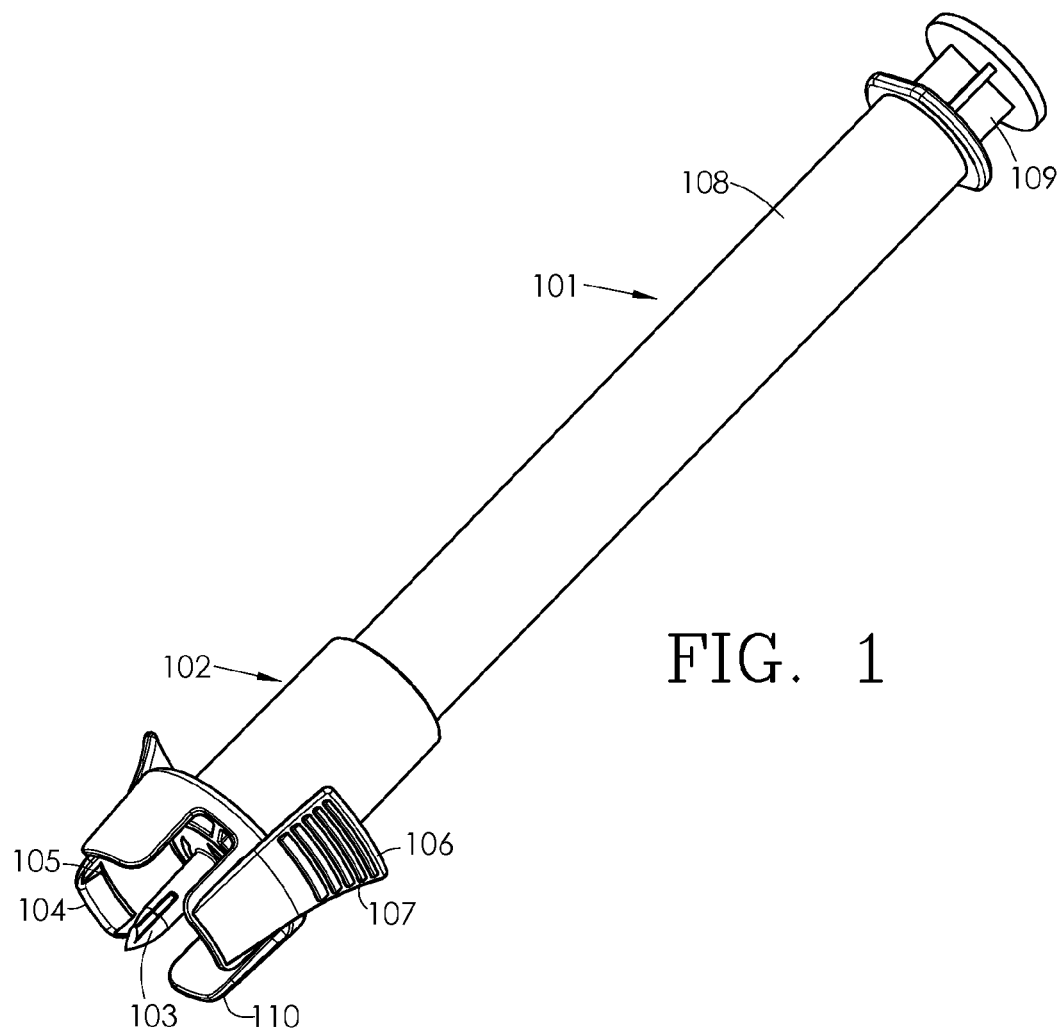
FIG. 1 is a perspective view of a combination vial access device and fluid delivery device embodiment.

Disclosed herein is a device for mixing and transferring. The device comprises a housing having open ends, a container accessing member having at least one fluid conduit therethrough, the container accessing member extending generally outwardly from one open end of the housing. The housing also comprises a fluid delivery device accessing member having at least one fluid conduit therethrough, the fluid delivery device accessing member extending generally towards the other open end of the housing, the fluid delivery device accessing member and the container accessing member in fluid communication therewith. The device further comprises receiving means within the housing, the receiving means configured to receive a dispensing member of the fluid delivery device. The access device is configured to provide an interface between the contents of a container and a fluid delivery device. The access device is configured such that the fluid delivery device and the container may reversibly and sealably mate to the access device and be in fluid communication therewith.

Access Housing

The access device comprises a housing having open ends, a container accessing member having at least one fluid conduit. The container accessing member extends generally outwardly from one end of the housing. The device also comprises a fluid delivery device accessing member having at least one fluid conduit therethrough, the fluid delivery device accessing member extending generally outwardly from the opposite end of the housing having the container accessing member, the fluid delivery device accessing member and the piercing accessing member in fluid communication with each other.

The fluid delivery device accessing member is configured to bypass the dispensing member of the fluid delivery device to allow a higher flow rate during aspiration and to maintain the integrity of the dispensing member during preparation of the fluid. The fluid delivery device accessing member and the access housing may comprise any number of parts, which may be joined together in a sealable relationship. In one aspect, the access device is a vial access device configured for accepting a drug vial. The drug vial contains a pierceable septum or the like. The vial access device comprises a piercing member extending from the end of the vial access device housing. The vial access device is configured such that the vial accessing member pierces the septum of the vial to access the vial.

The vial access device preferably has one or more piercing members, at least one of the piercing members having a lumen open at its distal end. The proximal end of the piercing members are advantageously attached via the interconnecting conduits within the access housing to provide fluid communication between the container, such as a drug vial, and a fluid delivery device, such as a syringe. The piercing member is adapted to support and penetrate standard drug vials filled with powdered or lyophilized drugs or liquid diluent, while the syringe is adapted to transfer liquid diluent and drug solutions between the vials and the syringe. At least one lumen is open at the vial accessing member and provides a fluid communication with the interconnecting conduit. Venting of a piercing member to the ambient may be provided.

The vial access device may further comprise attachment means to reversibly secure the vial access device to the vial. The vial access device may also comprise a plurality of flexible primary tabs extending toward the second end of the device where they form a vial attachment latch at its distal end for use in reversibly securing the component to a vial. Each tab having the vial attachment latch may also have a secondary tab extending from the primary tab toward the first end; a secondary tab also having an end that may have a gripping means integrated therewith. The component may also include tabs used for guiding the vial access adapter onto drug vial without attachment latches. The vial access adapter may be removed from drug vial and remain attached to the fluid delivery device.

In one aspect, the sealable interface of the other open end of the vial access device is configured for a standard syringe interface. Thus, the sealable interface may be designed to sealably mate with standard or custom syringes. The sealable interface may be permanently affixed to the syringe or may be configured to be non-releasable upon engagement with the syringe. The sealable interface permanently affixed to the syringe may reduce tooling requirements and/or costs. The housing and any of its integrated or attached components may be constructed of any of a variety of materials. Preferably, the housing is constructed of a material that is biocompatible and able to withstand exposure to various sterilization methods and the intended fluid media. Materials that may be used for the housing include, but are not limited to, polycarbonate, polyethylene, polypropylene, PBT and the like. Glass or carbon fibers, fillers or other strengthening media may be added to these plastics for rigidity as required.

Fluid Delivery Device Accessing Member

The access housing comprises a fluid device accessing member configured to access a fluid delivery device via an accessing member. The accessing member has at least one fluid conduit. The accessing member extends generally toward the other open end of the access housing, the fluid delivery device accessing member and the container accessing member being in fluid communication with each other.

In one aspect, the fluid delivery device is a syringe having a dispensing member and the fluid delivery device accessing member is a syringe accessing member. The syringe accessing member has at least one fluid conduit. The syringe accessing member extends generally toward the other open end of the access housing, the syringe accessing member and the container accessing member being in fluid communication with each other.

The syringe accessing member comprises a fluid path to bypass the dispensing member of the syringe. For example, the vial access device provides for fluid bypass of the needle of a syringe. The vial access device may be configured such that a higher flow rate when drawing fluid into the fluid delivery device is possible than would be by using the dispensing member of the fluid dispensing device. The fluid bypass also maintains the integrity of the dispensing member (e.g. sharpness of a needle) until it is needed for final dispensing. The fluid bypass may comprise a fluid passage in the vial access device in fluid communication with a sealable access port (described herein) into the distal end of the syringe barrel adjacent the dispensing member such that during transfer and/or mixing, fluid is substantially diverted from traversing the dispensing member. The access port may be a self-closing, sealable passage into the syringe barrel such that during an injection stroke, fluid is delivered only through the needle. This may allow, for example, a smaller needle size on the fluid delivery device thereby reducing discomfort to the patient during injections.

Receiving Means

The access housing may define receiving means within the housing. The receiving means are configured to receive a dispensing member of the fluid delivery device within the access housing. In one aspect, the receiving means comprises an inner portion within the housing providing a sheath-like area for accommodating a dispensing member, for example a needle, including a needle cover. The receiving means may include the external surrounding areas of the fluid delivery device accessing member. In one aspect the receiving means cooperates with the fluid delivery device accessing member to provide an isolated flow path so that fluid media does not come into direct contact with external surfaces of the dispensing member or its cover. Thus, the receiving means isolates the dispensing means such that its external surfaces remain free and clean from drug product during the preparation of the drug, prior to injection into a patient.

Fluid Delivery Device

The fluid delivery device provides containment of fluid withdrawn from or introduced to the container and/or administrated to a subject. The fluid delivery device component comprises an open first end that may incorporate flange for ergonomic control; a second end with any number of openings for fluid communication, an inner portion providing a sealable, sliding interface and a distal lower housing having an outer portion, which may be adapted to latching/alignment elements for secure attachment and/or positional (configuration) control when mated with the access device housing.

In one aspect the fluid delivery device is a syringe. The syringe comprises at least one access port capable of receiving the fluid delivery device accessing member of the access housing. The access port facilitates drawing fluid in through the bypass fluid channel of the syringe accessing member and delivery of the fluid to the syringe, bypassing the dispensing member. The access port may be a 2-way port, allowing fluid to be transferred from the fluid delivery device to the container. The syringe comprises a plunger having a first end and a second end; a first end which may have gripping means for ergonomic control and a second end that may have any number of extensions. An attachment means is provided proximal to or integrated with the second end for attaching a syringe stopper. The syringe stopper may have any number of contiguous sealing elements about its outer portion perimeter for creating a slidable seal within the syringe barrel. The syringe stopper may be constructed of any of a variety of materials which are biocompatible, sterilizable, and able to withstand exposure to the intended fluid media for the system. These materials preferably are resilient or reasonably deformable and may include, but are not limited to, elastomers such as rubber, silicone and thermoplastic or thermoset elastomers.

Access Port

The access port provides fluid communication between the fluid delivery device accessing member and the fluid delivery device. The access port is preferably re-sealable. In one aspect, the access port is a self-closing, sealable access port positioned at the distal end of the fluid delivery device adjacent the dispensing member such that during transfer and/or mixing, fluid is substantially diverted from traversing the dispensing member. The sealable access port may be comprised of sealing means, a pre-slit septum portion and a thin membrane section, or combinations thereof. In one aspect, the sealable access port is a pre-slit septum extruded with a general parabola shape, a duck-bill shape, or combination of similar geometries, which may be pre-slitted for re-sealable and re-useable access. In one aspect, the access port is a "duckbill" check valve. In another aspect, the access port is a pre-slit septum with a parabola-like extrusion that may further function as a check valve.

In one aspect, the sealable access port comprises or is integral with a deformable membrane. The deformable membrane, as further described herein, provides for substantially fluid-sealed operation and may provide activation of a needle-stick safety mechanism. The access port may be any of a variety of materials which are biocompatible, sterilizable, and able to withstand exposure to the intended fluid media for the system. These materials preferably are resilient or reversibly deformable and may include but are not limited to elastomers such as rubber, silicone and thermoplastic or thermoset elastomers.

Fluid Delivery Device Lower Housing

The lower housing comprises a suspended portion across the inner diameter thereof. The suspended portion comprises a deformable section that provides communication between the fluid delivery device and the needle stick safety mechanism for activation. The suspended portion may be an elastomeric membrane, which may function to maintain a clean, leak-free syringe. The lower housing also may provide for attachment of the fluid delivery device with the access device. In the case of a spring-loaded needle-stick safety protection mechanism, the lower housing may provide a fastening means for a spring and/or catch mechanism. The lower housing preferably does not hinder the fluid path into the fluid delivery device.

The lower housing comprises attachment means allowing for sealable joining to a fluid delivery device, an elastomeric portion to create a hermetic seal upon joining; attachment members for substantial joining of a dispensing member and an opening or set of openings for allowing fluid to pass through the dispensing member and access to the access port of the fluid delivery device.

Fluid Dispensing Member

The fluid dispensing member provides fluid communication between the fluid delivery device and a patient or may be used to access a vial. In one aspect, the fluid dispensing member is a hollow piercing member. The fluid dispensing member is preferably a needle, a blunt cannula, a spray nozzle, a male valved adapter, female valved adapter, a luer connector, or a combination of a luer connector with any of the above fluid dispensing options. In one aspect, the fluid dispensing member is a needle of any size or gauge conventionally used for drug administration. The fluid dispensing member is generally comprised of an open first end and an open second end. In one aspect, the second end is configured such that a sharp, or piercing end is provided. The fluid dispensing member may be constructed of metal or plastic. In one aspect, the fluid dispensing member is of stainless steel.

In one aspect, the dispensing member further consists of a dispensing member cover. The dispensing member cover is constructed to provide needle-stick protection and/or to maintain sterility of the dispensing member prior to use. In one aspect, the dispensing member cover is mechanically sealed with the dispensing member and/or the attachment member(s) of the dispensing member. This sealing relationship prevents air from being aspirated or expelled during fluid preparation. In one aspect, the needle cover is sheathed within the receiving means of the access housing. The needle cover may be constructed from any of a variety of materials which are biocompatible and/or sterilizable.

Needle-Stick Safety Mechanisms

The aforementioned needle cover may provide some level of protection for the user from needle-stick prior to injection into a patient. Another level of needle-stick safety may be implemented to the fluid delivery device. For example, once the device has been used, a needle-stick safety mechanism may passively deploy a covering device or mechanism that covers at least the needle-tip. In another aspect, the needle-stick safety mechanism may be activated by the user to deploy a covering device or mechanism that covers at least the needle-tip and protects the user and others from accidental needle sticks. Additionally, by housing the needle assembly within the vial access device and assembling the device with this needle-stick safety mechanism during manufacturing provides greater safeguards during assembly. Passive needle-stick safety mechanisms may include, but are not limited to, an internal end-of-stroke needle-stick protection release mechanism, defined herein, as well as known needle protection devices, both passive and active (e.g., button, slides, door, etc.).

In one aspect, the needle stick safety mechanism comprises means for the passive deployment of the mechanism at or near the end of the drug delivery stroke of the plunger. In one aspect, the needle stick safety mechanism comprises, at least one protrusion; the at least one protrusion cooperatively coupled to the deformable section of the lower housing to displace a releasable latch in proximity to the distal end of the syringe, releasing the stored energy means. The protrusion may be at the end of a syringe plunger and interact with the corresponding latch means by contacting the deformable section of the lower housing at the end of stroke or when bottomed out in the syringe barrel. Upon full injection of the fluid from within the syringe, and at substantially the end of stroke or when substantially bottomed out in the syringe barrel, the at least one protrusion causes the release of the latch means and deploys the components of the needle stick safety mechanism, sending the needle-tip cover toward the needle tip.

In one aspect, the needle-tip cover comprises latches, in part, that mate with mating latch means (or shelving) within the syringe lower housing or in proximity to the syringe distal end. When a releasing force is applied, the latch arms release stored energy and traverse the needle-tip cover. External force applied directly or indirectly to the latches releases the needle-tip cover of the safety mechanism, which is acted on by stored energy means, sending the needle-tip cover toward the needle tip.

In one aspect, the needle-tip cover component comprises an open inner portion, an outer portion, a first end and a second end; the outer portion having an attachment means for a spring; the first end having one or more latching means. The needle tip cover preferably includes a guide hole for sliding along a needle. When the needle-tip cover guide hole passes the needle-tip, the spring, having been assembled off-center with the needle centerline, moves the needle-tip cover off-center and onto the needle tip. The spring may be of a traditional metal wire form, or be made of any material including, but not limited to an elastomer or plastic, a bellows type, a helical coil with flat ends for mounting, a double helix type, and the like, or may comprise one or more materials.

In one aspect, the needle stick safety mechanism may comprise a torsional member loaded to provide stored energy that is released at the end of the plunger stroke. Torsional members may be, but are not limited to, torsion springs, leaf springs or tension springs coupled such that when the needle-stick safety mechanism is released, the torsional spring or springs will force its coupled members from a collapsed configuration to an extended configuration. Torsional members may be steel forms, plastic forms or elastomeric forms.

Alignment Means

The access device disclosed herein may include positional control and/or alignment control for the fluid delivery device accessing member of the access device to properly mate with the fluid delivery device. For example, rotational camming control may be used, requiring the user to twist the access device to fully seat the fluid delivery device into the activated configuration defined by being able to bypass the needle for aspiration via the fluid accessing member penetrating the access port. In another aspect, locking latches on the syringe barrel and mating latch ledge geometry on the vial access adapter to define the activated and un-activated configurations, requiring the user to actuate the latches in order to move between configurations. In this way, the access port would not be accessed until use. Thus, just prior to use, the user moves the fluid delivery device from an assembled position (pre-accessed position) to the "use" position (access position). The alignment features further may provide for proper alignment of the fluid delivery device accessing member with the access port.

Manufacturing

All of the proposed embodiments can be injection molded with the exception of the needle. Design intent may be such that designs are molded with simple open/close tooling to reduce tool cost and cycle times. The helical, metal spring would not be injection molded, however an elastomeric bellows-type spring may be. Many of the clip designs are molded with simple open/close tooling in mind to reduce tool cost and cycle times. Where feature definition may not be able to be achieved by single tool molding; ultrasonic welding, adhesives or mechanical retention may be employed to join components. Furthermore, where dissimilar materials may be advantageous (i.e. the syringe septum portion), a 2-shot molding technique may be utilized. For embodiments that may use a capping means as described herein, it may be coupled such that it seals accordingly, but may also be removed without significant force. Adhesives may be required to substantially join components, particularly in the case of designing for interface with an off-the-shelf syringe. Adhesives may be employed to substantially join components, particularly attachments that may be coupled with luer connections, where applicable. Adhesives may be but are not limited to: cyanoacrylate, 2-part epoxy, heat-activated resin, UV cured adhesive and hot melt. Joining may also be achieved through, but not limited to, the use of a solvent bonding, ultrasonic welding, and/or heat-staking means.

Use of the Vial Access Device

In the foregoing, the fluid delivery device is represented by a syringe, however, any fluid delivery device may be used. The exemplary combination consists of a needled syringe assembly and a vial access device that reversibly receives and seals to the syringe at one end. The vial access device reversibly receives a drug vial at another end. Optionally, retention means for securely attaching the vial and/or the syringe to the vial access device are used. Such means may provide audio, visual, or tactile indications upon correct assembly. Optionally, one or more removal tabs, as defined herein, may be included on the vial access device to facilitate removal and/or attachment of vials in sequence. Upon assembly, the combination establishes a fluid flow path that provides fluid communication between the syringe and the vial. Fluid communication between the syringe and the vial bypasses the needle or dispensing means of the syringe. For example, the vial access device accommodates needle or other dispensing means of the syringe such that, within the adapter, it is sheathed and/or isolated from fluid communication between the syringe and the vial. In one aspect, fluid communication between the syringe and the vial comprises a fluid path bypass.

In one aspect, the combination, with the syringe and vial sealably connected to the vial access device, allow for two configurations of activation: an un-activated configuration in which fluid transfer from the vial is prevented or substantially eliminated and/or an activated configuration where the needle of the syringe is bypassed. Bypass of the needle is via a secondary fluid passageway, allowing higher flow by virtue of a larger diameter conduit than that of the syringe needle. Bypass is achieved by an accessing member with an isolated flowpath internal to the vial access device. Upon activating the system, the accessing member pierces a pre-slit septum positioned in proximity to the needle of the syringe that leads directly to the interior of the syringe barrel.

After the syringe assembly is filled, it may be removed from the vial access device. The pre-slit septum of the syringe self-closes upon detachment. A needle cover may also be housed within the vial access adapter and assembled about the needle to prevents air from being aspirated or expelled during fluid preparation, as well as for safe and clean transport. Once the needle cover is removed it may then be used for injectable drug delivery via the needle.

In another aspect, the combination comprising a syringe, needle cover, vial and vial access device may allow for three positional configurations:

1. A locked configuration in which the syringe and the vial access device are prevented or inhibited from translating axially with respect to one another, but may be allowed to rotate with respect to one another. A positional lock may be employed to prevent unintended rotation until a reasonable or pre-set torque has been applied. The lock may be in the form of, but not limited to, an interference fit, snap-fit or the like.
2. A pre-access configuration in which fluid transfer from the vial is prevented or inhibited, but axial translation may be allowed.
3. A bypass access configuration where fluid communication between the accessed vial and the syringe is permitted. This may be achieved via interconnected internal conduits within the vial access device, which may either be terminated in a spike or blunted-type syringe accessing member having at least one fluid lumen. The accessing member may pass through a piercable septum adjacent the dispensing member which may be, but is not limited to, a pre-slit septum. A snap-fit latch arrangement, such as a lock/release tab providing a tactile feedback when access has been achieved through the septum may be used. The latch can be configured such that upon pressing, the syringe is released from the vial access device.

After the vial access device is employed and the syringe contains the liquid or reconstituted material of the vial, the combination comprising a syringe, needle cover, and needle stick safety mechanism may allow for two operational configurations:

1. A transport configuration wherein a filled syringe is removed from a vial access device. A needle cover may be used to prevent contamination and protect from unintended needle-stick.
2. A post-injection safety configuration wherein an attached needle-stick safety mechanism is passively or manually deployed as described herein.

The method of using the vial access device as described greatly reduces the number of steps typically associated with access, preparation, and administration of drugs. Additionally, the prescribed configurations as detailed here, assure optimal preparation and delivery of a drug as waste can be reduced by the design of the vial access spike; mechanical breakdown of the drug products can be avoided by high flow fluid paths; time and complexity is reduced by elimination of steps to the user and by housing a needle or other dispensing means within the assembly.

Referring now to the drawings, various illustrative embodiments will be described. FIG. 1: is a perspective view of a first embodiment of the vial access and injection combination. Syringe (101) is sealably coupled to vial access device (102) comprising container accessing member (103) and a plurality of attachment means (104) and a plurality of guide tabs (110) concentric about the container accessing member. Opposing attachment means consist of locking means (105). The attachment means may also comprise tabs (106) extending from the attachment means end. Gripping means (107) are shown proximal to tabs (106). Syringe (101) comprises barrel (108) and plunger rod (109).

Figure 2:
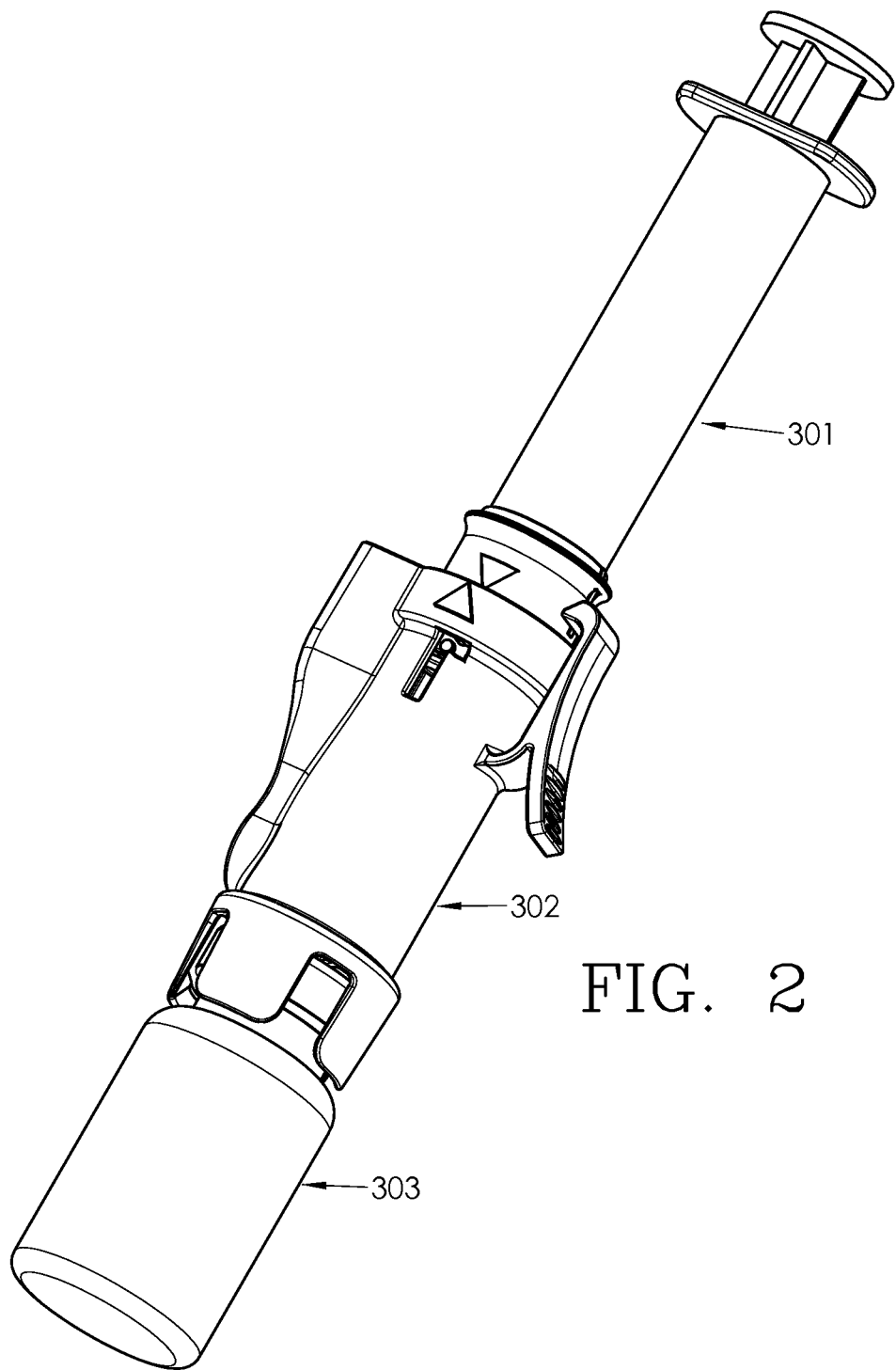
FIG. 2 is a perspective view of a combination vial access device, fluid delivery device and vial embodiment shown in a pre-access, unlocked configuration.
Figure 3:
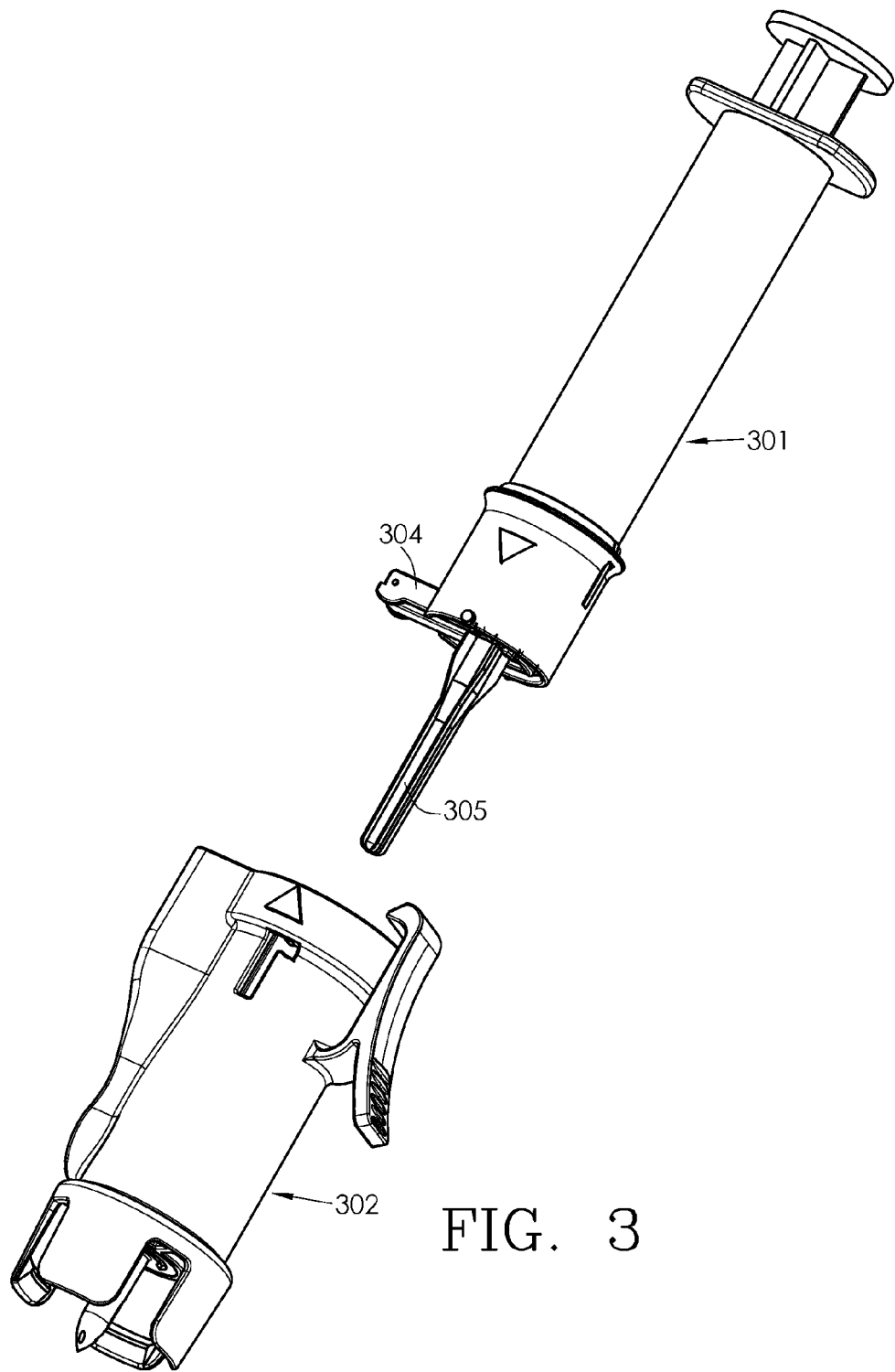
FIG. 3 is an exploded, perspective view of a combination vial access device and fluid delivery device embodiment.

FIG. 2 is a perspective view of a combination vial access and injection system shown in a pre-accessed configuration. Syringe (301) is sealably coupled to a vial access device (302) which is securably attached to vial (303). FIG. 3 is an exploded view of vial access device (302) showing needle cover (305) and needle-stick safety mechanism (304).

Figure 4:
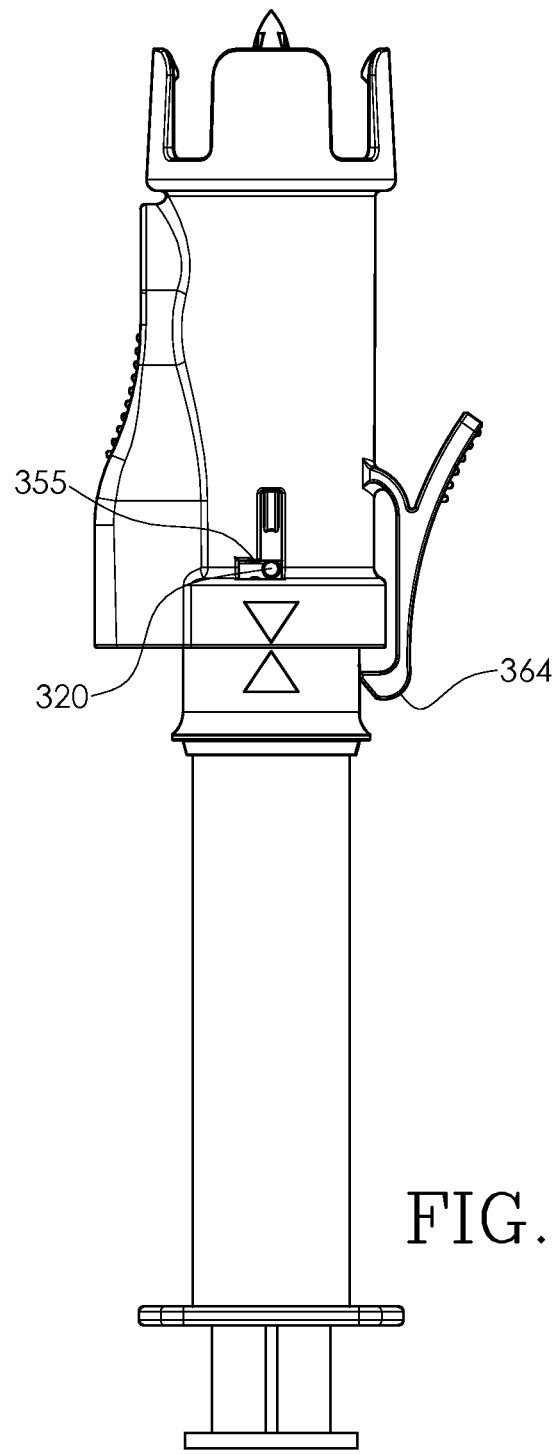
FIG. 4 is a profile view of a combination vial access device and fluid delivery device embodiment shown in a pre-access, unlocked configuration.

FIG. 4 is a profile view of the combination of syringe and vial access device shown rotated to a pre-access configuration. Syringe element alignment means (320) have been driven past rotational hold means (355) on the vial access device. Clip (364) provides secure coupling of vial access device and syringe and prevents axial movement thereof.

Figure 5:
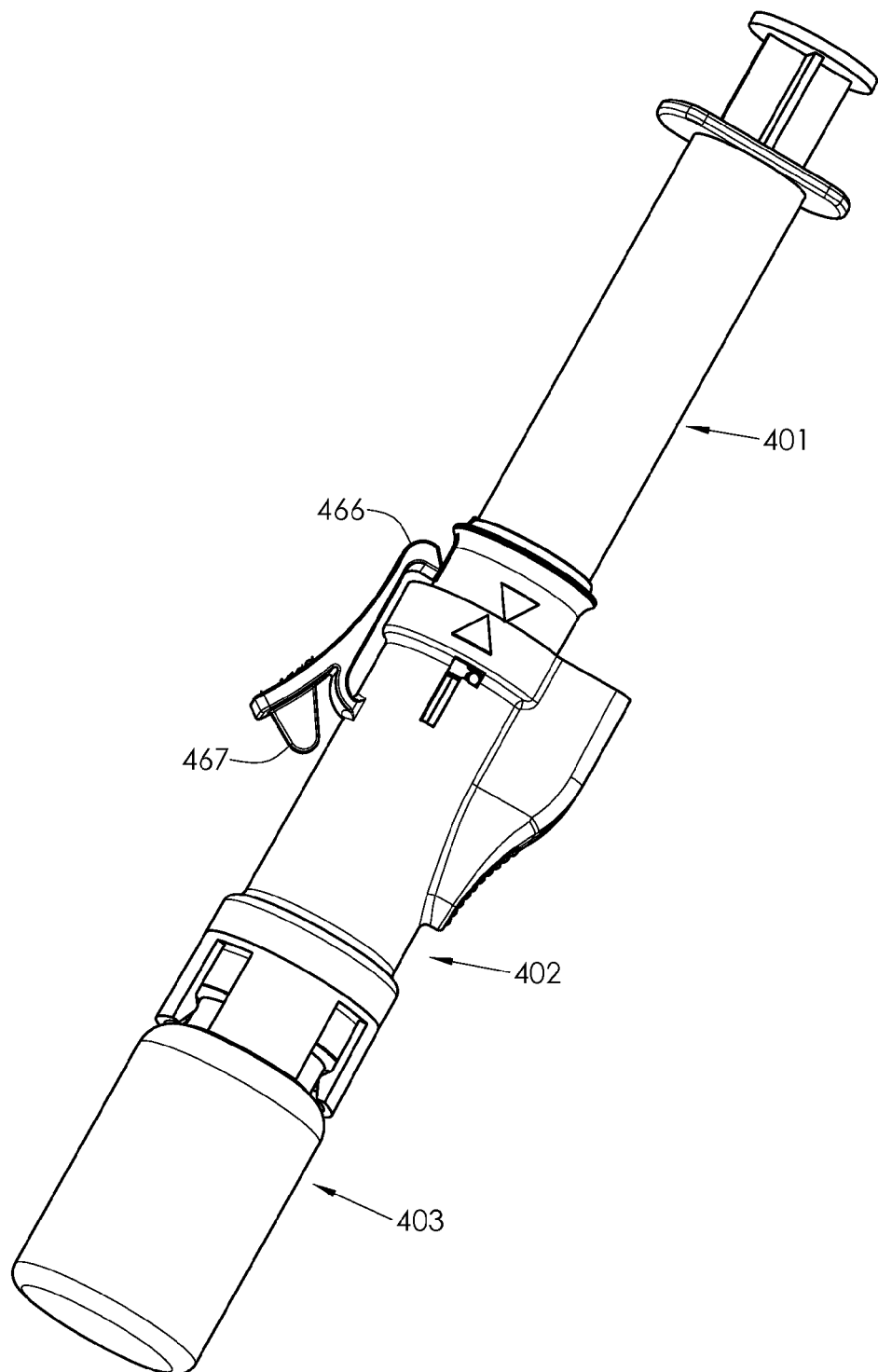
FIG. 5 a perspective view of a combination vial access device, fluid delivery device and vial embodiment shown in a pre-access, locked configuration.
Figure 6:
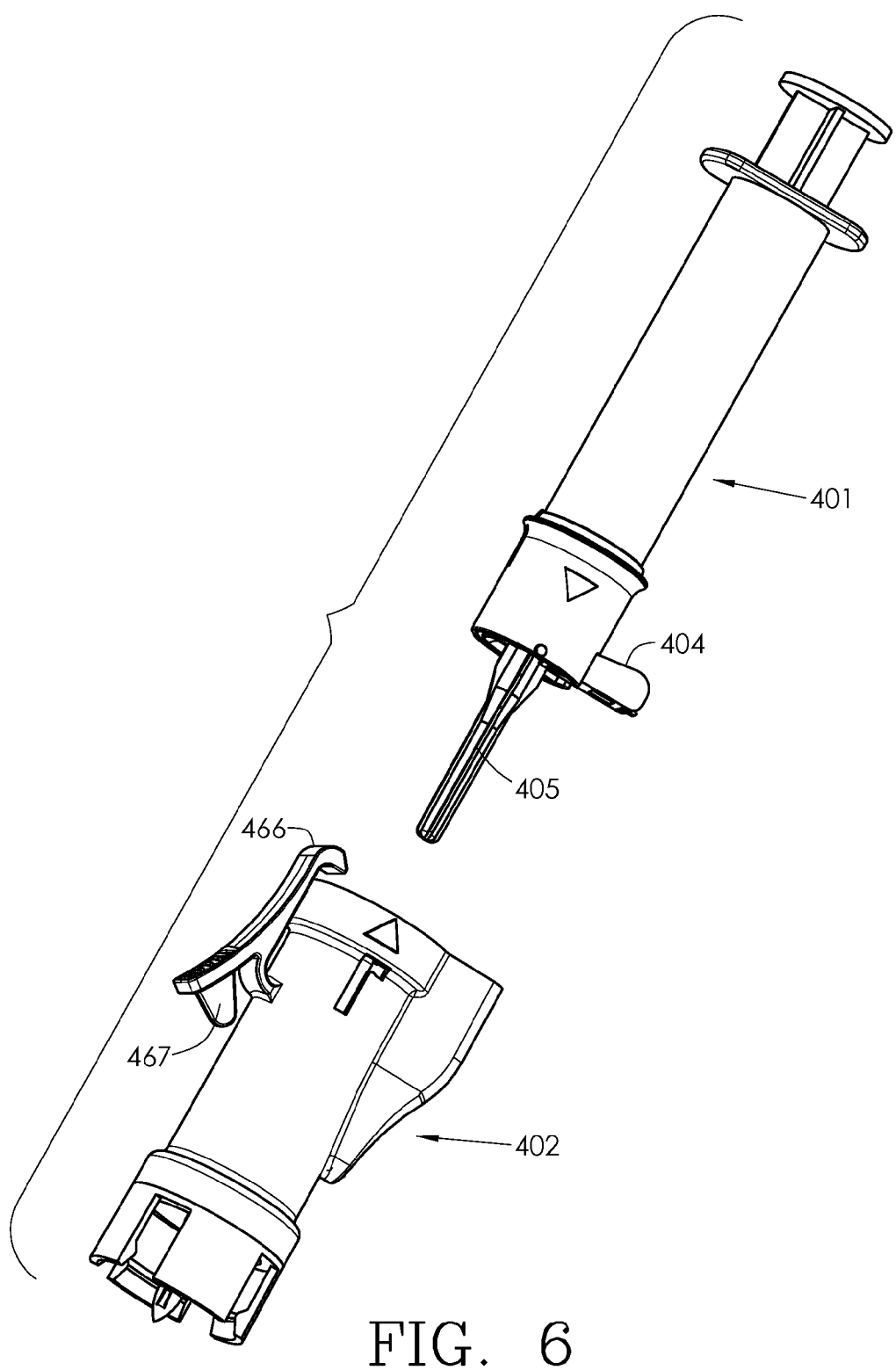
FIG. 6 is an exploded, perspective view of a combination vial access device and fluid delivery device embodiment.

FIG. 5 is a perspective view of a second aspect of a vial access and injection system depicted in a locked configuration. Syringe (401) is coupled to a vial access device (402), which is securably attached to vial (403). Clip (466) includes tab (467) to prevent overextension. FIG. 6 is an exploded view of FIG. 5 without the vial, depicting vial access device (402), needle cover (405) and needle-stick safety mechanism (404) of the combination shown in FIG. 5.

Figure 7:
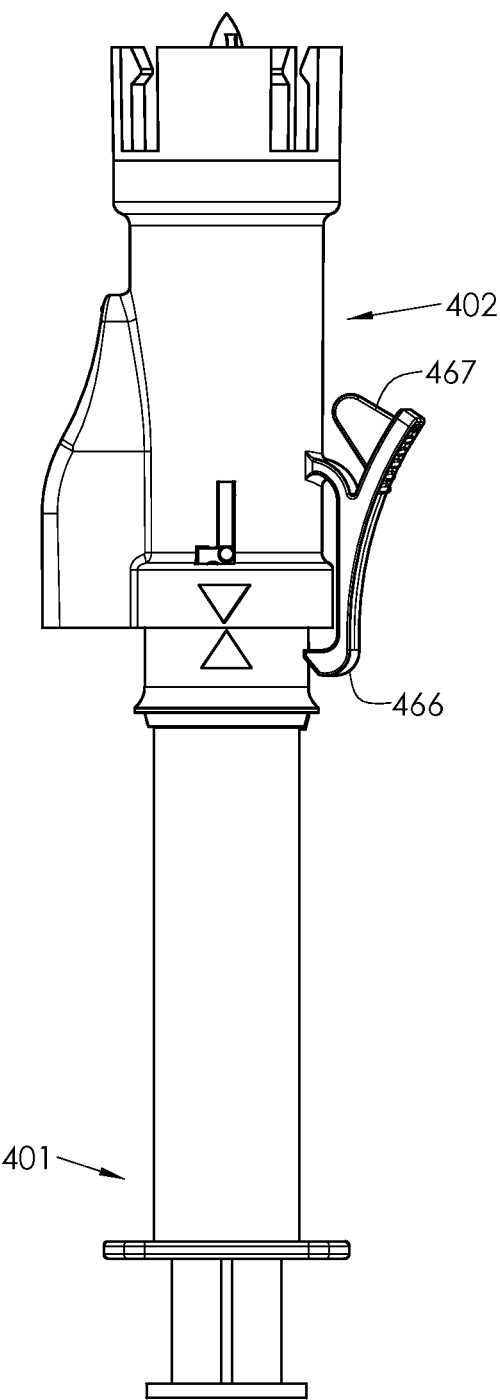
FIG. 7 is a profile view of a combination vial access device and fluid delivery device embodiment shown in a pre-access, unlocked configuration.

FIG. 7 is a profile view of the combination shown in FIG. 4 in a pre-access configuration.

Figure 8:
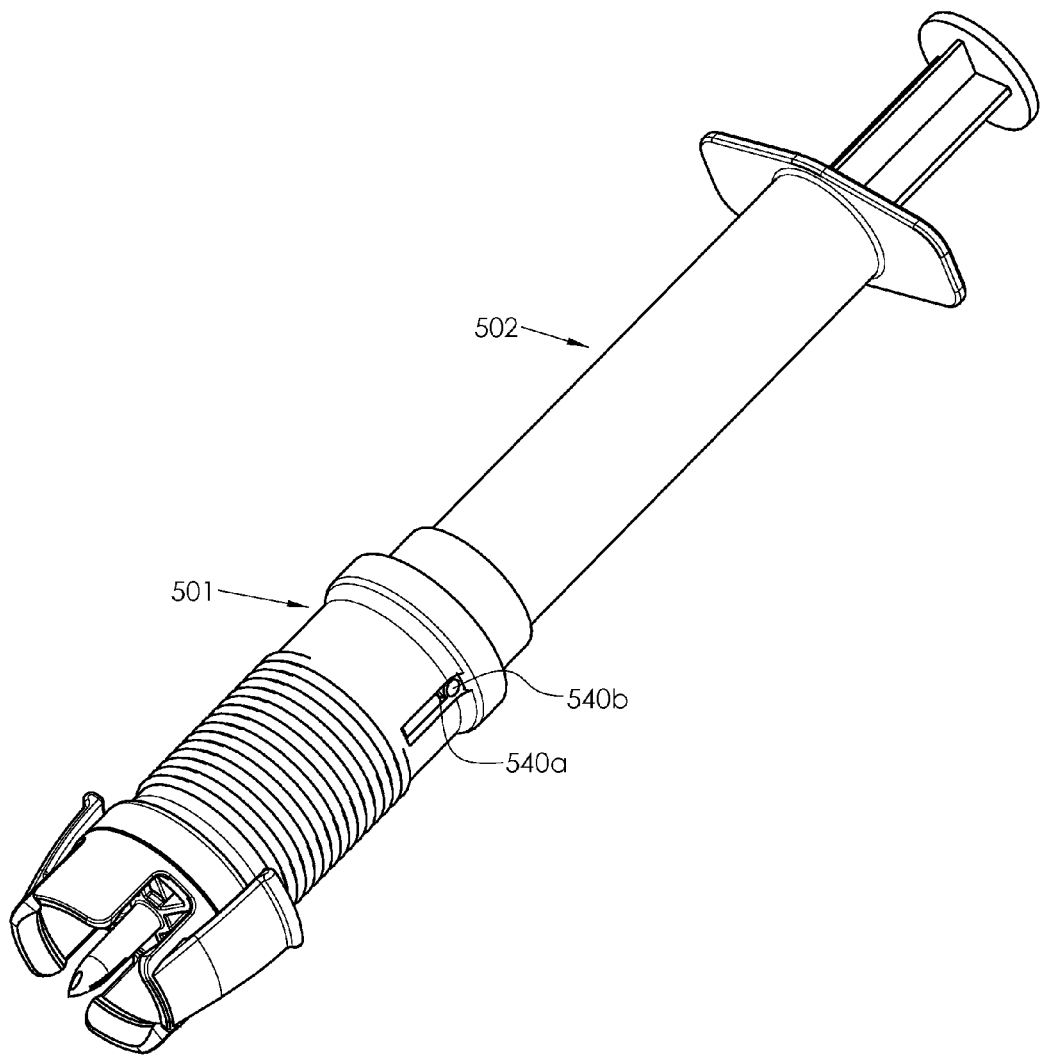
FIG. 8 is a perspective view of a combination vial access device and fluid delivery device embodiment shown in a pre-access configuration.
Figure 9:
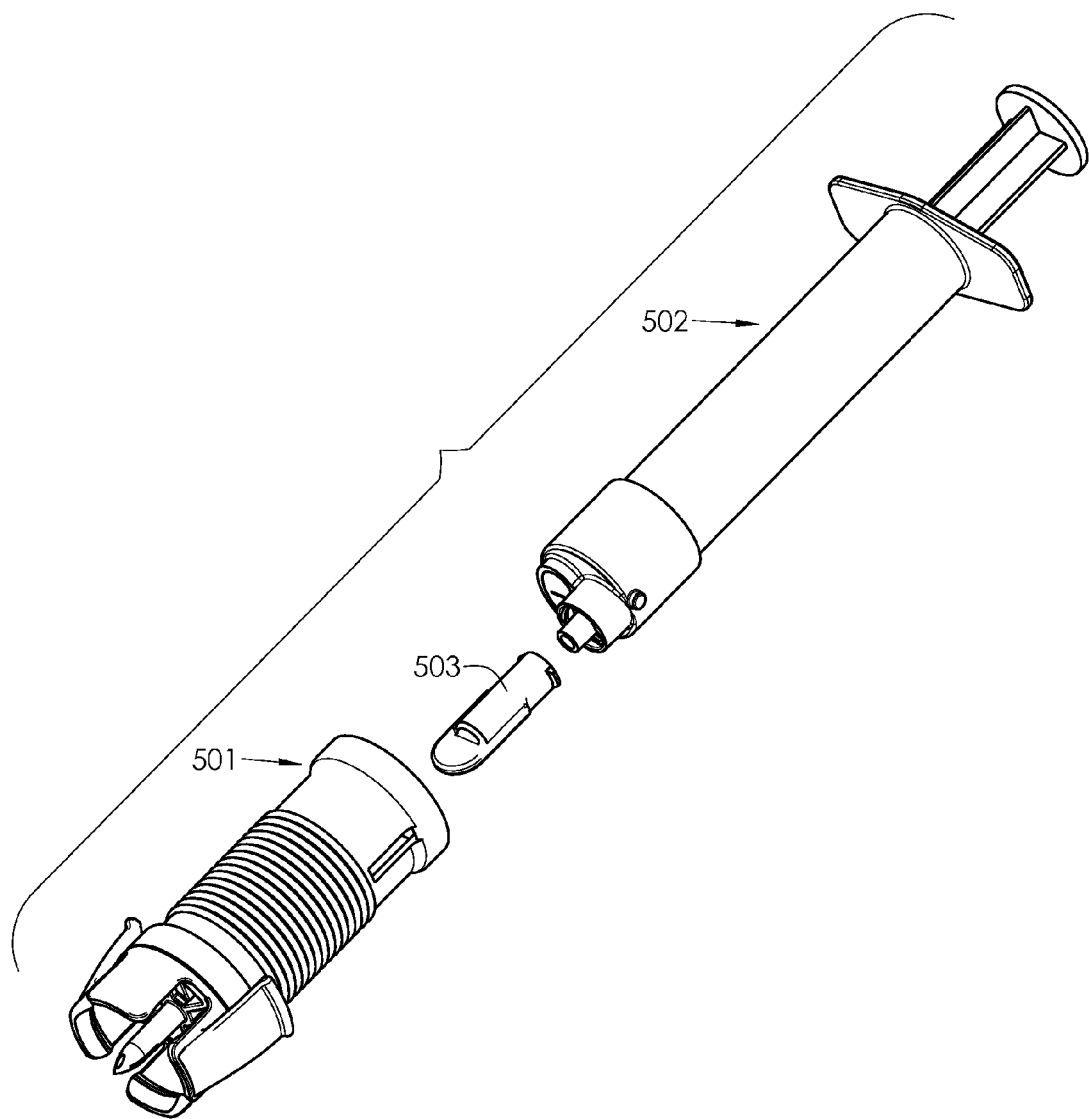
FIG. 9 is an exploded, perspective view of a combination vial access device and fluid delivery device embodiment.
Figure 10:
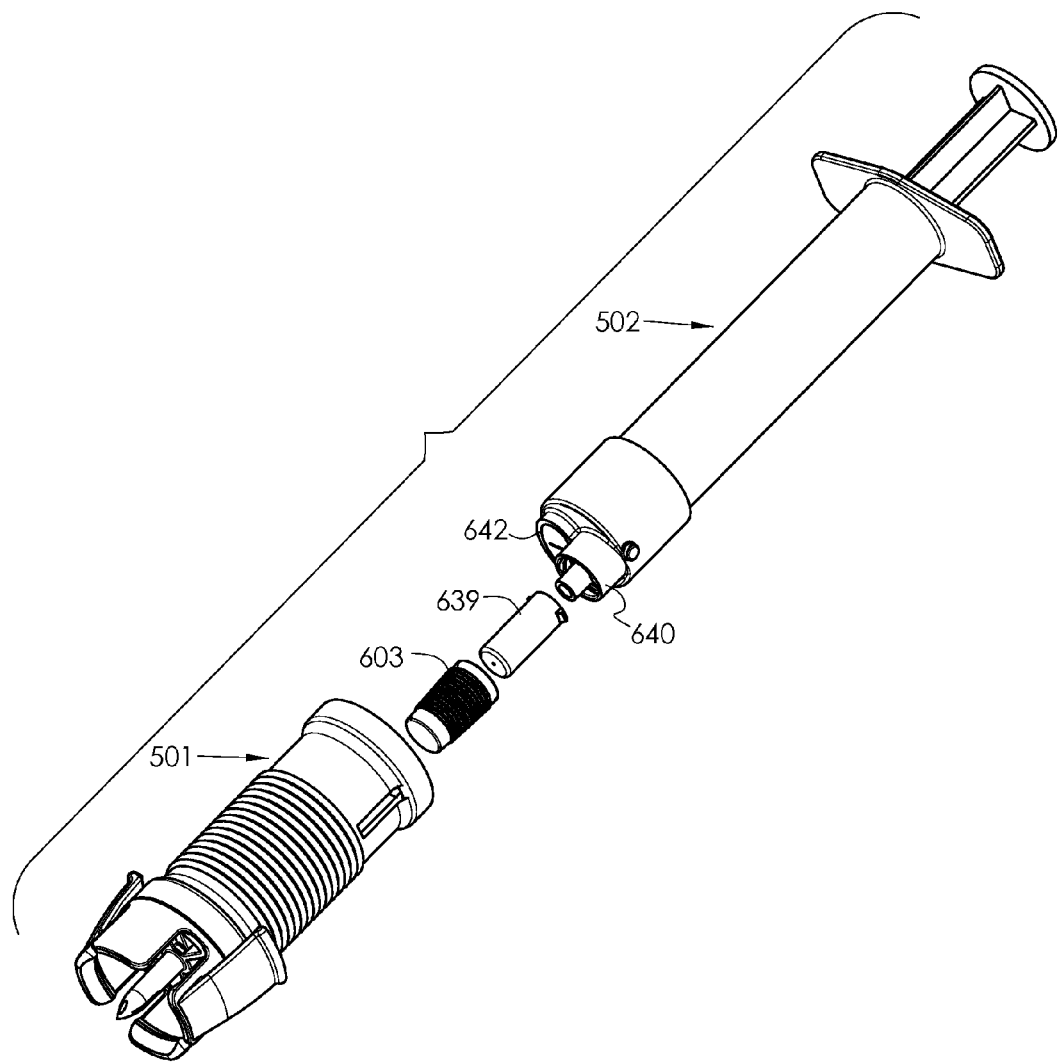
FIG. 10 is an exploded, perspective view of a combination vial access device and fluid delivery device embodiment.

FIG. 8 is a perspective view of a combination vial access and fluid delivery device embodiment depicting vial access device (501) and syringe (502) and alignment means (540*a*), (540*b*). FIG. 9 is an exploded, perspective view of FIG. 8 showing syringe (502), vial access device (501) and luer cap (503). FIG. 10 is an exploded perspective view of vial access and injection system including spray nozzle (639) as dispensing member sealably secured to luer (640) adjacent access port (642) of syringe (502), and cap (603).

Figure 11:
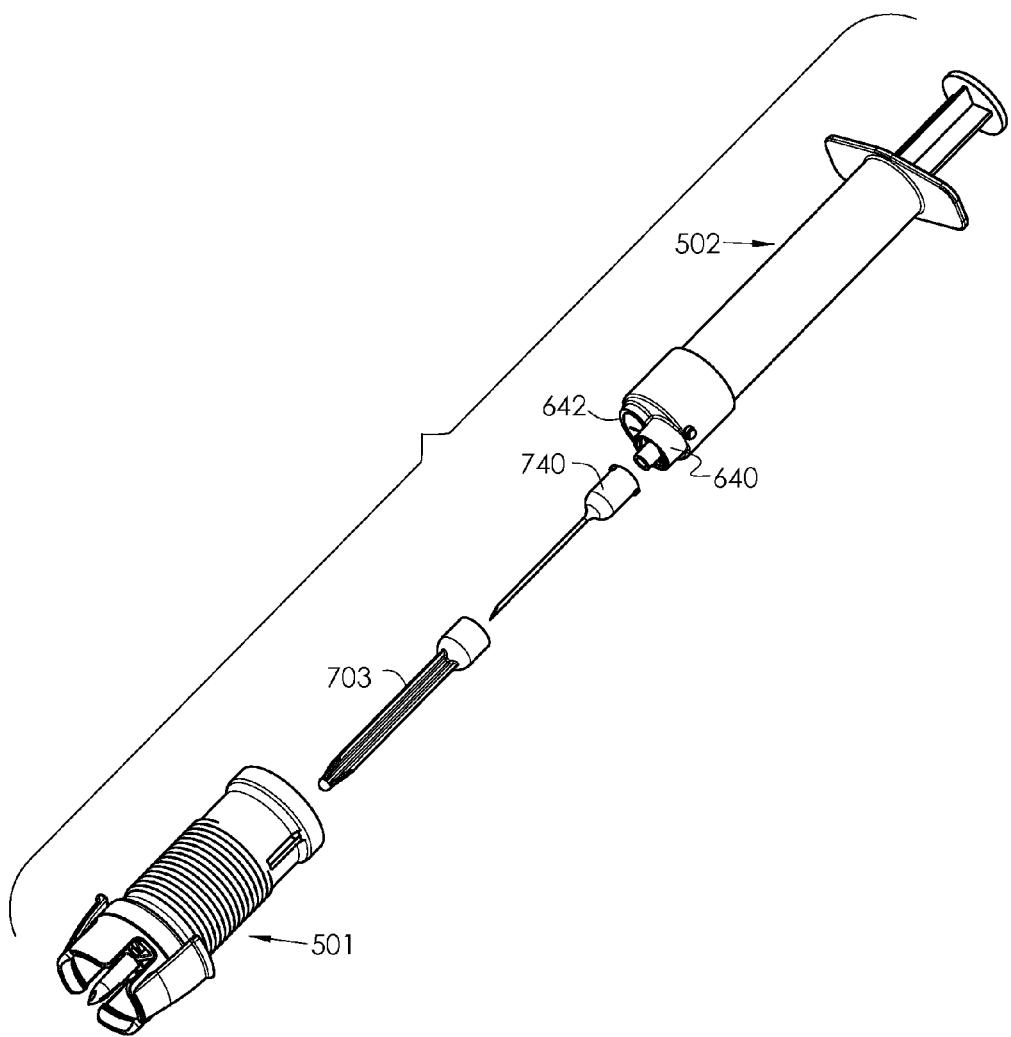
FIG. 11 is an exploded, perspective view of a combination vial access device and fluid delivery device embodiment.
Figure 12:
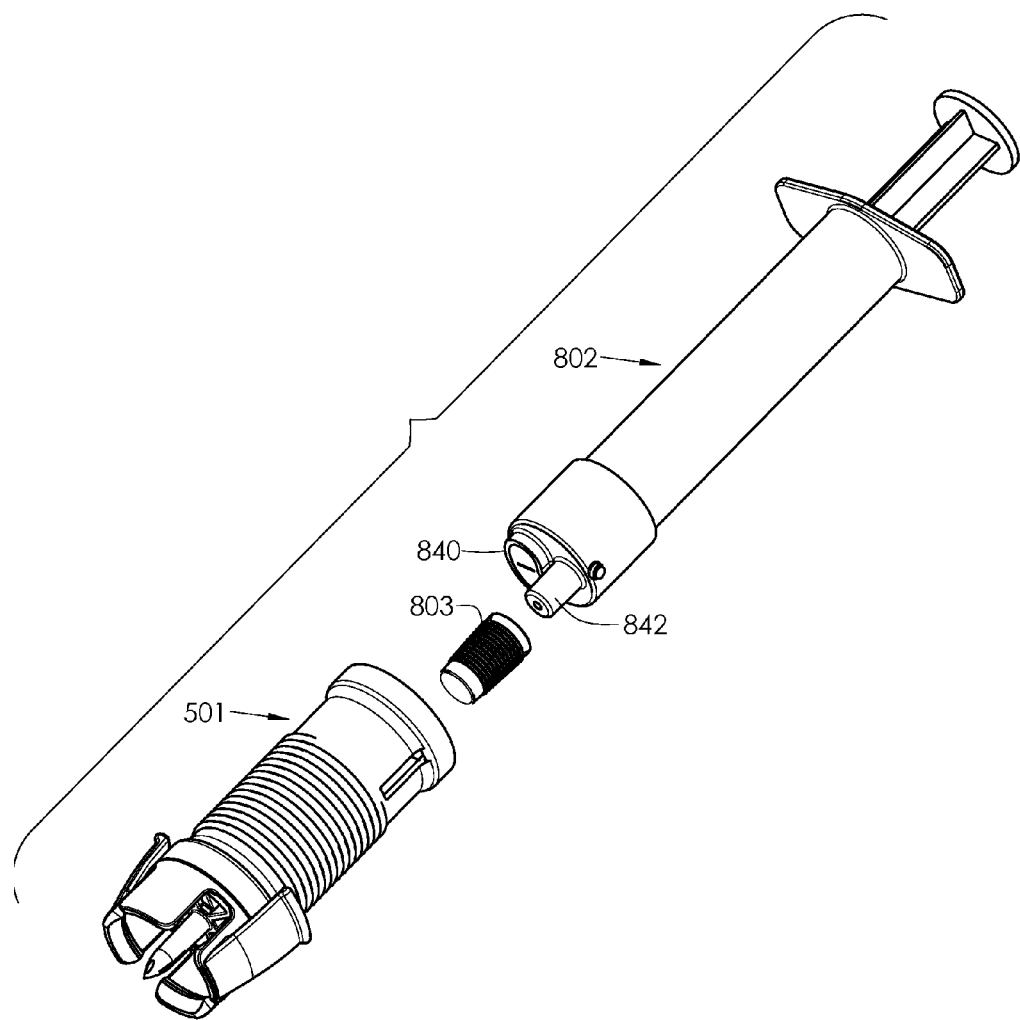
FIG. 12 is an exploded, perspective view of a combination vial access device and fluid delivery device embodiment.

FIG. 11 is an exploded perspective view of a combination a vial access and fluid delivery device embodiment showing hollow needle (740) dispensing member sealably secured to luer (640) of syringe (502) adjacent access port (642), and cap (703). FIG. 12 is an exploded, perspective view of a combination vial access and fluid delivery device embodiment depicting vial access device (501), syringe (802) with integrated spray nozzle dispensing member (842) positioned adjacent access port (840), shown with cap (803).

Figure 13:
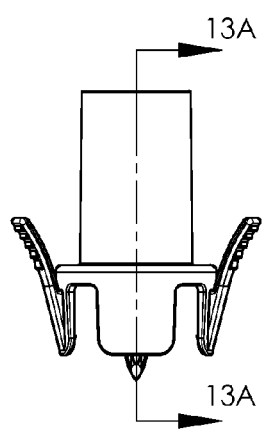
FIGS. 13-13A are sectional plane and cross-sectional views of a vial access device embodiment.
Figure 13A:
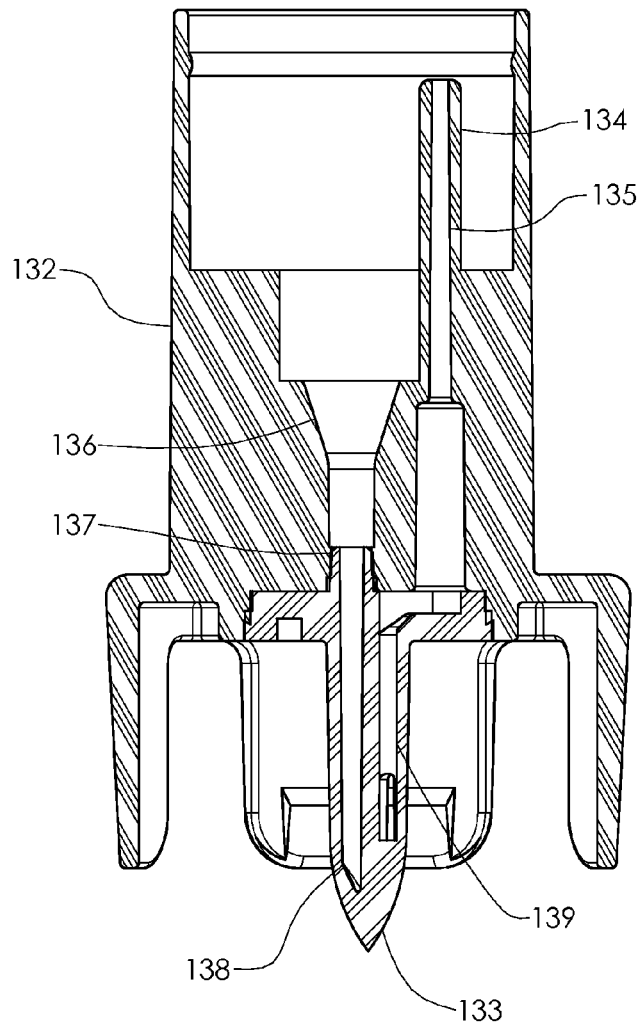
Figures 16, 16A:
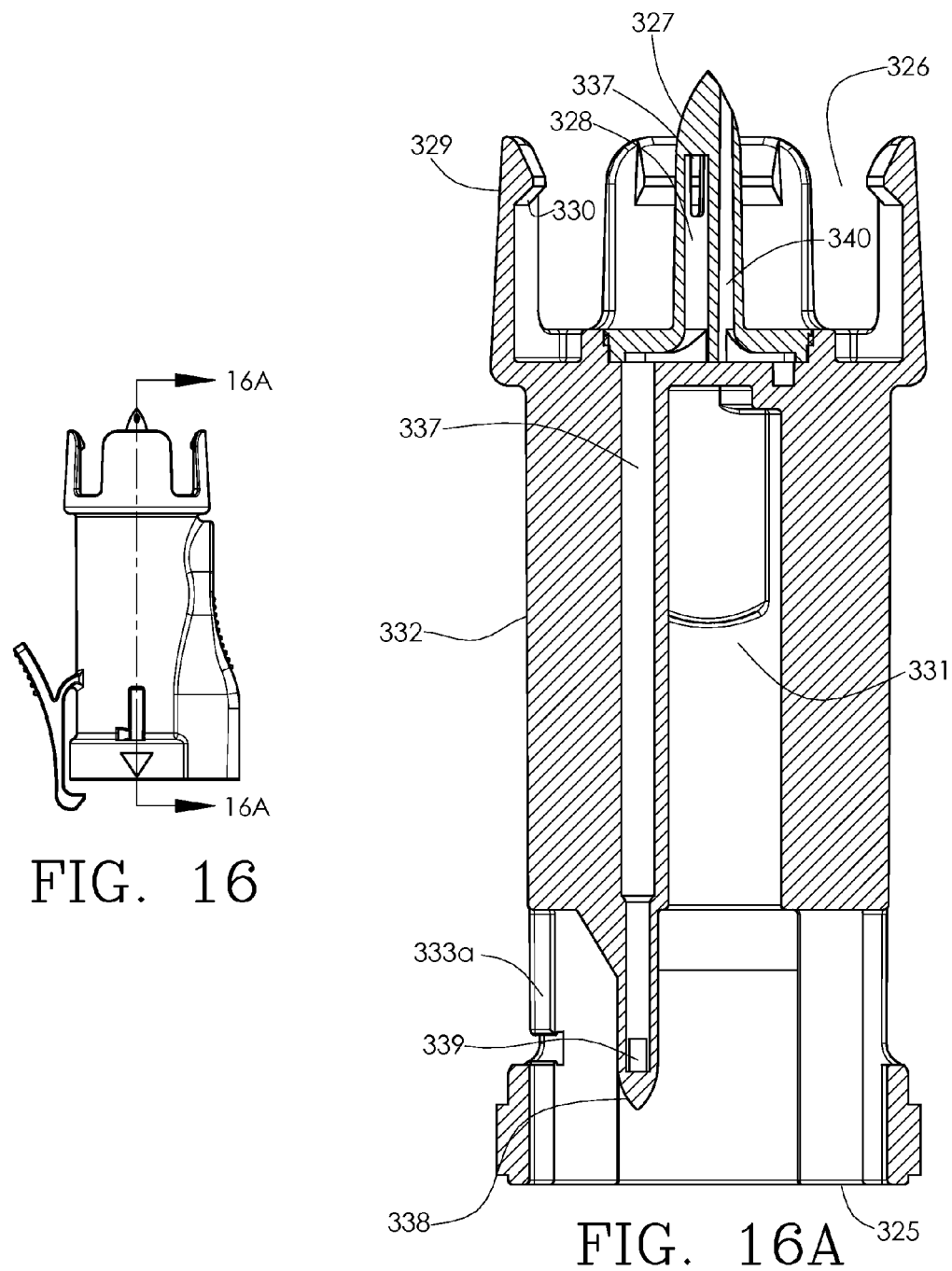
FIGS. 16-16A and 17-17A are sectional plane and cross-sectional views, respectively, of a vial access device embodiment.
Figure 17:
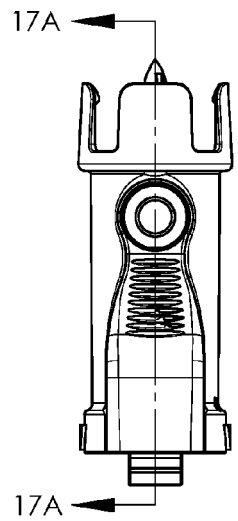
Figure 17A:
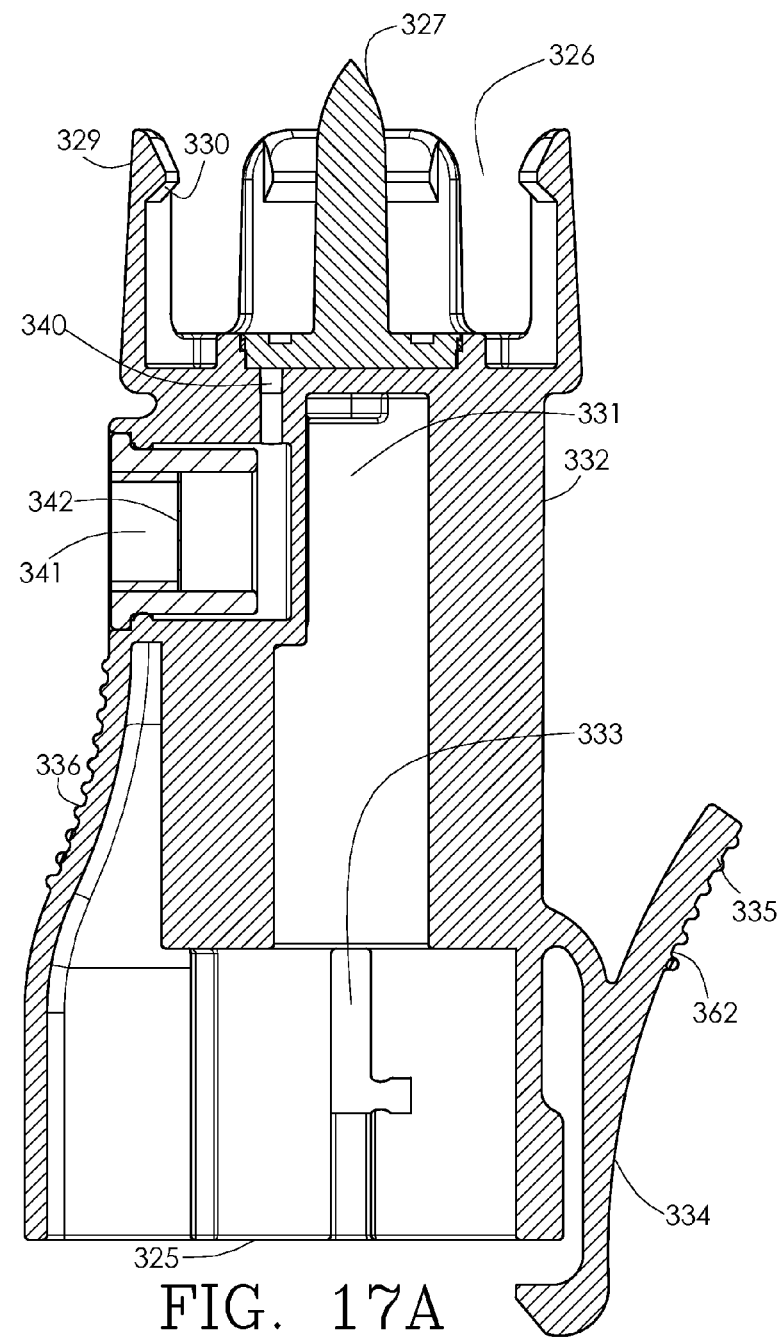
Figures 18, 18A:
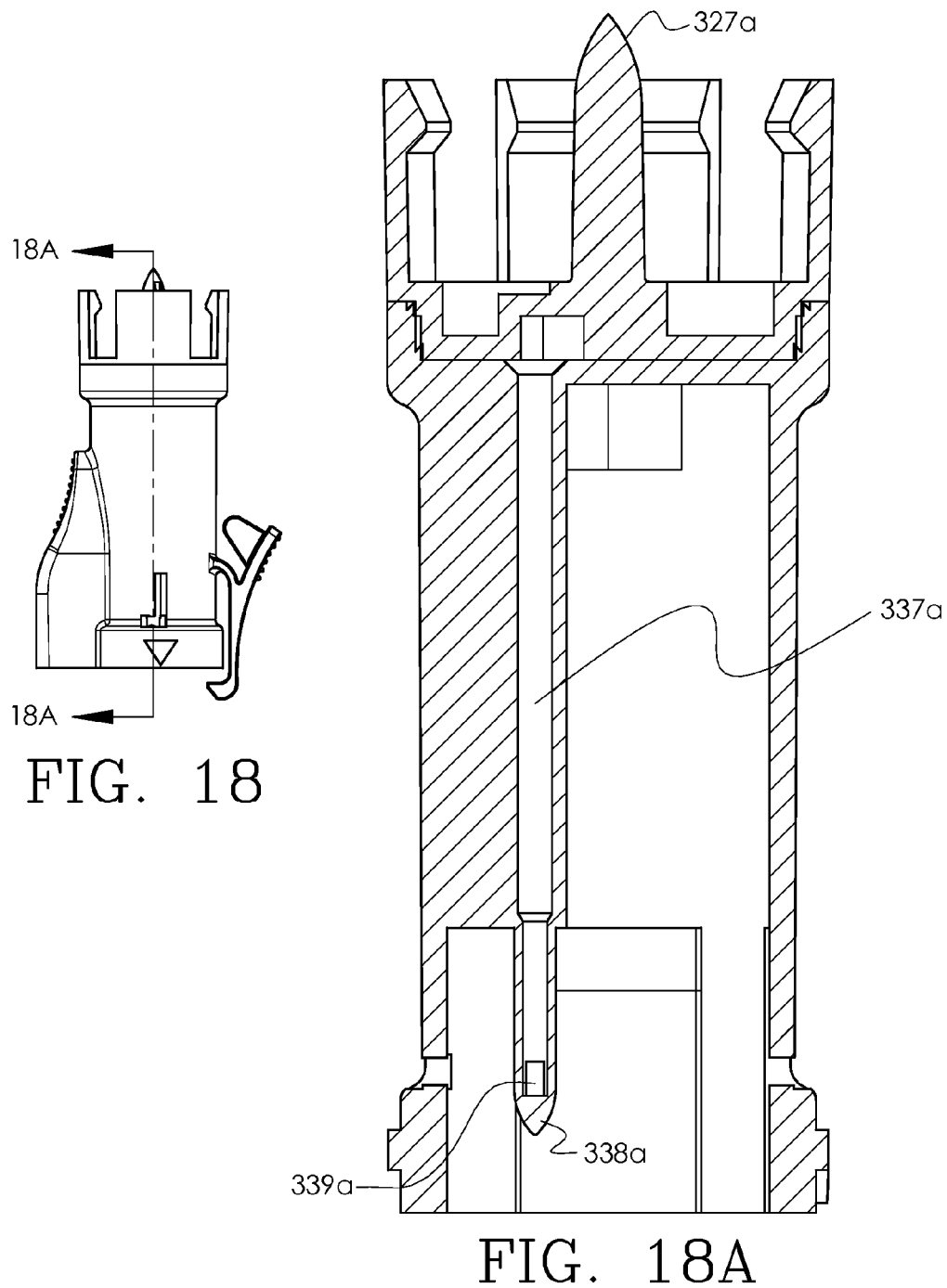
Figures 20, 20A:
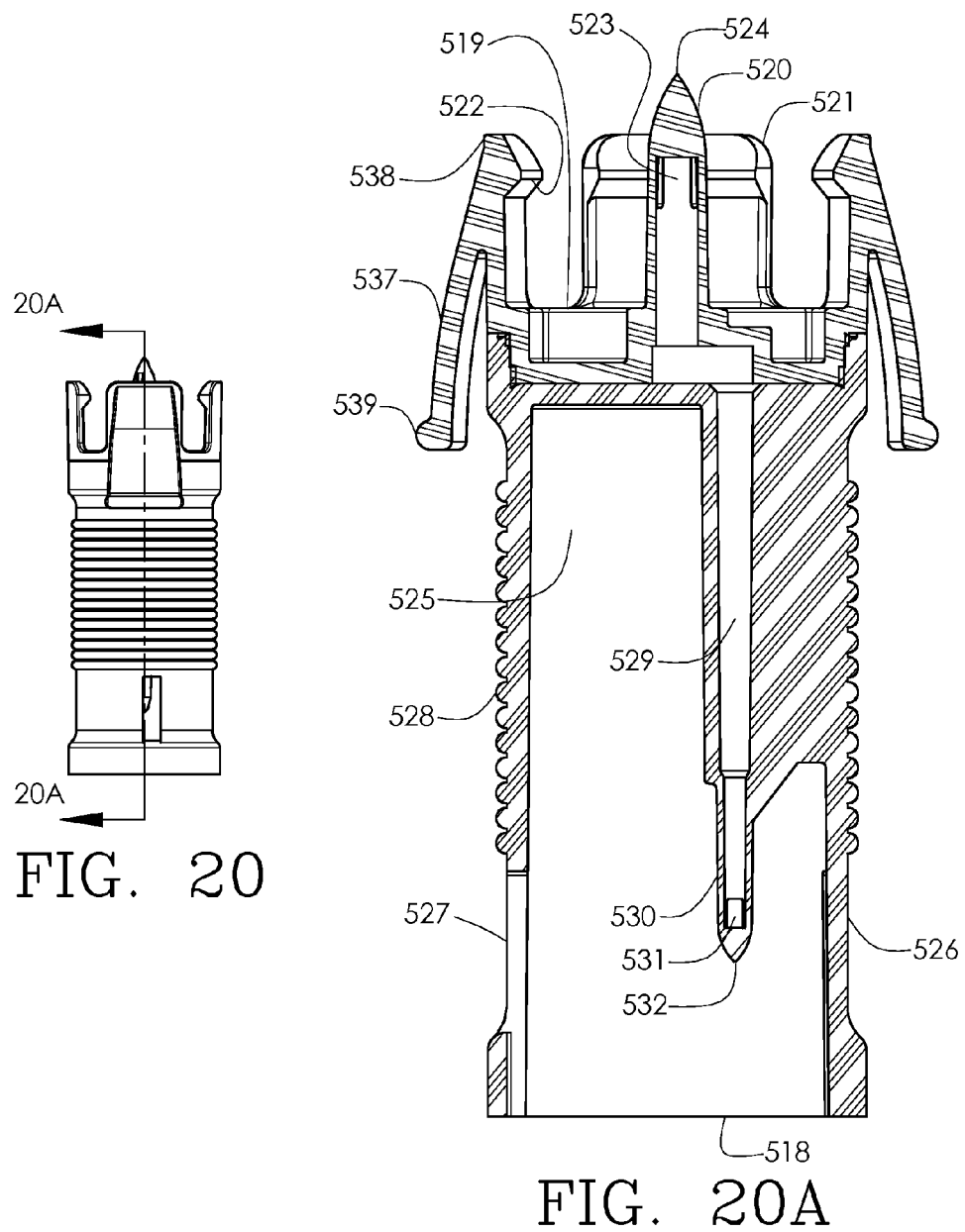
FIGS. 20-20A are sectional plane and cross-sectional views of a vial access device embodiment.
Figure 21:
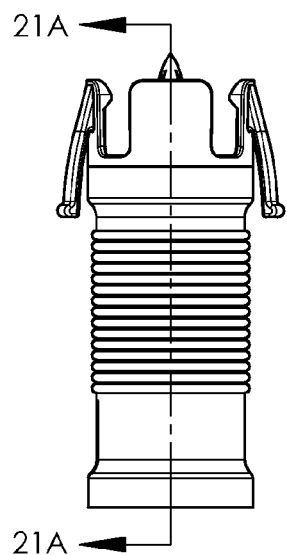
FIGS. 21-21A are sectional plane and cross-sectional views of a vial access device embodiment.
Figure 21A:
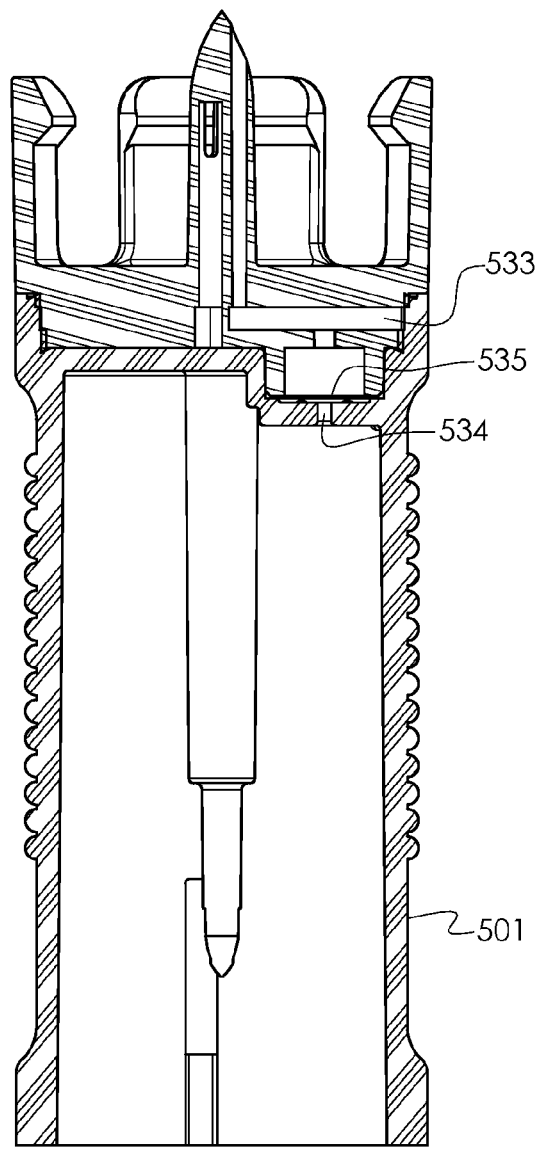

FIG. 13 is a cross-sectional representation of an access device embodiment. The access device comprises housing (132) and container accessing member (133). The housing comprises a vial attachment portion as previously described, fluid delivery device accessing member (134) with fluid conduit (135), receiving means (136) parallel to the central axis and joining geometry (137) for joining the housing to the container accessing member. The accessing member comprises a spike-like shape with an internal lumen (138) for receiving a dispensing member and fluid lumen (139) such that, when assembled with the housing, internal lumen (138) is aligned and sealed with receiving means (136) and fluid lumen (139) is in fluid communication with the fluid conduit (135). As shown, fluid conduit (135) may be larger in cross-sectional area than the dispensing member.

FIGS. 14-14A are sectional plane and cross-sectional views, respectively of an access device having venting means. Vent lumen (143) is in fluid communication with the fluid delivery device accessing member (144). Vent filter (145) is positioned in fluid communication with the vent lumen. FIG. 15-15A is a cross-sectional view of an aspect of an access device showing alternate venting configuration. Vent lumen (243) vents into the receiving means of the housing. Vent filter (245) is positioned in fluid communication with the vent lumen.

FIGS. 16-16A and 17-17A are sectional plane and cross-sectional views of an access device embodiment showing receiving means for receiving a needle-stick safety mechanism and dispensing member of a fluid delivery device. The vial access device comprises an open first end (325) and open second end (326) terminating in container accessing member (327) having at least one fluid lumen (328). The second end having a plurality of attachment means (329) comprising locking means (330) for attachment to a vial, receiving means (331), housing (332) having orientation means (333*a*), proximal to the open first end, and c (334) with gripping means (335) for ergonomic control. The clip includes finger pad portion (362) which allows for the clip to move in an arc-like motion to release the connected syringe, and an external portion which includes gripping means (335) for ergonomic control. Interconnecting conduit (337) fluidly connects container accessing member (327) and fluid delivery device accessing member (338). Fluid delivery device accessing member (338) has at least one opening (339) proximal to the distal end. Access device has vent conduit (340) opening proximal to the container accessing member's terminating end and fluidly connecting at least one opening (341) to the ambient surrounding the vial access device for venting. Vent conduit (340) includes filter (342). FIGS. 18-18A and 19-19A are sectional plane and cross-sectional views of an access device depicting venting internal to the access device. Filter (442) is positioned within vent (469). Interconnecting conduit (337*a*) fluidly connects container accessing member (327*a*) and fluid delivery device accessing member (338*a*). Fluid delivery device accessing member (338*a*) has at least one opening (339*a*) proximal to the distal end. Access device has vent conduit (340a) opening proximal to the container accessing member's terminating end and fluidly connecting at least one opening (341a) within the housing. Vent conduit (340a) includes filter (342a). Also shown is protrusion (463) integrated with clip (434) for preventing over-stressing when force is applied to finger pad (462) area.

FIGS. 20-20A and 21-21A are sectional plane and cross-sectional views of an access device depicting open first end (518), second end (519) having attachment means (521) with corresponding locking means (522) for attachment to a vial or container. Access device has container accessing member (520) extending generally outward from second end, the accessing member having at least one lumen (523) open proximal to accessing member distal end (524). Receiving means (525) is positioned inside the housing. Access device external portion (526) has alignment means (527) proximal to the open first end and gripping means (528) for ergonomic control. Interconnected fluid conduit (529) provides fluid communication between the container accessing member distal end and fluid delivery device accessing member (530), shown shaped as a spike or blunted cannula. Fluid delivery device accessing member has at least one opening (531) proximal to distal end (532). Tabs (537) having gripping means (539) extending proximal to attachment means distal end (538) for removing an attached container or vial from the access device. Vent conduit (533) opens proximal to container accessing member terminating end and terminates at vent opening (534) to the ambient surrounding the vial access device. Vent conduit (533) includes filter (535). The vent conduit may optionally contain a check valve, for example, a one-way check valve, such as a "top hat," "double duck bill," "umbrella," "flat disc," and the like.

Figure 22:
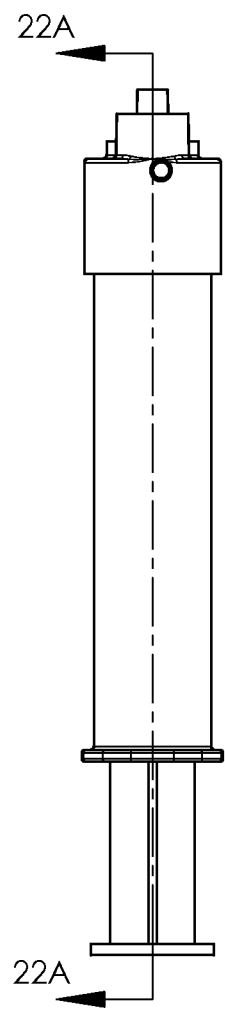
FIGS. 22-22A are sectional plane and cross-sectional views of a syringe embodiment
Figure 22A:
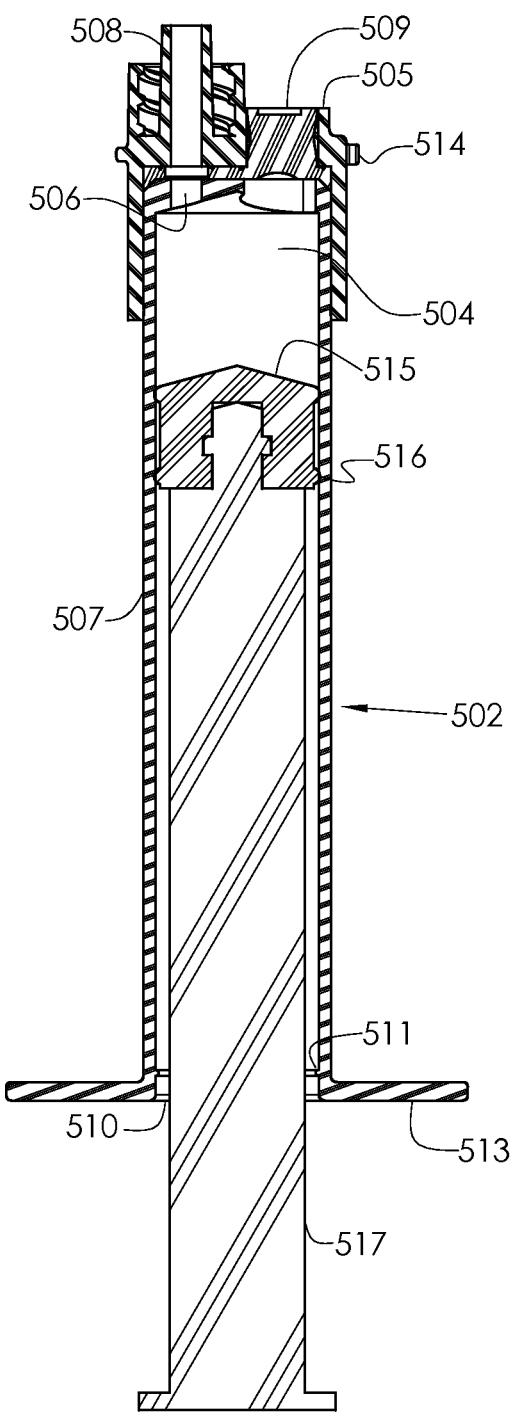

FIG. 22-22A are sectional plane and a cross-sectional views of syringe (502) showing closed first end (505), dispensing means (506), allowing fluid communication between the syringe and its exterior, luer connection (508), access port (509), an open second end (510) having proximally located plunger retaining means (511), an exterior portion having protruding flange means (513) located proximal to the second end, and alignment means (514) located proximal to the first end. Stopper (515) having slidable sealing rings (516) is coupled to plunger rod (517). The access port may be configured of any access type, which may include, but is not limited to, pre-slit or otherwise piercable members. The luer connection may be of the locking type or non-locking type.

Figure 23:
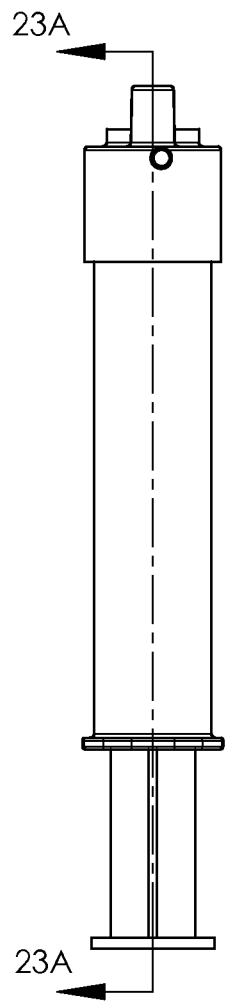
FIGS. 23-23A are sectional plane and cross-sectional views of a syringe embodiment
Figure 23A:
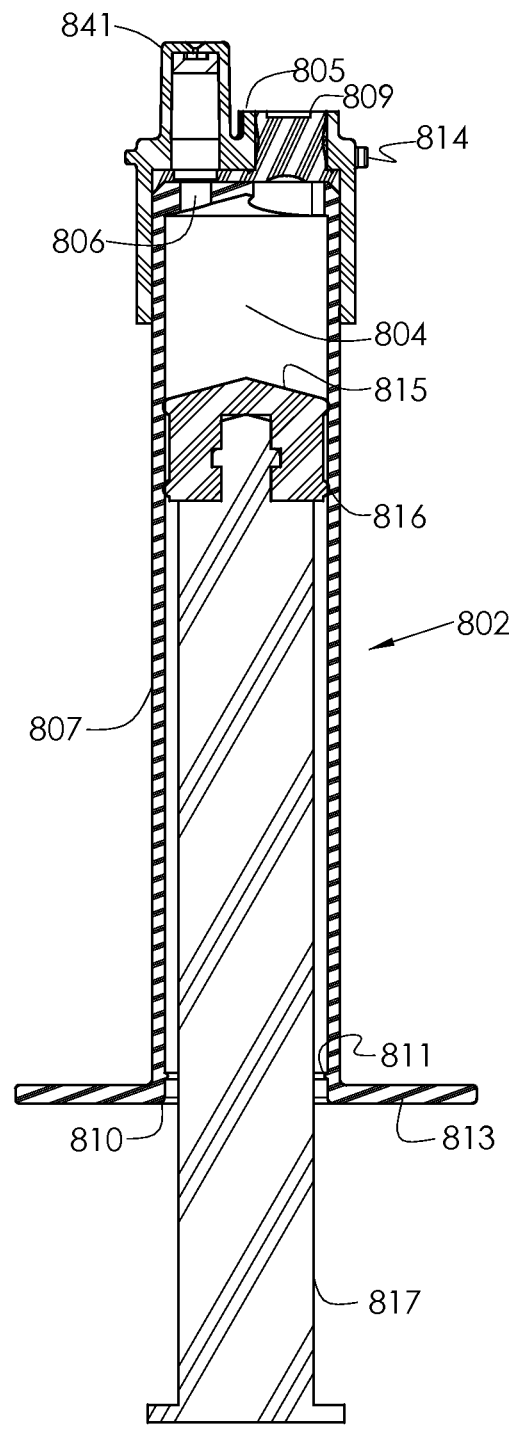

FIG. 23-23A are sectional plane and cross-sectional views of a syringe (802) showing a closed first end (805) dispensing member (806), spray nozzle (841), and access port (809). Open second end (810) has proximally located plunger retaining means (811) for preventing the stopper and plunger rod from exiting the syringe, and protruding flange (813) located proximal to the open second end and having alignment means (814) located proximal to the first end. Stopper (815) having seal rings (816), is attached to plunger rod (817).

FIGS. 24-24A and 25-25A are sectional plane and cross-sectional views of a combination vial access device and syringe with needle-stick safety mechanism. One or more latch members (129) extend from tip cover element (199). Latch members (129) cooperatively latch with shelf (131) on the syringe lower housing while the spring is in its compressed configuration.

Figure 25:
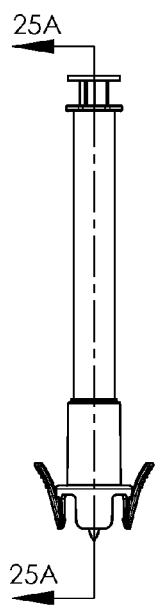
FIGS. 25-25A are sectional plane and partial cross-sectional views of a syringe and vial access device combination embodiment.
Figure 25A:
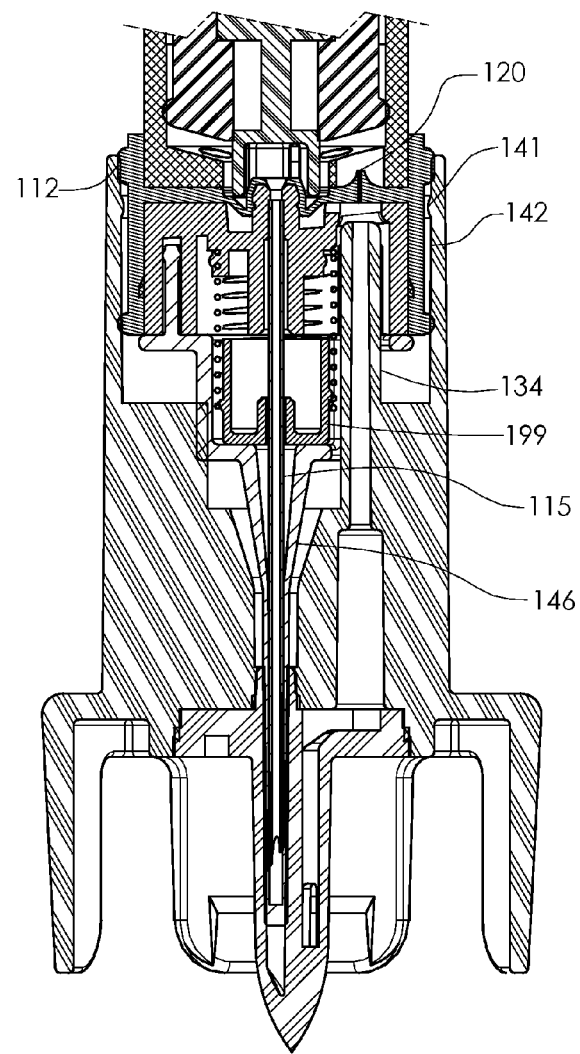

FIG. 25A shows the needle-stick safety mechanism in an un-activated, as-assembled configuration. Syringe accessing member (134) is shown adjacent to pre-slit access port (120) of the access port. Syringe external seal (112) interacts with internal raised feature (141) to act as an indicator for the initial, un-activated configuration. Seals slide against the internal seal wall (142) of the vial access housing. The needle and needle cover (146) are housed inside the receiving means of the housing as shown in the un-activated configuration.

Figures 24, 24A:
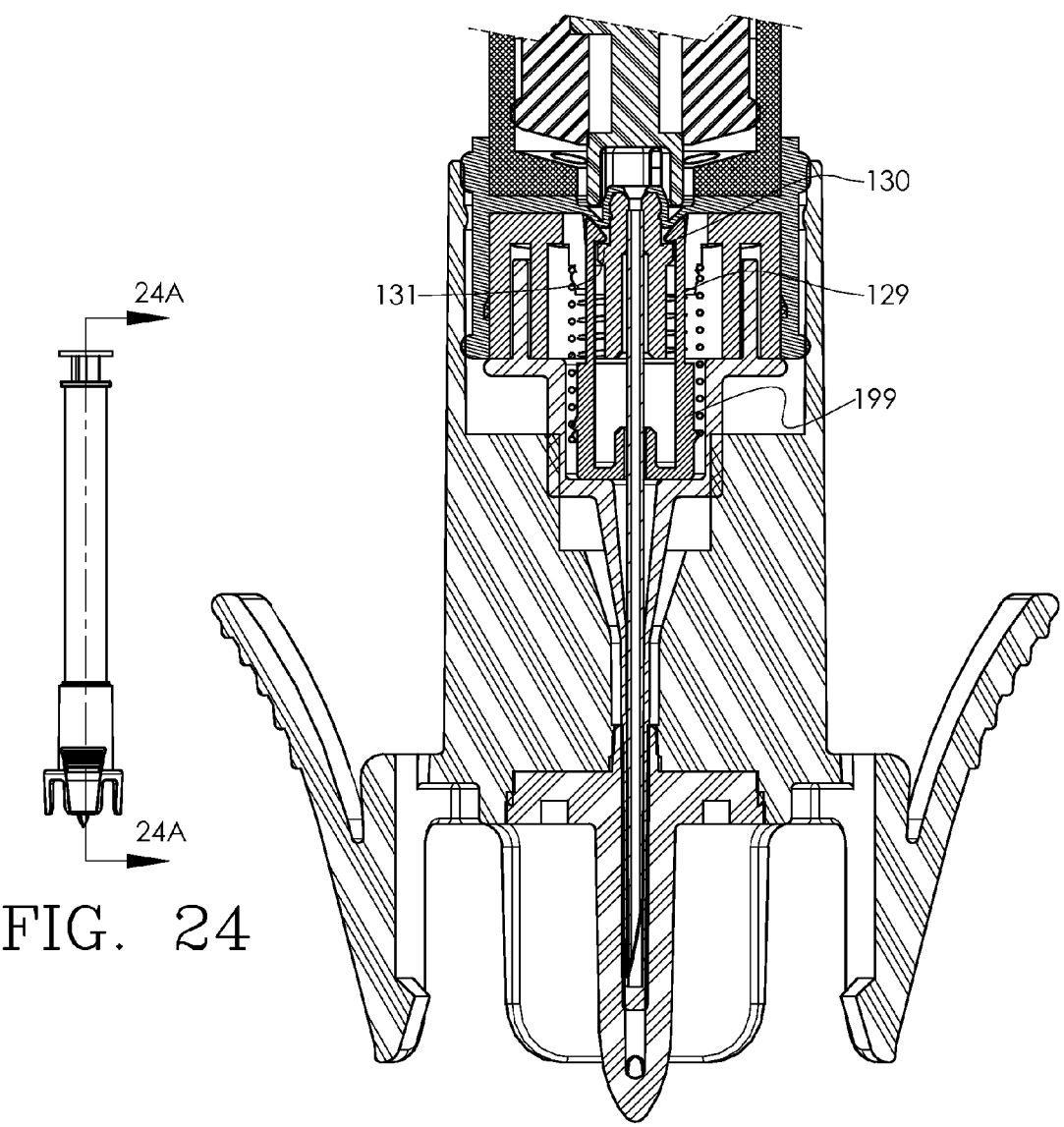
FIGS. 24-24A are sectional plane and partial cross-sectional views of a syringe and vial access device combination embodiment.
Figures 26, 26A:
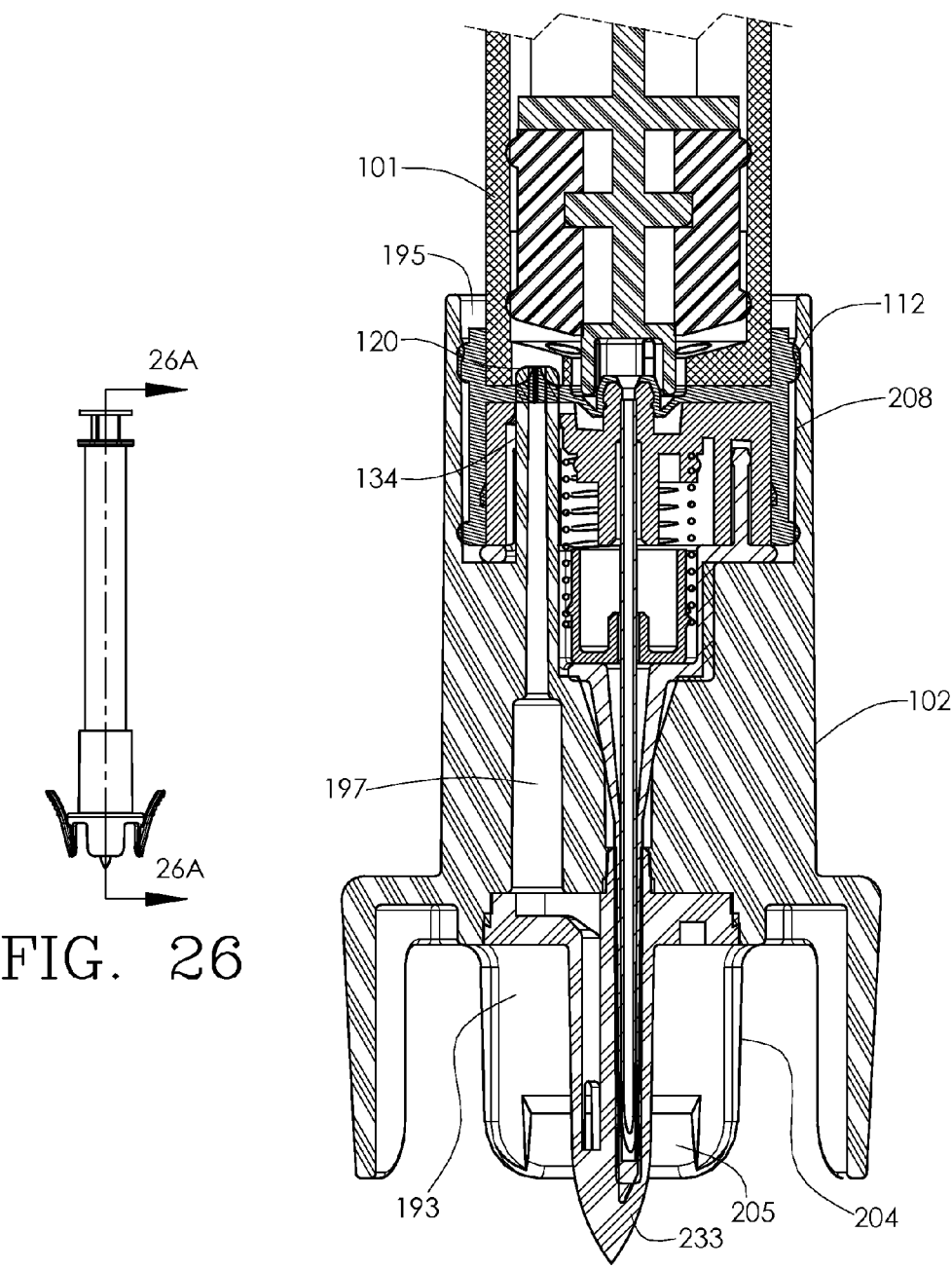
FIGS. 26-26A are sectional plane and partial cross-sectional views of a syringe and vial access device combination embodiment.
Figures 27, 27A:
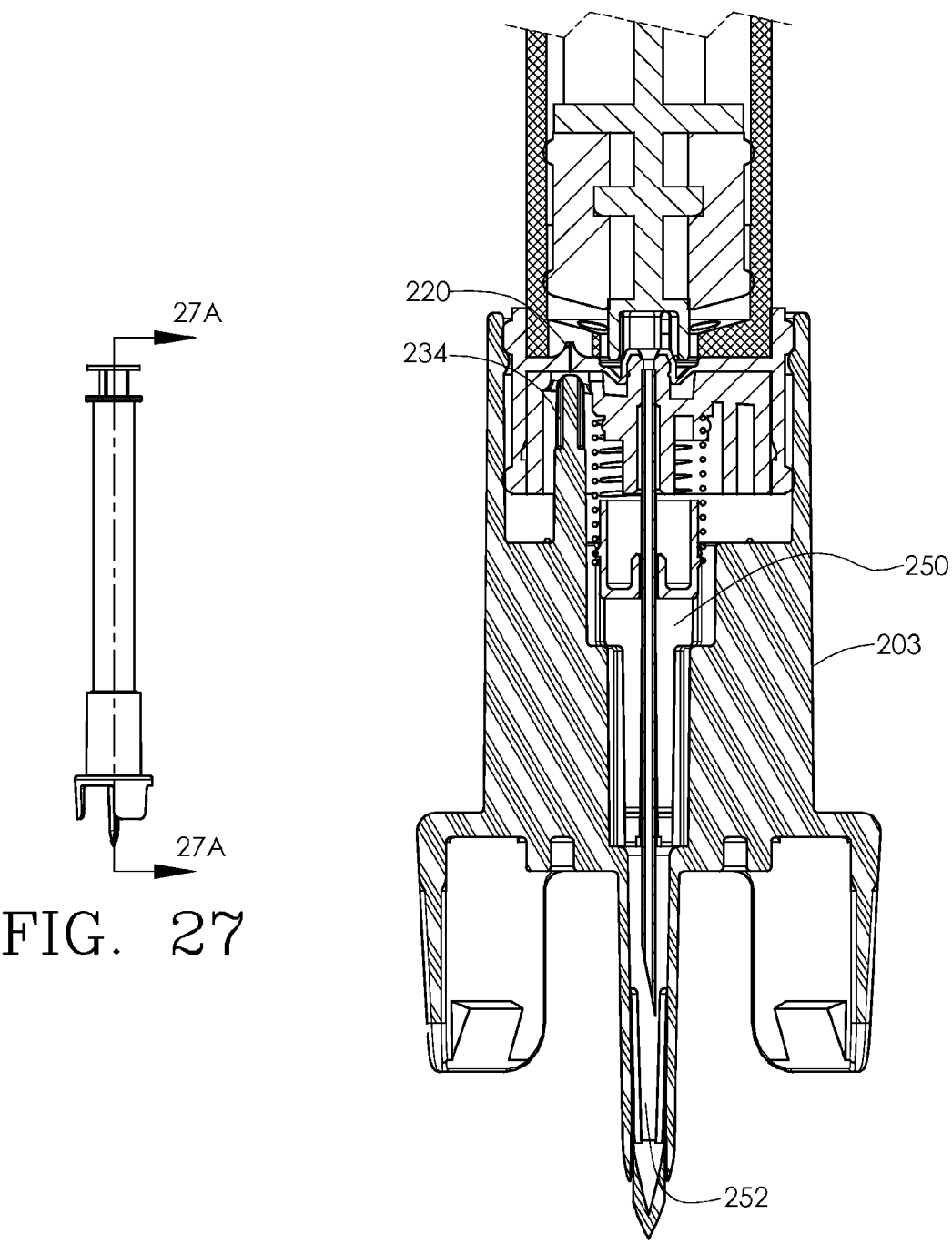
FIGS. 27-27A are sectional plane and partial cross-sectional views of a syringe and vial access device combination embodiment.

FIGS. 26-26A are sectional plane and cross-sectional views of the embodiment of FIGS. 24 & 25 shown in its activated configuration. Seal (112) is fully seated inside the housing of vial access device (102) in this activated configuration. Syringe accessing member (134) pierces pre-slit access port (120) to open a fluid conduit and to allow fluid communication between the syringe (101) and vial access device interconnected conduits (197). Vial attachment device (102) comprises an open first end (195) having sealable interface (208), a second end (193) terminating in a spike-like vial accessing member (233) and an syringe accessing member (134) extending from an internal portion of the housing of device (102) for accessing a pre-slit access port (120) or the like. The vial accessing member may comprise any number of openings to its exterior and any number of internal lumens. At least one internal lumen is in fluid communication with the interior portion providing for interconnected conduits. The syringe accessing member may have any form such that it may pierce a pre-slit access port or the like and allow fluid communication through the pre-slit access port. The second end of the housing comprises a plurality of attachment means (204) having guide tabs (210) concentric about the spike-like portion. Opposing attachment means consist of locking means (205). The attachment means may also comprise removal tabs (206) extending from the attachment tab end. Gripping means (207) proximal to the removal tab are optional. FIGS. 27-27A depict an alternate embodiment of FIG. 25A where syringe accessing member (234) has external slots, with receiving means (250) for needle/needle cover is located within vial accessing member (233) not isolated from fluid conduit (252).

Figures 29, 29A:
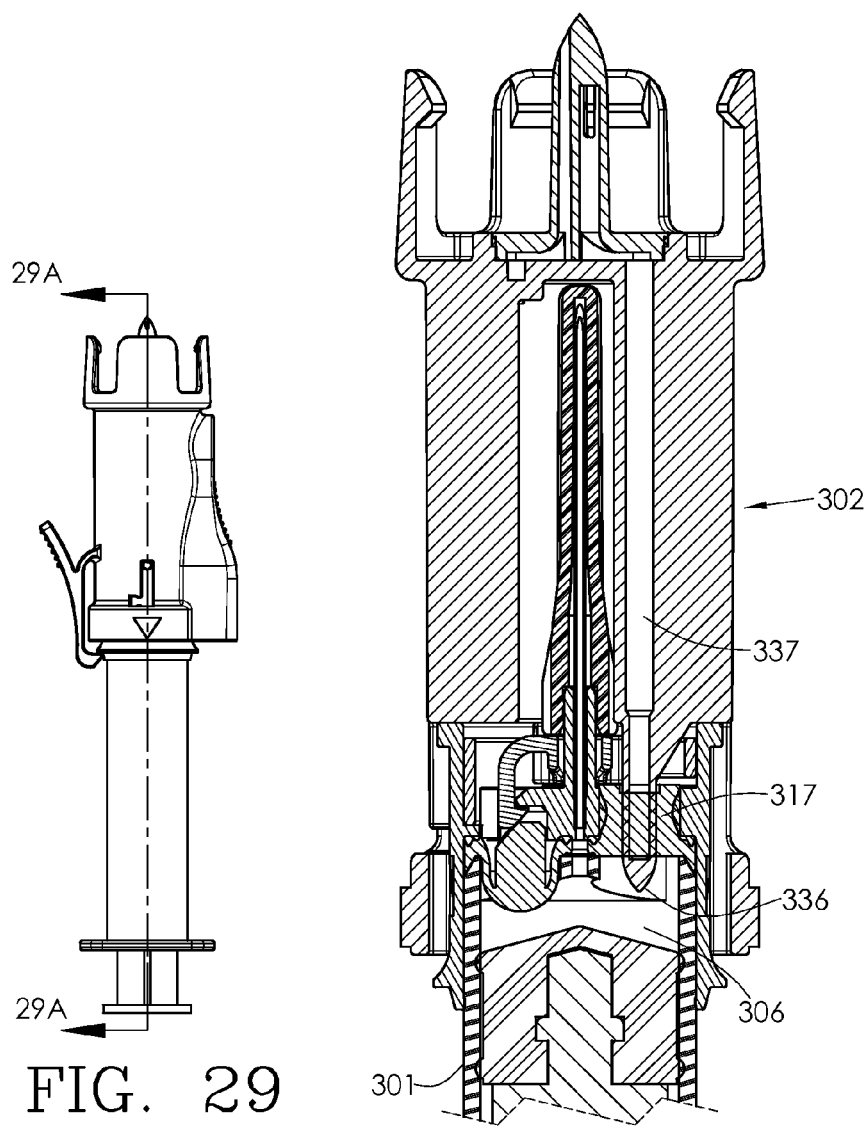
FIGS. 29-29A are sectional plane and partial cross-sectional views of a syringe and vial access device combination embodiment.

FIG. 28-28A are sectional plane and cross-sectional views of the combination of vial access device and syringe with needle-stick mechanism in the un-activated pre-access configuration preventing fluid communication between the syringe accessing member and the syringe. As shown, syringe accessing member (336) is aligned with access port (317) of the syringe for piercing. FIGS. 29-29A are sectional plane and cross-sectional views of the combination of vial access device and syringe with needle-stick mechanism in the activated bypass access configuration allowing fluid communication between the syringe accessing member and the syringe. As shown, syringe accessing member (336) pierces access port (317) of the syringe allowing for fluid communication between syringe (301) and interconnected conduit (337) of vial access device (302).

Figures 30, 30A:
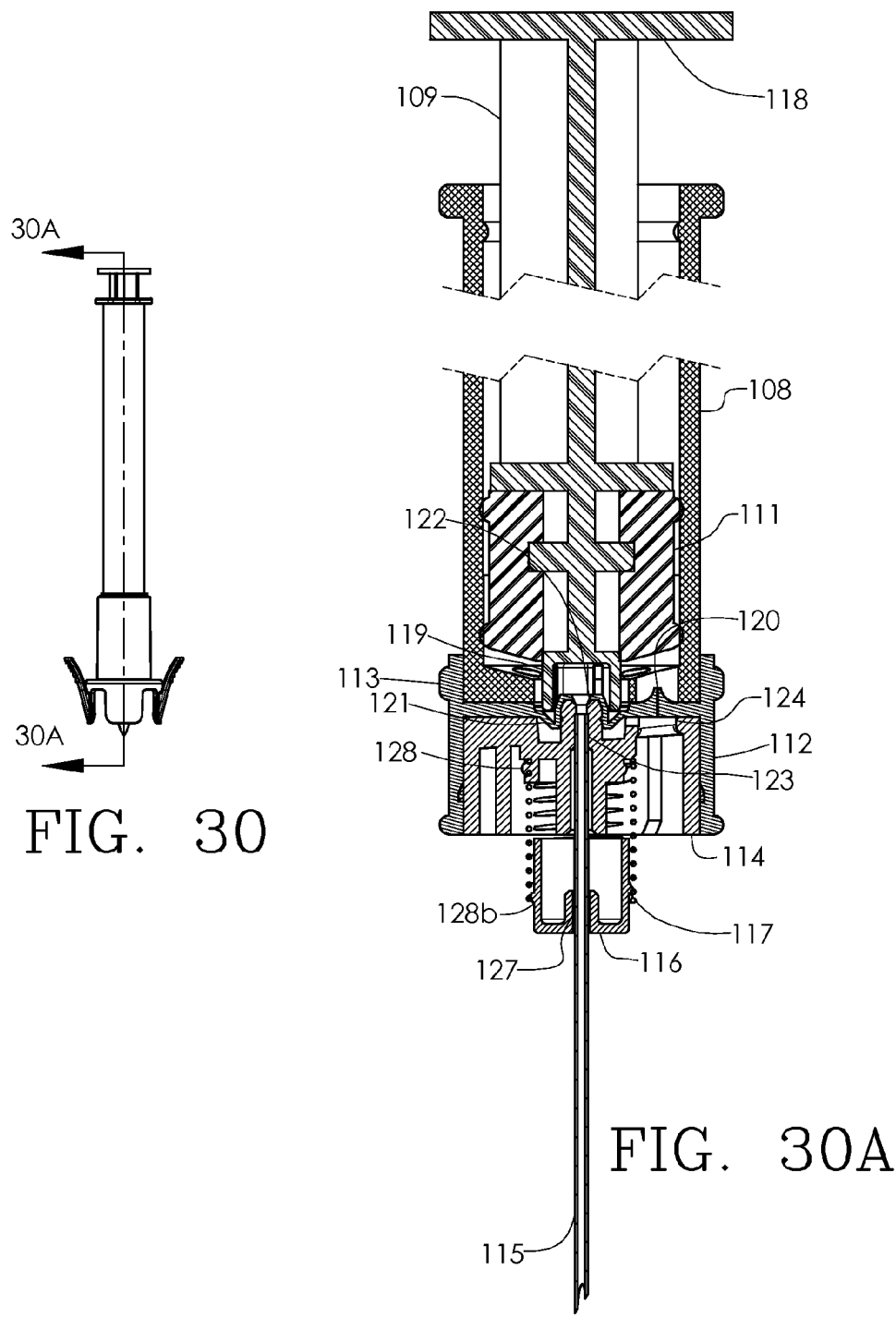
FIGS. 30-30A are sectional plane and partial cross-sectional views of a of a needle-stick safety mechanism embodiment.
Figures 31, 31A:
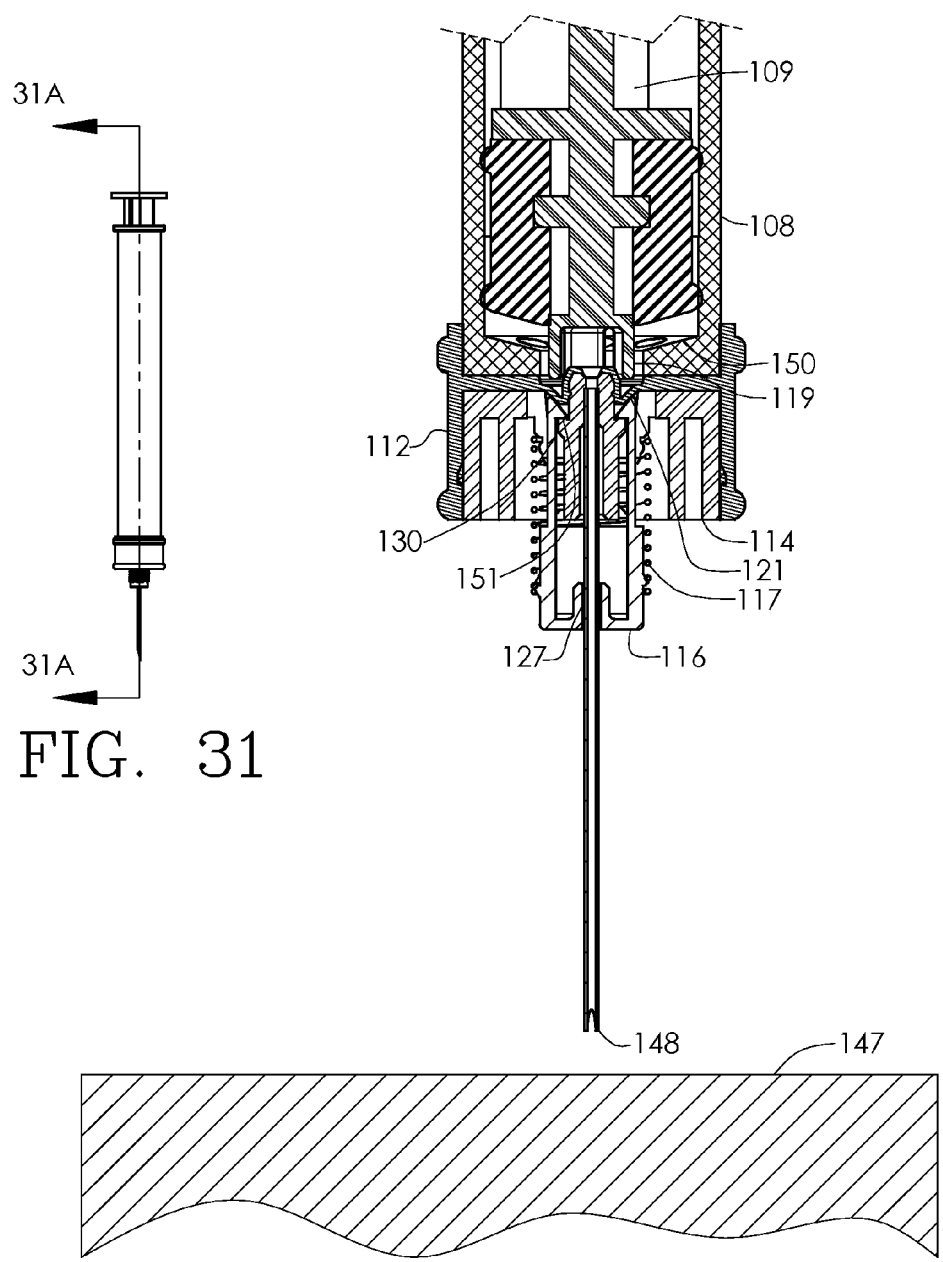
FIGS. 31-31A, 32-32A and 33-33A are sectional plane and partial cross-sectional views of a of a needle-stick safety mechanism embodiment shown prior to needle access in subject, needle fully inserted into subject, and needle retraction from subject with safety mechanism deployed, respectively.
Figures 32, 32A:
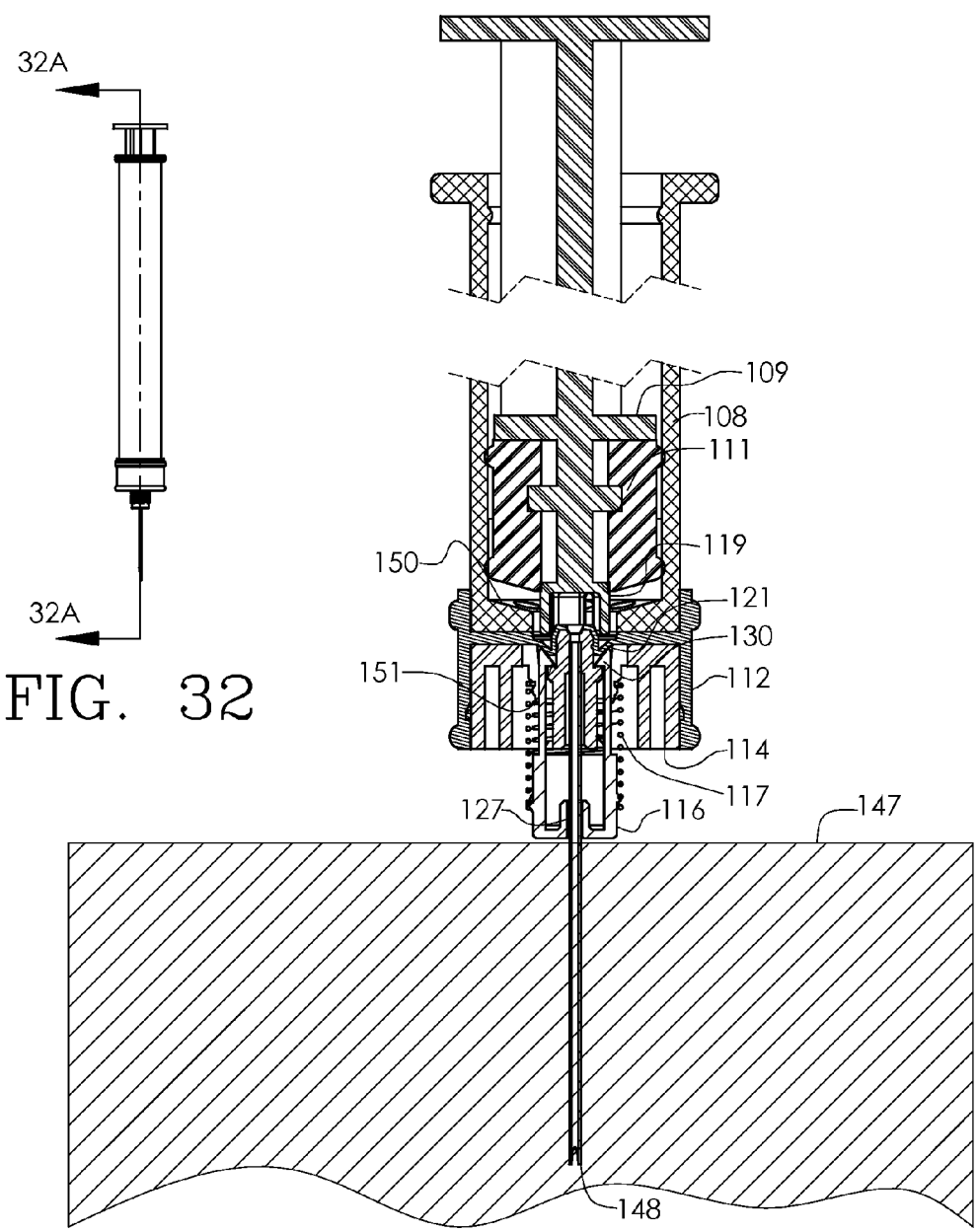

FIG. 30-30A are sectional plane and cross-sectional views of a syringe with needle-stick mechanism. Syringe comprises plunger rod (109), stopper (111), syringe barrel (108), syringe external seal (112), lower housing (114), hollow needle (115), needle-tip cover (116) and spring (117). The plunger rod may comprise flanges (118) at one end and a plurality of protrusions (119) at the opposing end. The plunger rod is coupled to the stopper. The syringe barrel is coupled to the syringe external seal (112), syringe external seal (112) comprising pre-slit access port (120), deformable member (121) with centrally located fluid conduit (122), and an external syringe outer sealing means (113). Lower housing (114) is joined to the syringe barrel and may also mechanically join the syringe external seal (112) to the syringe barrel. The lower housing comprises hub (123) for a hollow needle, an access conduit (124) to pre-slit access port (120). Fastening means (128) secures spring (117) to the lower housing (114). Needle-tip cover (116) is shown in its initial un-actuated configuration comprising two open ends with one end providing a guide hole (127) for the needle tip and fastening means (128b) for the spring.

Figures 33, 33A:
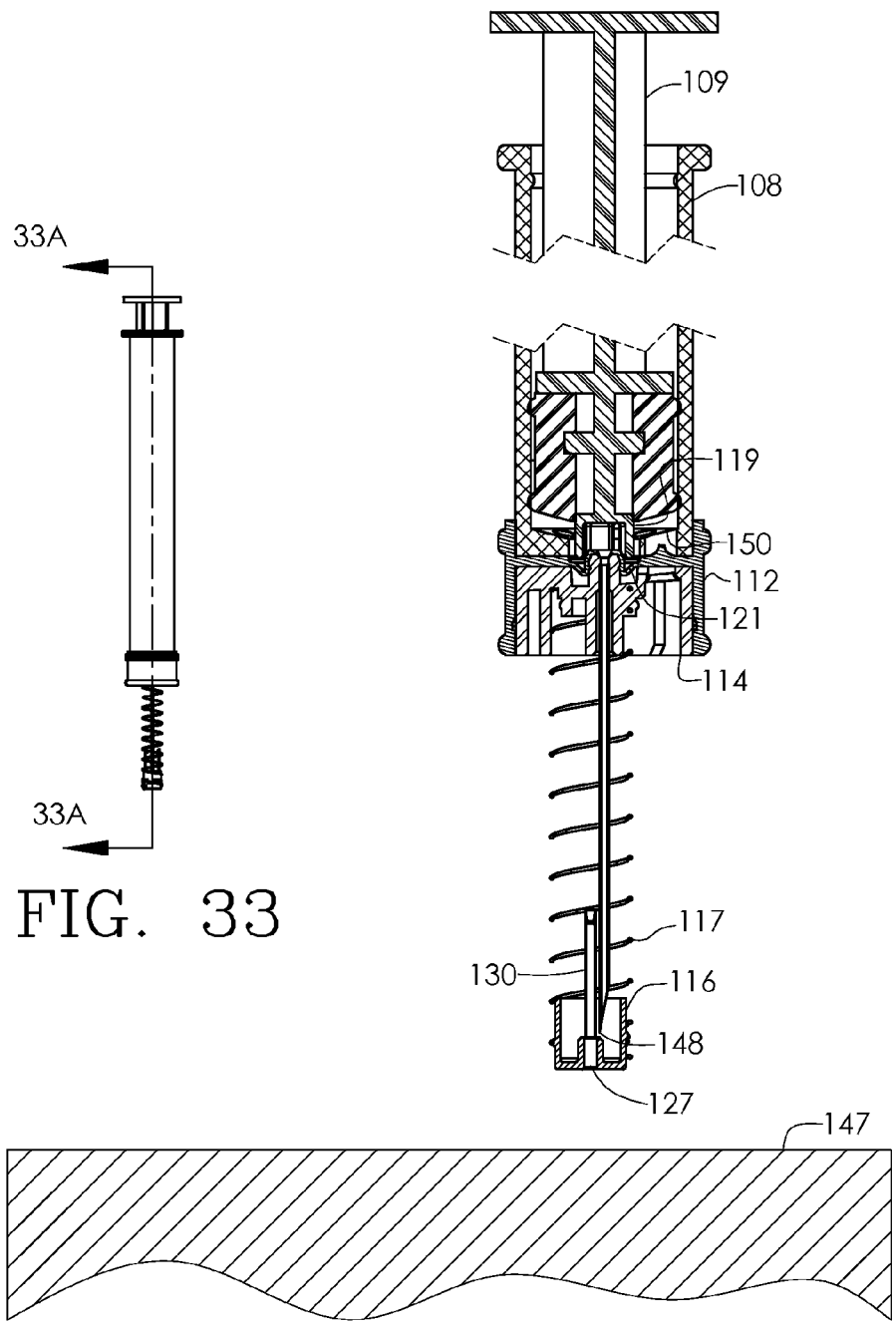

FIGS. 31-33A depict in sequence, cross-sectional views of the syringe with needle-stick mechanism prior to needle insertion to skin (147), with the needle fully inserted into skin (147) and the syringe plunger seated at base (150) of syringe barrel (108), and retracted from the skin, respectively. Referring to FIG. 32A, upon end-of-stroke after administration, protrusions (119) of plunger rod (109) contacts deformable member (121) of syringe external seal (112) and further act to move needle-tip cover latches (130) from shelves (151) on lower housing (114). Referring to FIG. 33A, upon retraction of needle from skin, needle-tip cover (116) releases and spring (117) sends needle-tip cover (116) covering needle-tip (148). The spring may be assembled off-center from the needle so that, when the needle-tip cover reaches the end of its travel, the needle and guide hole (127) of the needle-tip cover are likewise misaligned.

Figure 34:
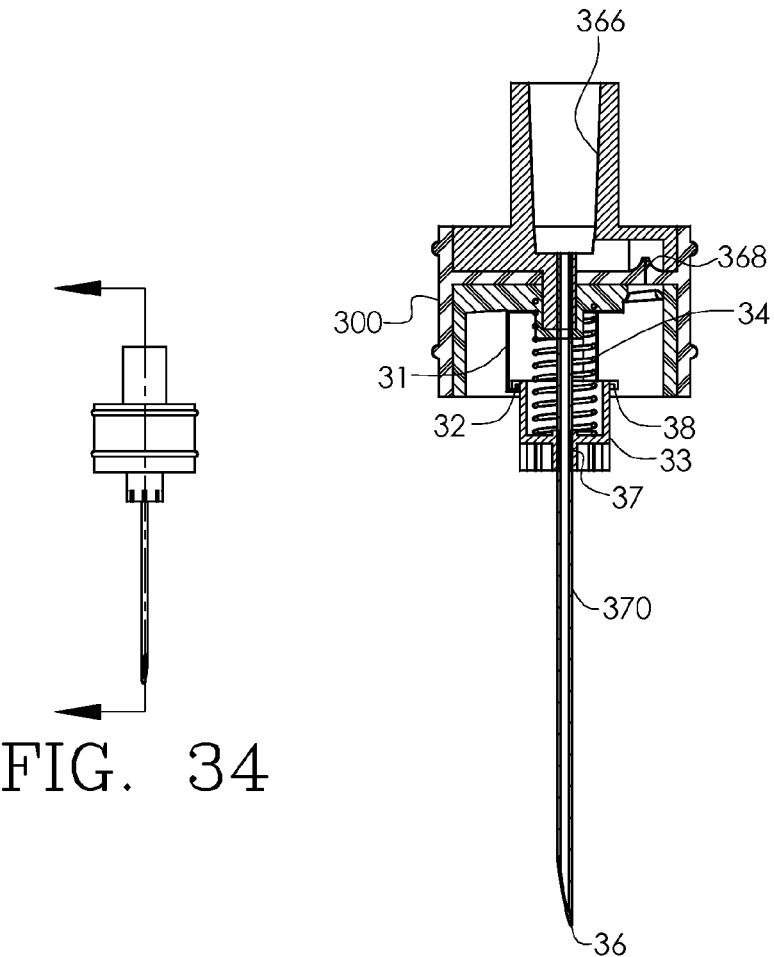
FIGS. 34-34A, 35-35A and 36-36A are sectional plane and cross-sectional views of a needle-stick safety mechanism embodiment shown prior to needle access in subject, needle fully inserted into subject, and needle retraction from subject with safety mechanism deployed, respectively.
Figure 34A:
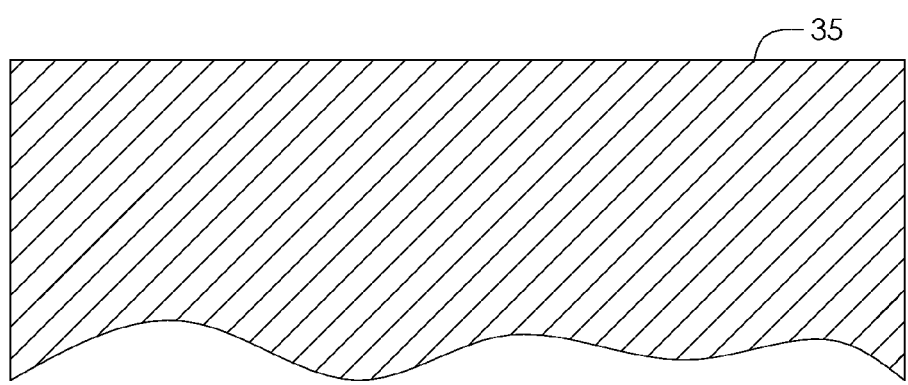
Figure 35:
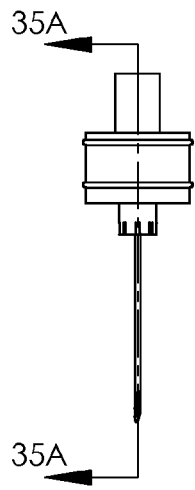
Figure 35A:
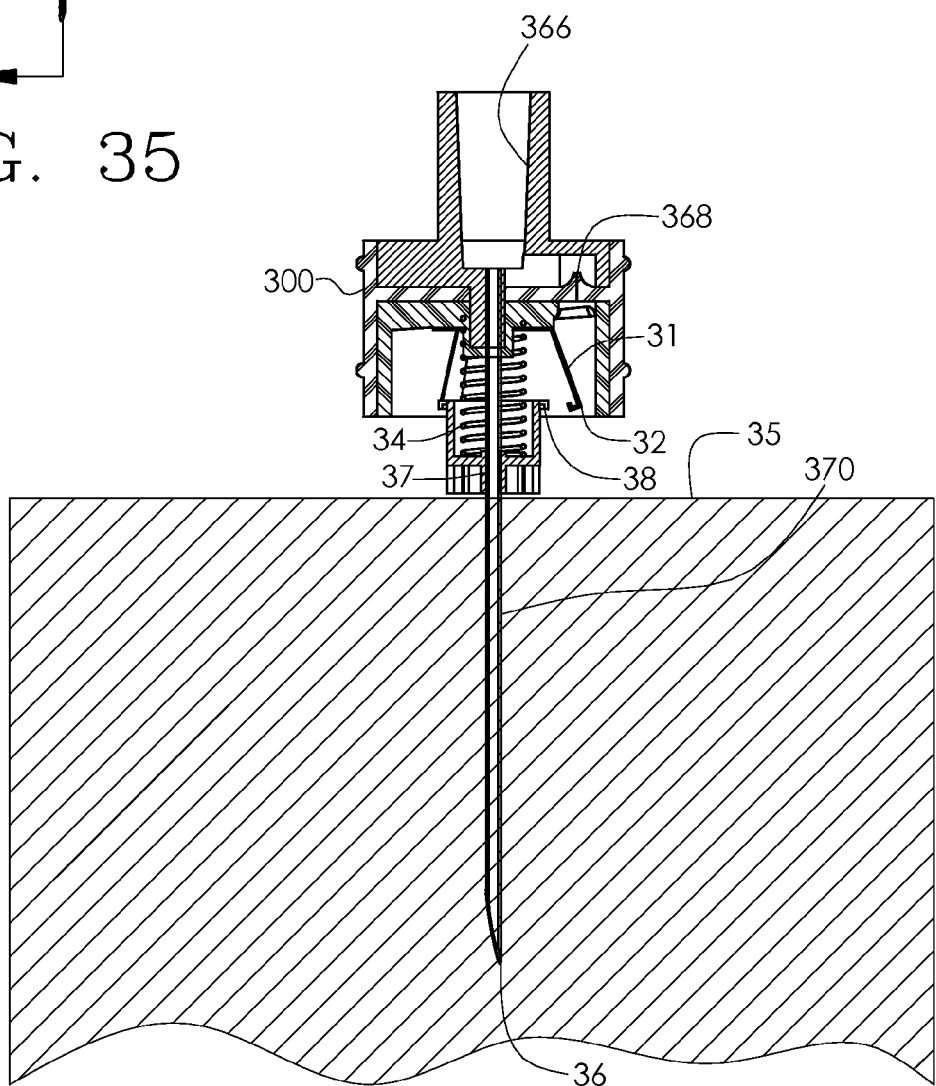
Figures 36, 36A:
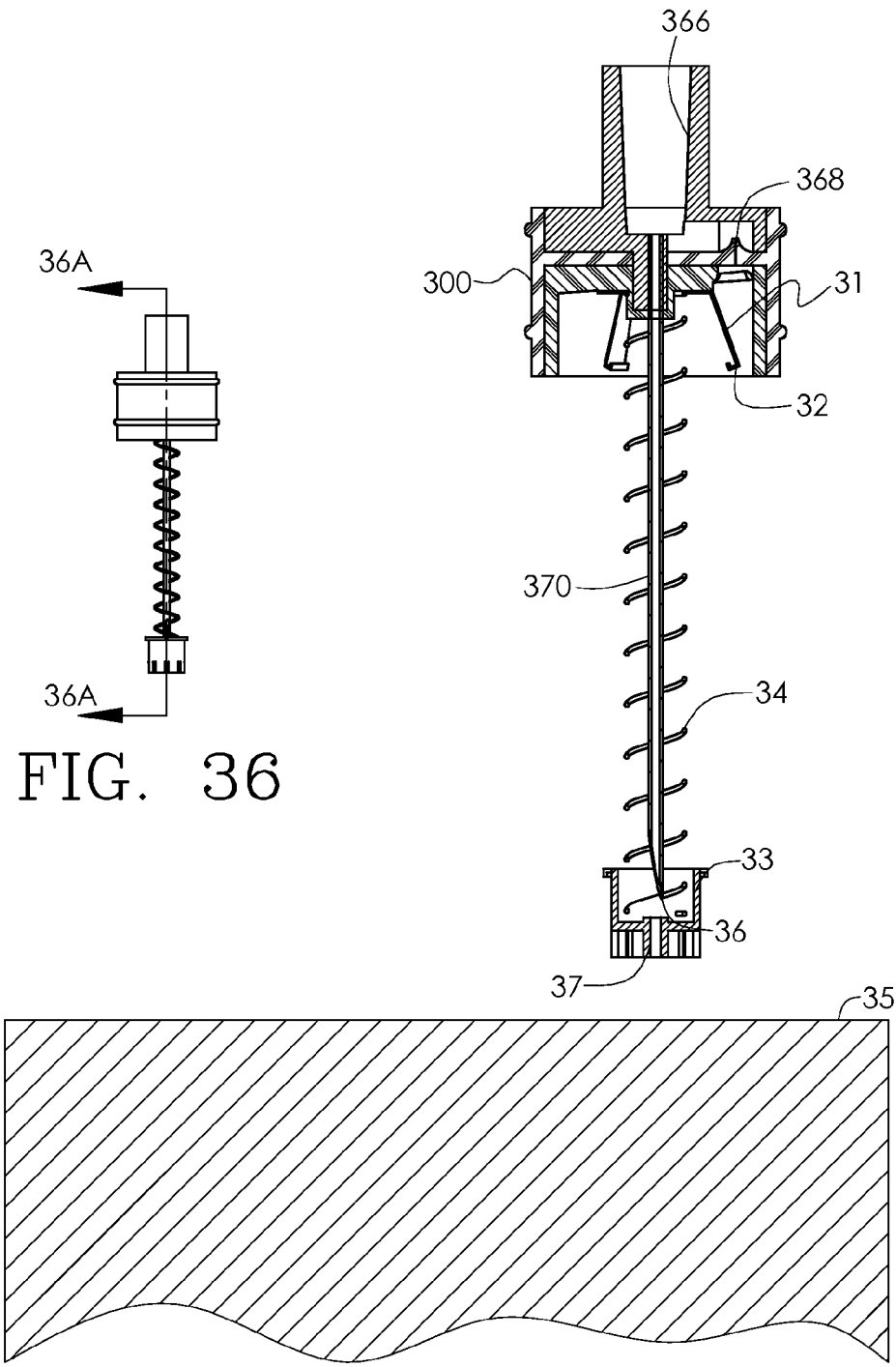

FIGS. 34-36A depict, in sequence, cross-sectional views of another embodiment of a needle-stick mechanism prior to, inserted into, and retracted from the skin. Thus, FIG. 34A shows a needle-stick safety mechanism with needle (370), the needle-stick safety mechanism integrated with female luer (366) for attachment to a standard male luer syringe (not shown). The needle-stick safety mechanism has integrated access port (368) for bypassing needle (370). Housing 300 is adapted for connection with the vial access device described herein. Latch mechanism with plurality of arms (31), each comprising interlocking feature (32) is shown with the arms in un-sprung tension. Needle-tip cover (33) has mating shelf (38) receiving interlocking feature (32), which holds spring (34) in a compressed state. FIG. 35A is a cross-sectional view of the needle-stick safety mechanism shown with the needle fully inserted into skin (35). Arms (31) have been sprung to their natural configuration. FIG. 36A is a cross-sectional view of the needle-stick safety mechanism shown with the needle retracted from skin (35). Spring (34) has been released and needle-tip cover (33) covers needle-tip (36). Guide hole (37) is configured off-center from the needle-tip.

Figure 37:
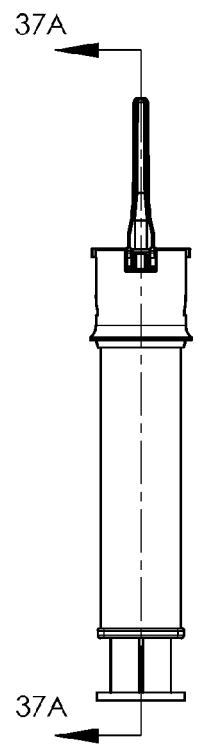
Figure 37A:
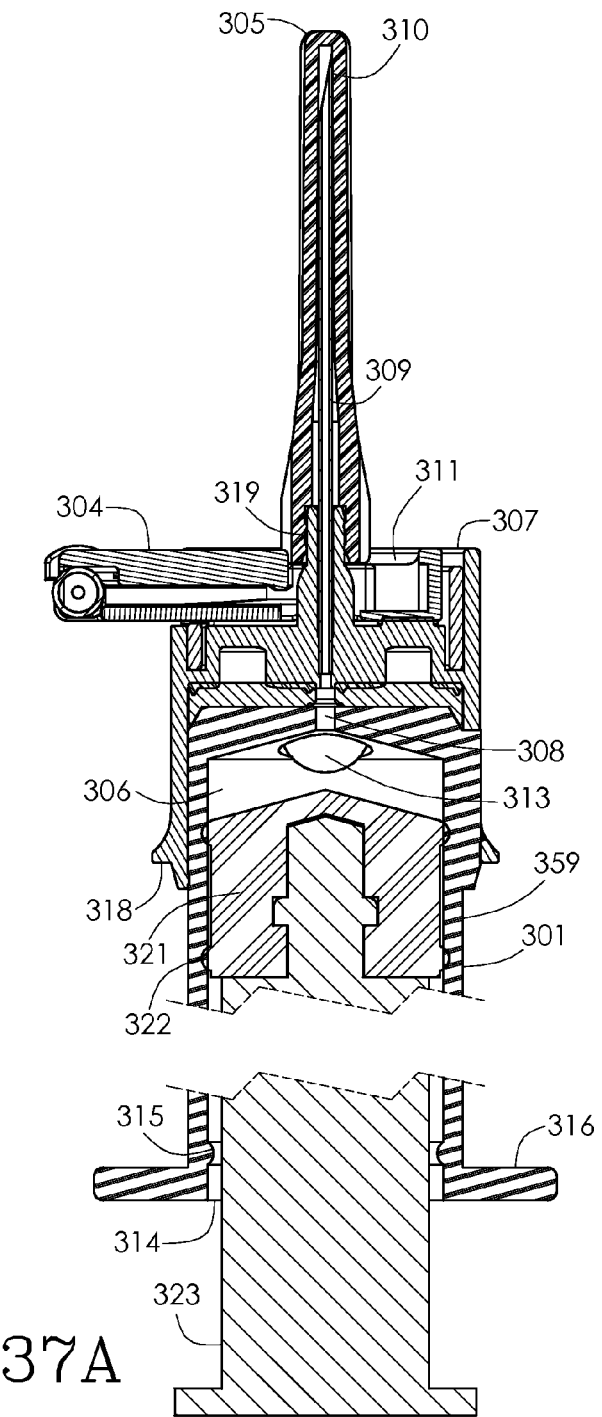

FIGS. 37-38A are sectional plane and cross-sectional views of another embodiment of a syringe with removable needle cover and needle-stick safety mechanism. FIG. 37A depicts syringe (301) with needle cover (305) and needle-stick safety mechanism (304) and attached lower housing (307). Syringe (301) has open end (314) having any number of proximally located retaining means (315) and exterior portion (359) having protruding flanges (316). Syringe (301) comprises elastomeric stopper (321) having any number of seal rings (322) joined to plunger rod (323). Lower housing (307) has inner portion (311) for accepting needle-stick safety mechanism (304) also including latching shelf (312) to secure needle-stick safety mechanism latch (324) in an un-activated state. Lower housing (307) also comprises deformable member (313) and access port (317) allowing for fluid communication with the syringe when pierced by an accessing member and at least one vial access device coupling means (318). Lower housing (307) comprises hub portion (319) allowing for a sealable connection with a needle and/or needle cover. Lower housing (307) includes alignment means (320). Fluid conduit (308) provides for fluid communication with hollow needle (309) having pointed distal end (310). FIG. 38A depicts latch (324) of a needle-stick safety mechanism in its collapsed, un-deployed configuration, coupled with latching shelf (312) of the lower housing.

Figures 39, 39A:
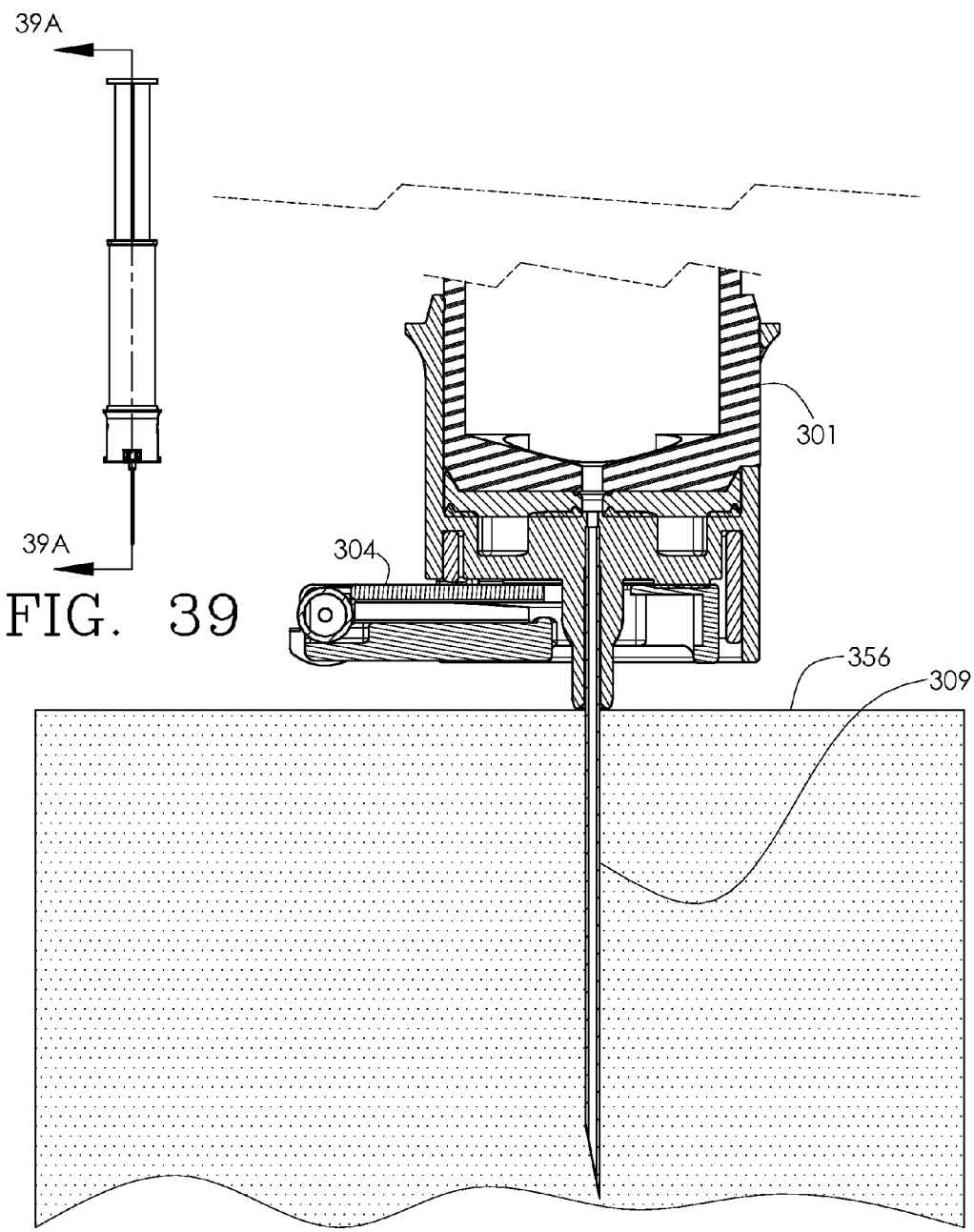
FIGS. 39-39A and 40-40A are sectional plane and partial cross-sectional views, respectively, of a needle-stick safety mechanism embodiment and needle fully inserted into a subject, with plunger in the reward and forward positions, respectively, prior to deployment.
Figure 40:
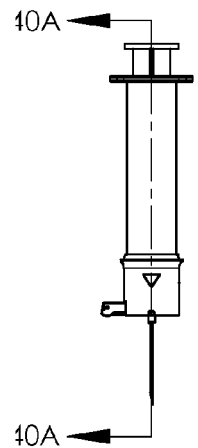
Figure 40A:
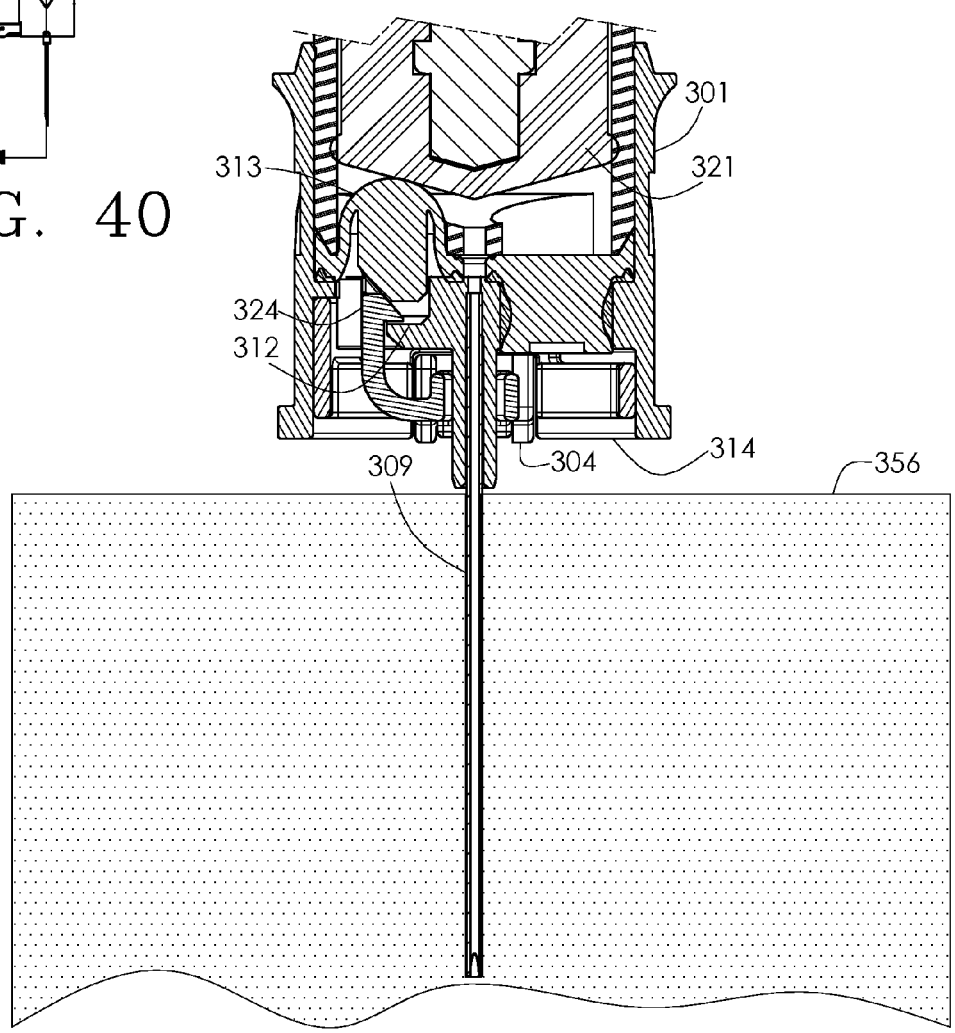

FIGS. 39-40A are sectional plane and cross-sectional views of the embodiment of FIGS. 37-38A depicting the activation of the needle-stick safety mechanism. FIG. 39A shows syringe (301) with needle-stick safety mechanism (304) inserted into skin (356). As syringe stopper (321) approaches second end (314) of the syringe, fluid is expelled through hollow needle (309). When the syringe stopper reaches end-of-stroke, it contacts deformable member (313) releasing latch (324) from latching shelf (312) of the needle-stick safety mechanism, activating and deploying the needle-stick safety mechanism, as shown in FIG. 40A. FIG. 49 is a perspective view of needle stick safety mechanism of FIGS. 39-40 in its fully deployed configuration after the needle is retracted from the skin. Locking tabs (357) and mating locking shelves (358) prevent the mechanism from collapsing and exposing needle (309).

Figure 41:
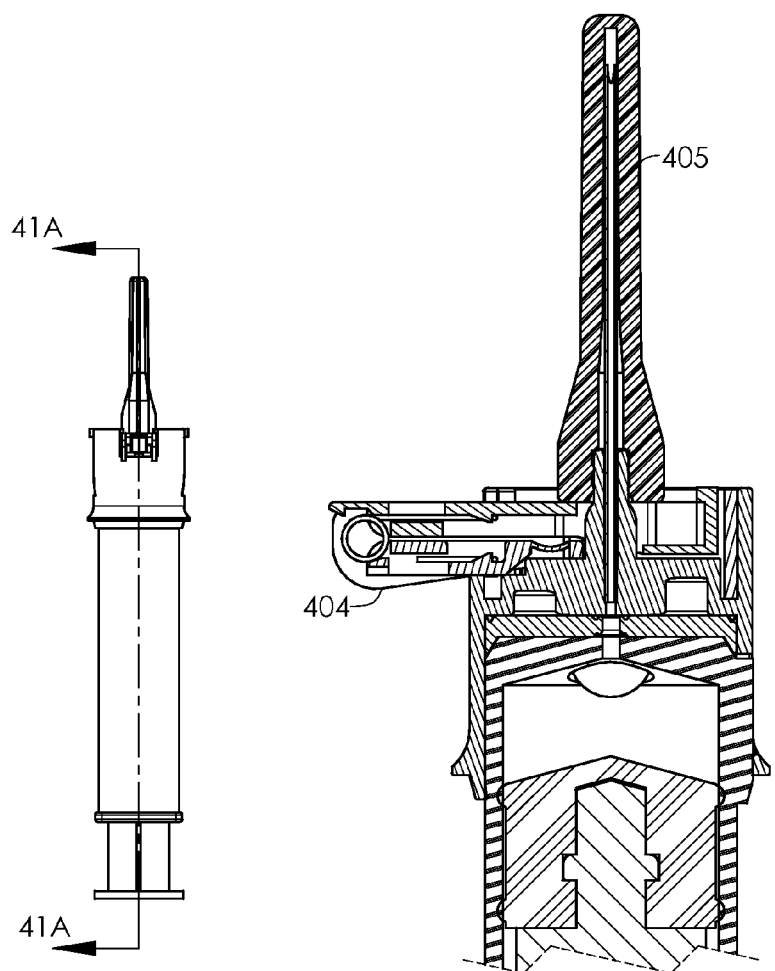
FIGS. 41-41A and 42-42A are sectional plane and partial cross-sectional views, respectively, of a needle-stick safety mechanism embodiment with needle cover.
Figure 41A:
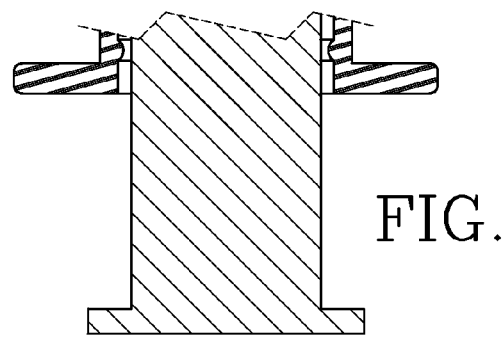
Figure 42:
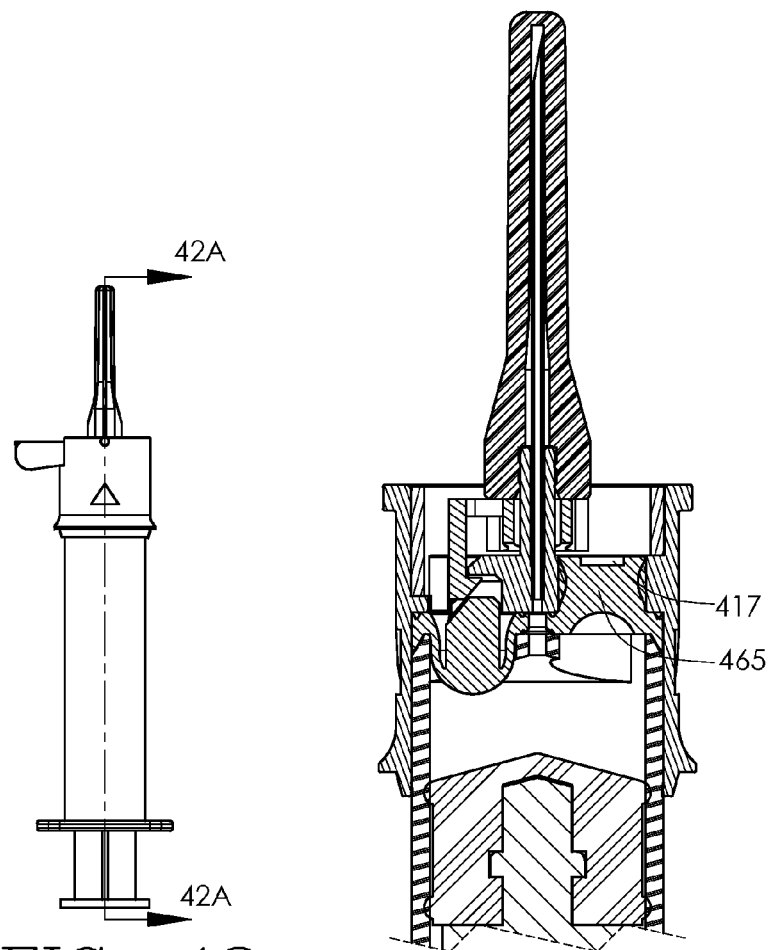
Figure 42A:
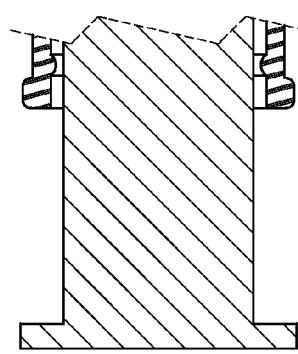
Figure 43:
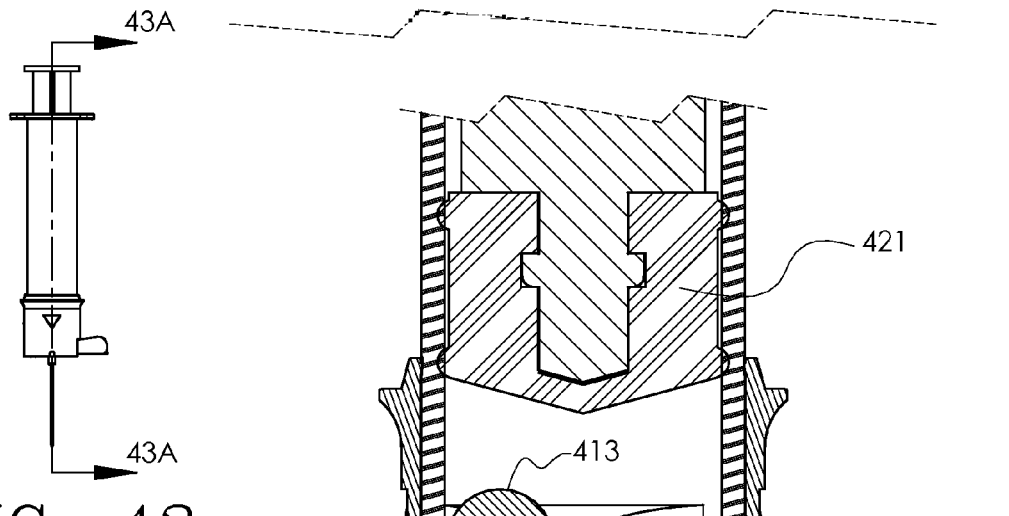
FIGS. 43-43A and 44-44A are sectional plane and partial cross-sectional views of the needle-stick safety mechanism embodiment of FIGS. 41-41A, shown fully inserted into subject, with plunger in the reward and forward positions, respectively, prior to deployment.
Figure 43A:
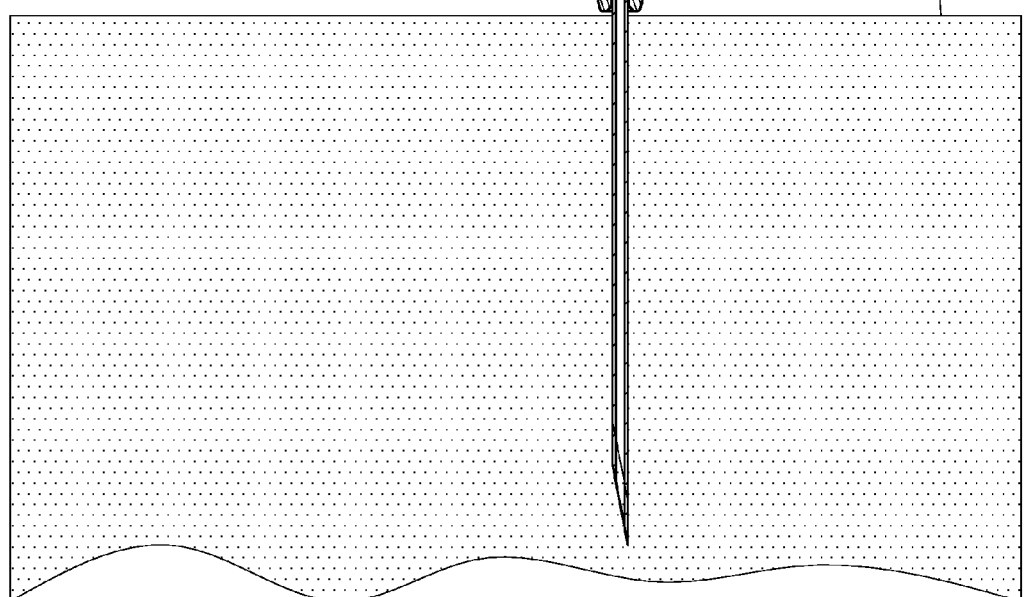
Figures 44, 44A:
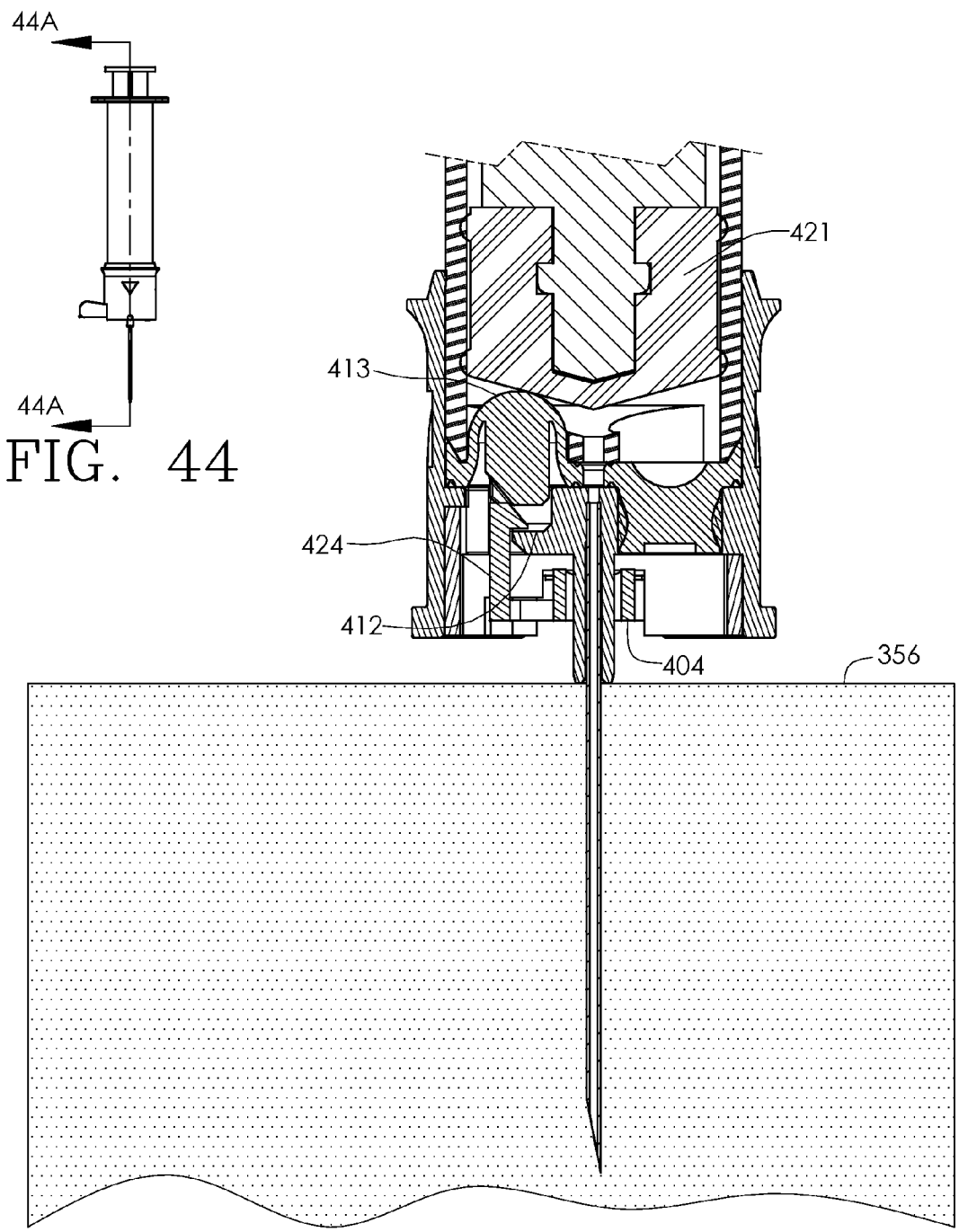
Figure 45:
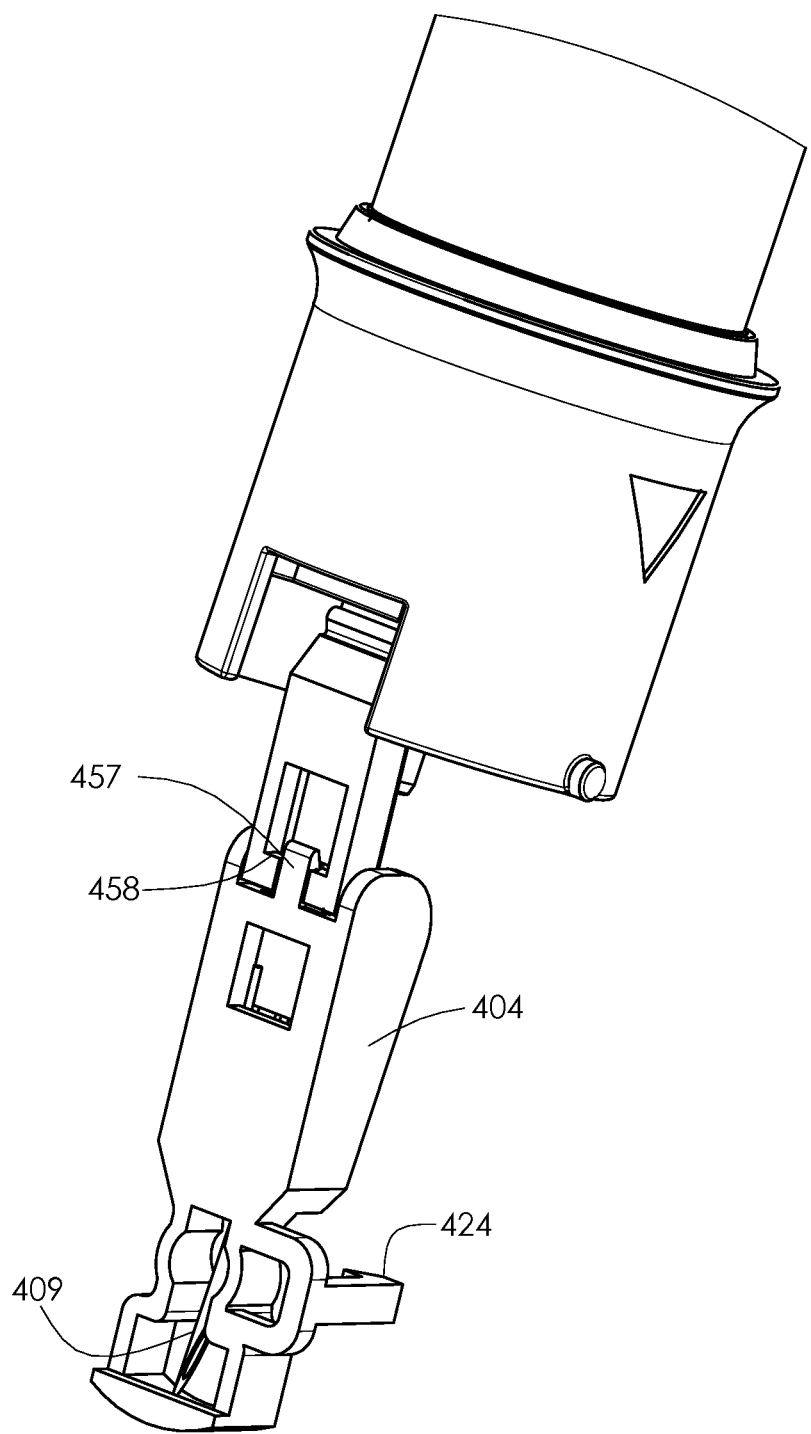
FIG. 45 is a perspective view of the needle-stick safety mechanism embodiment of FIGS. 41-41A, shown in a deployed configuration.

FIGS. 41-42A are sectional plane and cross-sectional views of another embodiment of a syringe with removable needle cover and needle-stick safety mechanism. FIG. 41A depicts needle cover (405) and needle-stick safety mechanism (404); a syringe as described in FIG. 42A depicts access port (417) having alternate geometries (465) preventing coring and/or allow for greater flow rates. The geometries of the access port include, but are not limited to, embossed means, de-bossed means or a combinations thereof. FIGS. 43-44A and 45 depict the needle-stick safety mechanism (404) sequence of activation and final configuration of FIGS. 41-42A. As syringe stopper (421) reaches end-of-stroke, it contacts deformable member (413) releasing latch (424) from latch shelf (412) of the needle-stick safety mechanism, activating and deploying the needle-stick safety mechanism (404). Locking tab (457) and mating locking shelf (458) prevent the mechanism from collapsing and exposing needle (409).

Figure 46:
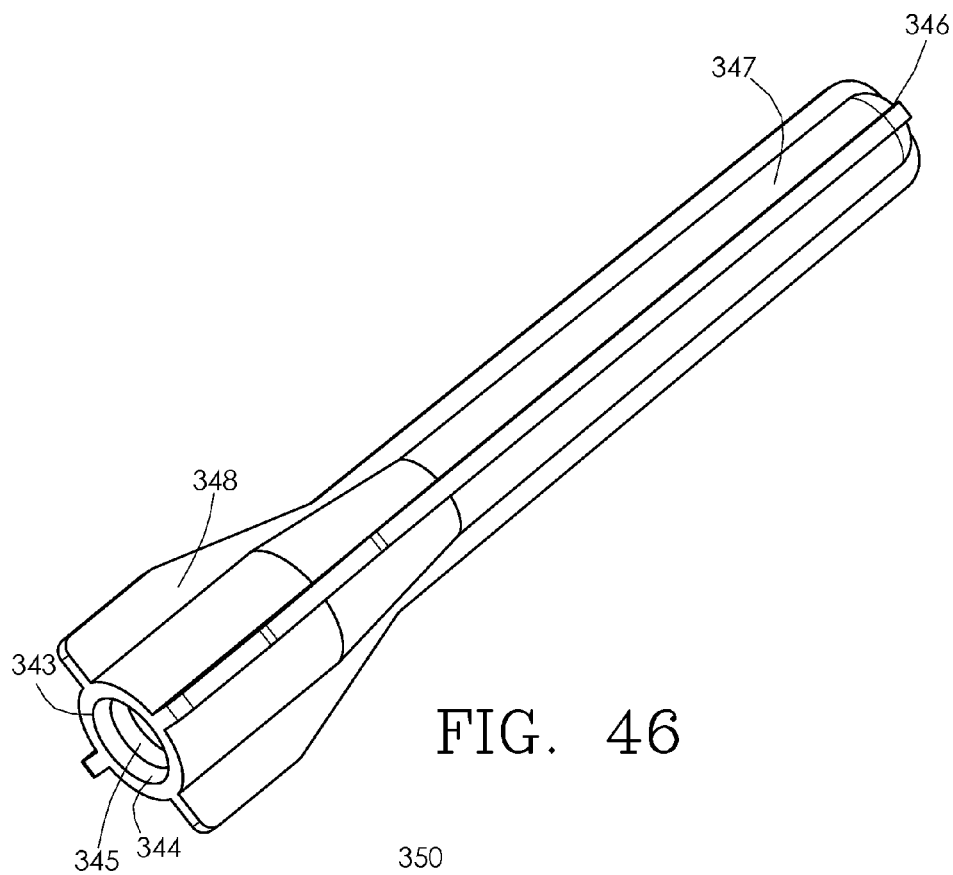
FIG. 46 is a perspective view of a needle cover embodiment.

FIG. 46 is a perspective view of a needle cover comprising open first end (343); internal portion (344) with seal rings (345) proximal to the open first end, closed second end (346), external portion (347) having ribs or gripping means (348). The open first end and internal portion of the needle cover sealably mates with a syringe hollow needle hub. The cover is shaped and/or sized for receiving means of the access device.

Figure 47:
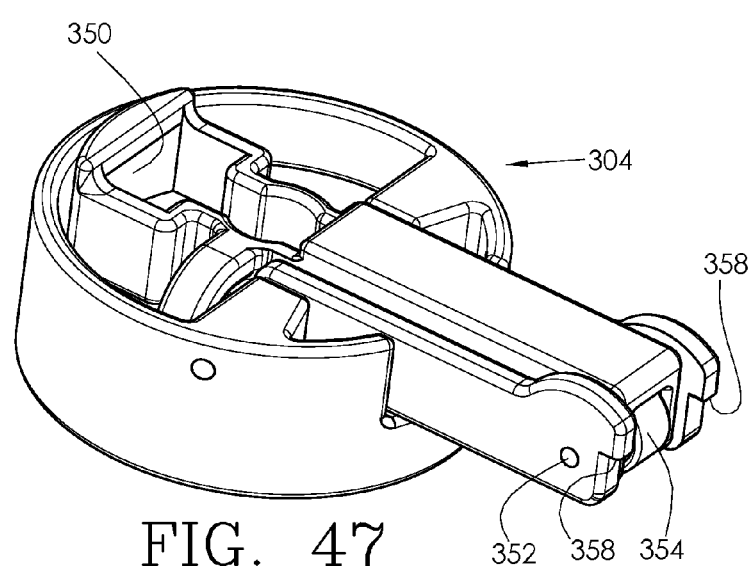

FIGS. 47-48 are perspective views of needle-stick safety mechanism (304) of FIGS. 37-40A shown in its collapsed and deployed configuration, respectively. The hinges and geometries shown allow for the mechanism to collapse upon itself to minimize its overall size. Needle-stick safety mechanism (304) comprises first end (349) for joining to a lowing housing adaptable to a syringe; second end (350) forming a semi-enclosed space (351), at least one hinge (352) between the first and second ends, at least one latch (324) and a torsionally loadable spring element (354). At least one locking tab (357) is loaded so that when the mechanism is extended as shown in FIG. 48, interference with locking shelves (358) prevents rotation about hinge (352).

Figures 50, 51:
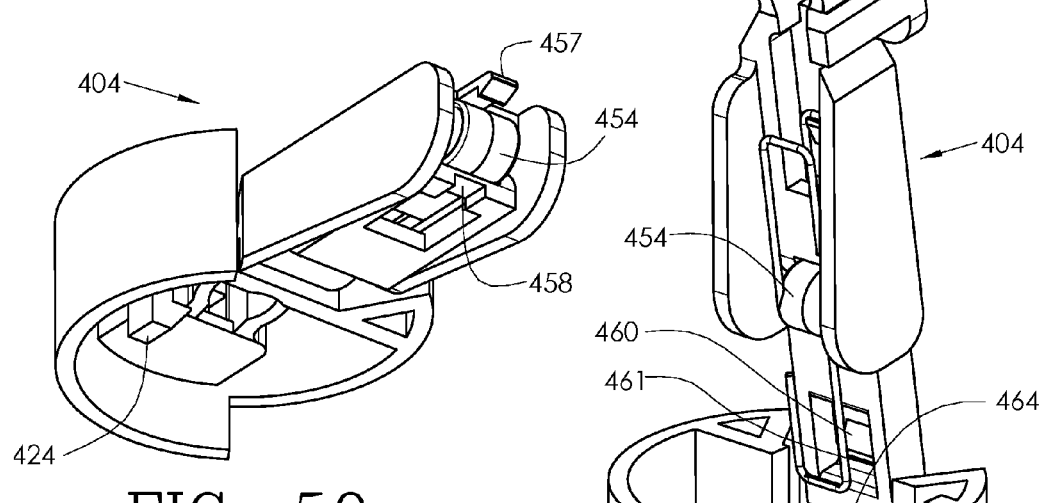
FIG. 50 is a perspective view of a needle-stick safety mechanism embodiment shown in a un-deployed configuration.
FIG. 51 is a perspective view of a needle-stick safety mechanism embodiment shown in a collapsed, deployed configuration.

FIGS. 50 and 51 are perspective views of a needle-stick safety mechanism (404) of FIGS. 43-45A shown in the collapsed and deployed configuration, respectively. Locking tab (460) and locking latch (461) are depicted after deployment by stored energy living hinge (464) and torsionally loaded member (454). The hinges and geometries may allow for the mechanism to collapse upon itself to minimize its overall size.

While the invention has been described in detail and with reference to specific embodiments thereof, it will be apparent to one skilled in the art that various changes and modifications can be made without departing from the spirit and scope of the invention. As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of" As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

We claim:

1. In combination:
a device for mixing and transferring, the device comprising: a
housing having a first open end and a second open end;
a container accessing member having at least one fluid conduit therethrough, the container accessing member extending generally outwardly from the first open end;
a fluid delivery device accessing member having at least one fluid conduit therethrough, the fluid delivery device accessing member extending generally towards the second open end, the fluid delivery device accessing member and the container accessing member in fluid communication therewith; and
a fluid delivery device reversibly securable to the second open end, the fluid delivery device comprising:
a dispensing member at a proximal end; and
a sealable access port at the proximal end configured to receive the fluid delivery device accessing member;
optionally, at least one container reversibly securable to the first open end, the at least one container optionally comprising a transferable substance
receiving means within the housing, the receiving means configured to receive the dispensing member of the fluid delivery device, the receiving means separating the dispensing member of the fluid delivery device from the fluid delivery device accessing member.

2. The combination of claim 1, wherein the fluid delivery device is a syringe.

3. The combination of claim 1, wherein the container accessing member is a high-flow bypass conduit, as defined by flow greater than that obtainable by the dispensing member of the fluid delivery device.

4. The combination of claim 1, wherein the access port of the fluid delivery device is a pierceable member.

5. The combination of claim 4, wherein the pierceable member is a pre-slit-valve, septum, or valved connector.

6. The combination of claim 1, wherein the fluid delivery device accessing member and the container accessing member are in fluid communication through interconnecting fluid conduits.

7. The combination of claim 1, wherein the container accessing member includes a vent lumen, the vent lumen accessing the ambient environment about the housing.

8. The combination of claim 7, further comprising a filter in fluid communication with the vent lumen.

9. The combination of claim 1, further comprising at least one alignment member located on the housing in proximity to the fluid delivery device accessing member, the at least one alignment member reversibly receiving a corresponding alignment member located in proximity to the dispensing member of a fluid delivery device.

10. The combination of claim 1, further comprising container attaching means connected to the housing and located in spaced relation to the container accessing member, the container attachment means securing a container in spaced relation with the container accessing member before or during operation of the device.

11. The combination of claim 1, further comprising fluid delivery device attaching means connected to the housing and located in spaced relation to the fluid delivery device accessing member, the fluid delivery device attaching means reversibly securing a fluid delivery device in spaced relation with the fluid delivery device accessing member before or during operation of the device.

12. The combination of claim 1, wherein the container is a vial, the vial comprising a pierceable septum.

13. The combination of claim 1, wherein the receiving means accommodates a cover sealably connected to the dispensing member.

14. The combination of claim 1, wherein the dispensing member is selected from the group consisting of a blunt cannula, a sharp cannula, and a spray nozzle.

15. The combination of claim 1, wherein the dispensing member is a valved adapter.

16. The combination of claim 1, wherein the receiving means accommodates a needle safety mechanism in proximity to the dispensing member.

17. The combination of claim 1, wherein the fluid delivery device is a syringe with a plunger.

18. In combination:
a device for mixing and transferring, the device comprising: a
housing having a first open end and a second open end;
a container accessing member having at least one fluid conduit therethrough, the container accessing member extending generally outwardly from the first open end;
a fluid delivery device accessing member having at least one fluid conduit therethrough, the fluid delivery device accessing member extending generally towards the second open end, the fluid delivery device accessing member and the container accessing member in fluid communication therewith; and
a fluid delivery device reversibly securable to the second open end, the fluid delivery device comprising:
a dispensing member at a proximal end; and
a sealable access port at the proximal end configured to receive the fluid delivery device accessing member; and
a needle safety mechanism;
receiving means within the housing, the receiving means configured to receive a dispensing member and needle safety mechanism of the fluid delivery device, the receiving means separating the dispensing member of the fluid delivery device from the fluid delivery device accessing member; and
optionally, at least one container reversibly securable to the first open end, the at least one container optionally comprising a transferable substance.

19. The combination of claim 18, wherein the safety mechanism is user-activated or passively activated.

20. The combination of claim 18, wherein the needle safety mechanism comprises:
a needle cover assembly;
a latch connected to the needle cover assembly;
a latch shelf cooperatively engaging the latch; and
a deformable member positioned proximal to the dispensing member, the deformable member operably coupled to the latch;

wherein contacting of the deformable member by the plunger releases the latch from the latch shelf deploying the needle cover assembly.

* * * * *